(12) United States Patent
Zang et al.

(10) Patent No.: US 11,930,700 B2
(45) Date of Patent: Mar. 12, 2024

(54) NITROGEN-CONTAINING COMPOUND, ELECTRONIC ELEMENT, AND ELECTRONIC DEVICE

(71) Applicant: Shaanxi Lighte Optoelectronics Material Co., Ltd., Xi'an (CN)

(72) Inventors: Yan Zang, Xi'an (CN); Tiantian Ma, Xi'an (CN); Xinxuan Li, Xi'an (CN)

(73) Assignee: SHAANXI LIGHTE OPTOELECTRONICS MATERIAL CO., LTD., Shaanxi Xi'an (CN)

( * ) Notice: Subject to any disclaimer, the term of this patent is extended or adjusted under 35 U.S.C. 154(b) by 0 days.

(21) Appl. No.: 17/596,471

(22) PCT Filed: Oct. 22, 2020

(86) PCT No.: PCT/CN2020/122952
§ 371 (c)(1),
(2) Date: Dec. 10, 2021

(87) PCT Pub. No.: WO2021/135542
PCT Pub. Date: Jul. 8, 2021

(65) Prior Publication Data
US 2022/0384730 A1  Dec. 1, 2022

(30) Foreign Application Priority Data

Dec. 30, 2019 (CN) .......................... 201911404430.9
Sep. 10, 2020 (CN) .......................... 202010949522.1

(51) Int. Cl.
| | | |
|---|---|---|
| H10K 85/60 | (2023.01) | |
| C07C 211/54 | (2006.01) | |
| C07C 211/57 | (2006.01) | |
| C07C 211/58 | (2006.01) | |
| C07C 211/61 | (2006.01) | |
| C07D 209/86 | (2006.01) | |
| C07D 307/91 | (2006.01) | |
| C07D 333/76 | (2006.01) | |
| C09K 11/06 | (2006.01) | |
| H10K 50/15 | (2023.01) | |

(52) U.S. Cl.
CPC .......... *H10K 85/631* (2023.02); *C07C 211/54* (2013.01); *C07C 211/57* (2013.01); *C07C 211/58* (2013.01); *C07C 211/61* (2013.01); *C07D 209/86* (2013.01); *C07D 307/91* (2013.01); *C07D 333/76* (2013.01); *C09K 11/06* (2013.01); *H10K 50/15* (2023.02); *H10K 85/633* (2023.02); *H10K 85/636* (2023.02); *C07C 2603/18* (2017.05); *C07C 2603/26* (2017.05); *H10K 50/156* (2023.02); *H10K 85/615* (2023.02); *H10K 85/626* (2023.02); *H10K 85/6572* (2023.02); *H10K 85/6574* (2023.02); *H10K 85/6576* (2023.02)

(58) Field of Classification Search
CPC ............ C07C 2603/26; C07C 2603/18; C07D 307/91
See application file for complete search history.

(56) References Cited

U.S. PATENT DOCUMENTS

| | | | | |
|---|---|---|---|---|
| 10,879,471 | B2 * | 12/2020 | Miyake ............... | C07D 307/91 |
| 2019/0067576 | A1 * | 2/2019 | Voges .................... | H10K 50/18 |
| 2019/0140177 | A1 * | 5/2019 | Lee ........................ | C07D 307/91 |
| 2020/0303647 | A1 * | 9/2020 | Jeong .................... | H01L 51/006 |

FOREIGN PATENT DOCUMENTS

| | | | |
|---|---|---|---|
| CN | 108698978 A | | 10/2018 |
| CN | 108774515 A | * | 11/2018 |
| CN | 110382457 A | | 10/2019 |
| CN | 110577471 A | | 12/2019 |
| CN | 110740998 A | | 1/2020 |
| CN | 111793002 A | | 10/2020 |
| EP | 3247767 B1 | | 12/2018 |
| KR | 10-2019-0063821 A | | 6/2019 |
| KR | 20200050407 | * | 5/2020 |

OTHER PUBLICATIONS

EP 3312166 (Tanaka et al) filed Oct. 18, 2017. (Year: 2017).*
Dong et al., machine translation of CN-108774515-A (2018) pp. 1-23. (Year: 2018).*
Ham et al., machine translation of KR 20200050407 (2020) pp. 1-28. (Year: 2020).*
International Search Report from corresponding International Application No. PCT/CN2020/122952, dated Dec. 31, 2020, 4 pages.

* cited by examiner

*Primary Examiner* — Dylan C Kershner
(74) *Attorney, Agent, or Firm* — Tucker Ellis LLP

(57) ABSTRACT

A nitrogen-containing compound as shown in Chemical formula (1), an electronic element, and an electronic device are provided. In Chemical formula (1), $Ar_1$ and $Ar_2$ are selected from a substituted or unsubstituted C6 to C30 aryl, a substituted or unsubstituted C3 to C30 heteroaryl, or a substituted or unsubstituted C3 to C20 cycloalkyl; $Ar_3$ is selected from a substituted or unsubstituted C6 to C20 aryl, or a substituted or unsubstituted C3 to C20 heteroaryl.

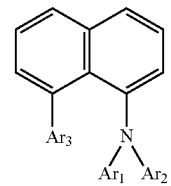

Chemical formula (1)

8 Claims, 2 Drawing Sheets

NITROGEN-CONTAINING COMPOUND, ELECTRONIC ELEMENT, AND ELECTRONIC DEVICE

CROSS-REFERENCE TO RELATED APPLICATIONS

This application claims the priority to a Chinese invention patent application whose Application date is Dec. 30, 2019, Patent Application No. CN201911404430.9, entitled "Nitrogen-containing compound, electronic element, and electronic device" and a Chinese invention patent application whose Application date is Sep. 10, 2020, Patent Application No. CN202010949522.1, entitled "Nitrogen-containing compound, electronic element, and electronic device", which are incorporated herein into the present application as a part of it.

TECHNICAL FIELD

This application relates to the technical field of organic materials, and specifically, to a nitrogen-containing compound, an electronic element, and an electronic device.

BACKGROUND

Organic electroluminescent materials (OLED), as a new generation of display technology, have the advantages of ultra-thin, self-lighting, wide viewing angle, fast response, high luminescence efficiency, good temperature adaptability, simple production process, low driving voltage and low energy consumption, and has been widely used in industries the such as flat-panel displays, flexible displays, solid-state lighting and vehicle mounted displays.

An organic light-emitting device generally includes an anode, a cathode and an organic material layer between the anode and the cathode. The organic material layer is generally formed by a multilayer structure composed of different materials to improve the luminance, efficiency and service life of the organic electroluminescent device. The organic material layer may be composed of a hole injection layer, a hole transport layer, a light-emitting layer, an electron transport layer, an electron injection layer, etc. In the structure of the organic light-emitting device, when a voltage is applied between the two electrodes, holes and electrons are injected into the organic material layer from the anode and the cathode, respectively, the injected holes and electrons combine to form excitons, and the excitons emit light when they decay to the ground state.

However, it is still necessary to continue developing new materials to further improve the performance of electronic elements.

The above information disclosed in the background part is used only for enhancing the understanding of the background of this application, and therefore may include information that does not constitute the related art known to those ordinary skilled in the art.

SUMMARY

An objective of this application is to provide a nitrogen-containing compound, an electronic element, and an electronic device to improve the performance of an organic electroluminescent device.

To achieve the above objective, this application adopts the following technical solutions.

A first aspect of this application provides a nitrogen-containing compound having a structural formula as shown in Chemical formula (1):

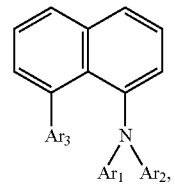

Chemical formula (1)

where, $Ar_1$ and $Ar_2$ are selected from a substituted or unsubstituted C6 to C30 aryl, a substituted or unsubstituted C3 to C30 heteroaryl, or a substituted or unsubstituted C3 to C20 cycloalkyl; $Ar_3$ is selected from a substituted or unsubstituted C6 to C20 aryl, or a substituted or unsubstituted C3 to C20 heteroaryl;

the substituents on $Ar_1$, $Ar_2$, and $Ar_3$ are identical or different and are respectively independently selected from deuterium, a cyano, a halogen, a C1 to C3 linear alkyl, a C3 to C7 branched alkyl, a C6 to C18 aryl, a C3 to C18 heteroaryl, a C3 to C10 cycloalkyl, a C2 to C7 heterocycloalkyl, or a C1 to C7 alkoxy.

A second aspect of this application provides an electronic element, comprising an anode and a cathode disposed oppositely, and a functional layer disposed between the anode and the cathode, wherein the functional layer comprises the above nitrogen-containing compound.

A third aspect of this application provides an electronic device comprising the above electronic element.

The nitrogen-containing compound in this application has substituents at positions 1 and 8 of naphthalene, respectively, the substituent linked at position 1 is a smaller aryl substituent such as a phenyl or a biphenyl, and the substituent linked at position 8 is triarylamine, which makes the whole molecule asymmetric and increases the amorphism of the material, making the transport of charges smoother. Moreover, because the positions of $Ar_1$, $Ar_2$ and $Ar_3$ are close to each other, the steric hindrance between the substituents is large, and the substituent $Ar_3$ and the substituents $Ar_1$ and $Ar_2$ rotate to a certain extent, which can adjust the angle and conjugation of the branches of amine, so as to adjust the HOMO value of the nitrogen-containing compound, so that the HOMO value of the nitrogen-containing compound can better match the adjacent membrane layer, thereby lowering the driving voltage of the organic electroluminescent device.

BRIEF DESCRIPTION OF THE DRAWINGS

The above and other features and advantages of this application will become more apparent from the detailed description of exemplary embodiments of this application made with reference to the accompanying drawings.

Figure 1:
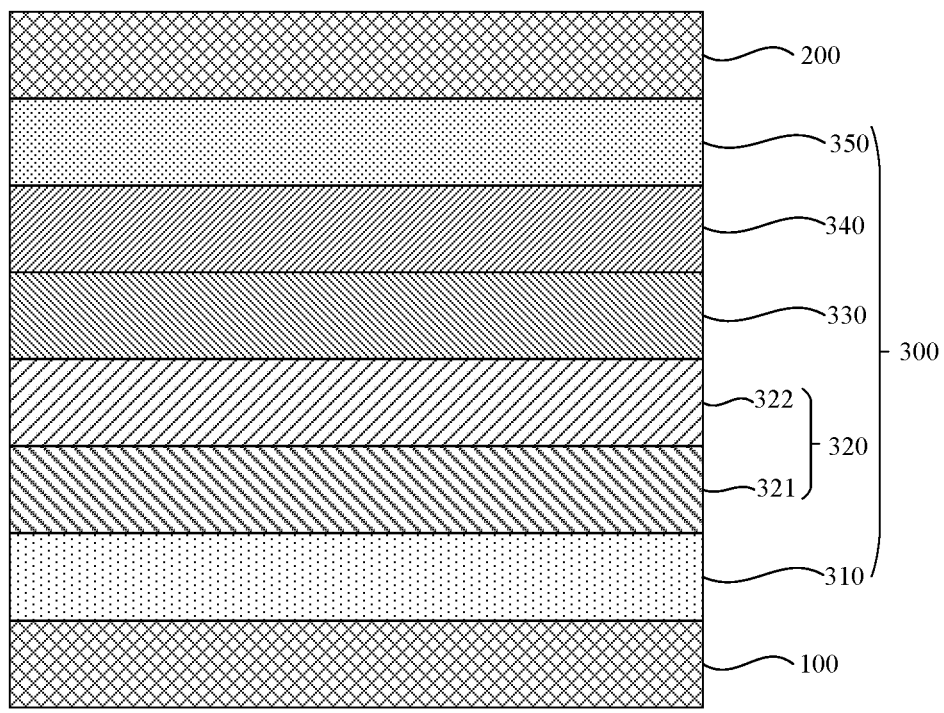
FIG. 1 is a schematic structural diagram of an organic electroluminescent device according to an embodiment of this application.

List of Reference Numerals: 100. Anode; 200. Cathode; 300. Functional layer; 310. Hole injection layer; 320. Hole transport layer; 321. First hole transport layer; 322. Second hole transport layer; 330. Organic light-emitting layer; 340. Electron transport layer; 350. Electron injection layer; 360. Photoelectric conversion layer; 400. Electronic device; 500. Electronic device.

DETAILED DESCRIPTION

Exemplary embodiments will be described more comprehensively with reference to the accompanying drawings. However, the exemplary embodiments can be implemented in a plurality of forms, and should not be understood as being limited to the examples described herein. Conversely, the embodiments are provided to make this application more comprehensive and complete, and comprehensively convey the idea of the exemplary embodiments to those skilled in the art. The described features, structures or characteristics may be combined in one or more embodiments in any appropriate manner. In the following descriptions, a lot of specific details are provided to give a comprehensive understanding of the embodiments of this application.

In the figures, for clarity, the thicknesses of regions and layers may be exaggerated. Same reference numerals in the figures represent same or similar structures, and therefore detailed descriptions of the structures will be omitted.

The embodiments of this application provide a nitrogen-containing compound having a structural formula as shown in Chemical formula (1):

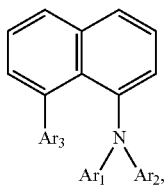

Chemical formula (1)

where, $Ar_1$ and $Ar_2$ are selected from a substituted or unsubstituted C6 to C30 aryl, a substituted or unsubstituted C3 to C30 heteroaryl, or a substituted or unsubstituted C3 to C20 cycloalkyl; $Ar_3$ is selected from a substituted or unsubstituted C6 to C20 aryl, or a substituted or unsubstituted C3 to C20 heteroaryl;

the substituents on $Ar_1$, $Ar_2$, and $Ar_3$ are identical or different and are respectively independently selected from deuterium, a cyano, a halogen, a C1 to C3 linear alkyl, a C3 to C7 branched alkyl, a C6 to C18 aryl, a C3 to C18 heteroaryl, a C3 to C10 cycloalkyl, a C2 to C7 heterocycloalkyl, or a C1 to C7 alkoxy.

The nitrogen-containing compound in this application has substituents at positions 1 and 8 of naphthalene, respectively, the substituent linked at position 1 is a smaller aryl substituent such as a phenyl, a naphthalene or a biphenyl, and the substituent linked at position 8 is triarylamine. Such a combination makes the whole molecule asymmetric and increases the amorphism of the material, making the transport of charges smoother. In addition, the smaller aryl substituent at position 1 has little impact on the hole transport characteristics of the triarylamine, which ensures a high hole mobility of the entire material. Moreover, because the positions of $Ar_1$, $Ar_2$ and $Ar_3$ are close to each other, the steric hindrance between the substituents is large, and the substituent $Ar_3$ and the substituents $Ar_1$ and $Ar_2$ rotate to a certain extent, which can adjust the angle and conjugation of the branches of amine, so as to adjust the HOMO value of the nitrogen-containing compound, so that the HOMO value of the nitrogen-containing compound can better match the adjacent membrane layer, thereby lowering the driving voltage of the organic electroluminescent device.

For example, taking the following structural formula as an example, $Ar_1$ is a biphenyl, $Ar_2$ is a biphenyl, and $Ar_3$ is a phenyl. This structural formula shows the three-dimensional structure of the compound. It can be seen that the substituent $Ar_3$ and the substituents $Ar_1$ and $Ar_2$ rotate to a certain extent. Although the other structural formulas of the compounds listed in this application are drawn as planar structures, they all have similar three-dimensional structures.

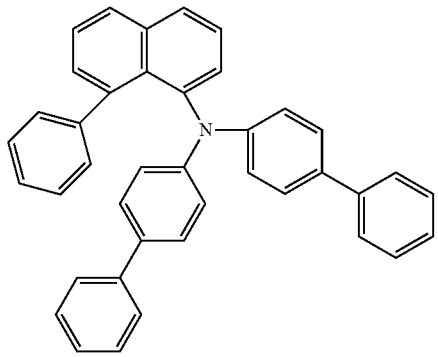 [SMILES: c1ccc(-c2ccc(N(c3ccc(-c4ccccc4)cc3)c3cccc4cccc(-c5ccccc5)c34)cc2)cc1]

In this application, the number of carbon atoms of $Ar_1$, $Ar_2$, and $Ar_3$ refers to the number of all carbon atoms. For example, if $Ar_1$ is selected from a substituted C10 aryl, the total number of all carbon atoms of the aryl and the substituents thereon is 10.

In this application, the descriptions "each . . . is independently" and " . . . respectively independently" and " . . . independently selected from" are interchangeable, and should be understood in a broad sense, which can mean that the specific options expressed by identical symbols in different groups do not affect each other, and can also mean that the specific options expressed by identical symbols in the same group do not affect each other. For example,

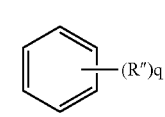

formula Q-1

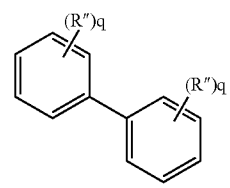

formula Q-2 where each q is independently 0, 1, 2 or 3, and each R" is independently selected from hydrogen, deuterium, fluorine, and chlorine" has the following meaning: formula Q-1 means that there are q substituents R" on the benzene ring, and each R" may be identical or different, and the options of each R" do not affect each other; formula Q-2 means that each benzene ring of biphenyl has q substituents R", the numbers q of substituents R" on two benzene rings may be identical or different from each other, each R" may be identical or different, and the options of each R" do not affect each other.

In this application, the term "substituted or unsubstituted" means that the functional group modified by the term may have or may not have a substituent (hereinafter, for ease of description, the substituents are collectively referred to as Rc). For example, "a substituted or unsubstituted aryl" refers to an aryl having a substituent Rc or to an unsubstituted aryl. Wherein the above substituent, i.e., Rc, can be, for example, deuterium, a halogen, a cyano, a C3 to C20 heteroaryl, a C6 to C20 aryl, a C3 to C12 trialkylsilyl, a C18 to C30 triarylsilyl, a C1 to C10 alkyl, a C1 to C10 haloalkyl, a C2 to C6 alkenyl, a C2 to C6 alkynyl, a C3 to C10 cycloalkyl, a C2 to C10 heterocycloalkyl, a C5 to C10 cycloalkenyl, a C4 to C10 heterocyclenyl, a C1 to C10 alkoxy, a C1 to C10 alkylamine, a C1 to C10 alkylthio, a C6 to C18 aryloxy, a C6 to C18 arylthio, a C6 to C18 alkylsulfonyl, a C3 to C18 trialkylphosphino, or a C3 to C18 trialkylboron.

In this application, in the phrase "any two adjacent substituents form a ring", "any adjacent" can include two substituents on the same atom, and can also include one substituent respectively on each of two adjacent atoms. When there are two substituents on the same atom, the two substituents may form a saturated or unsaturated ring (for example, a saturated or unsaturated C3 to C18 ring) with the atom to which they are both linked. When two adjacent atoms each have one substituent, the two substituents may be fused to form a ring, such as a naphthalene ring, a phenanthrene ring, or an anthracene ring.

In this application, when no other specific definition is provided, "hetero" means that a functional group includes at least one heteroatom such as B, N, O, S, Si, Se, Ge, or P, and the remaining atoms are carbon and hydrogen. An unsubstituted alkyl may be a "saturated alkyl" without any double or triple bonds.

In this application, "alkyl" may include linear alkyl or branched alkyl. The alkyl may have 1 to 20 carbon atoms (C1 to C20). In this application, numerical ranges such as "1 to 20" refer to individual integers in the given range. For example, the C1 to C20 alkyl refers to an alkyl having 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms or 20 carbon atoms. The alkyl may also be a medium-sized alkyl having 1 to 10 carbon atoms. The alkyl may also be a lower alkyl having 1 to 6 carbon atoms. In addition, the alkyl may be substituted or unsubstituted. Specific examples of the alkyl having 1 to 10 carbon atoms include, but are not limited to, methyl, ethyl, n-propyl, isopropyl, n-butyl, isobutyl, tert-butyl, n-pentyl, isopentyl, neopentyl, n-hexyl, n-heptyl, n-octyl, 2-ethylhexyl, nonyl, decyl, etc.

In this application, "alkenyl" refers to a hydrocarbyl containing one or more double bonds in a linear or branched hydrocarbon chain. The alkenyl may be substituted or unsubstituted. The alkenyl may have 1 to 20 carbon atoms (C1 to C20). Numerical ranges such as "1 to 20" refers to individual integer in the given range throughout this application. For example, the C1 to C20 alkenyl refers to an alkenyl having 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms or 20 carbon atoms. For example, the alkenyl may be vinyl, butadiene, or 1,3,5-hexatriene.

In this application, the cycloalkyl refers to a saturated hydrocarbyl containing an alicyclic structure, including monocyclic and fused poly cyclic structures. The cycloalkyl may have 3 to 20 carbon atoms (C3 to C20). Numerical ranges such as "3 to 20" refers to individual integers in the given range. The C3 to C20 cycloalkyl refers to a cycloalkyl having 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms or 20 carbon atoms. The cycloalkyl may be a small ring, an ordinary ring, or a large ring having 3 to 20 carbon atoms. The cycloalkyl may also be monocyclic (with only one ring), bicyclic (with two rings), or polycyclic (with three or more rings). The cycloalkyl may also be spirocyclic (with two rings sharing one carbon atom), fused polycyclic (with two rings sharing two carbon atoms), or bridged (with two rings sharing two or more carbon atoms). In addition, the cycloalkyl may be substituted or unsubstituted. The number of carbon atoms of the C3 to C10 cycloalkyl may be 3, 5, 6, 7, 8, 9, or 10, for example. Specific examples of the C3 to C10 cycloalkyl include, but are not limited to, cyclopentyl, cyclohexyl, etc.

In this application, the aryl refers to any functional group or substituent derived from an aromatic ring. The aryl may be a monocyclic aryl or a polycyclic aryl. In other words, the aryl may be a monocyclic aryl, fused polycyclic aryl, two or more monocyclic aryls conjugated through carbon-carbon bonds, a monocyclic aryl and a fused polycyclic aryl conjugated through carbon-carbon bonds, or two or more fused polycyclic aryls conjugated through carbon-carbon bonds. That is, two or more aryls conjugated through carbon-carbon bonds can also be regarded as the aryl in this application, wherein, the aryl does not contain any heteroatom such as B, N, O, S, Si, Se, Ge, or P. For example, in this application, biphenyl, terphenyl, etc. are aryls. Examples of the aryl may include, but are not limited to, phenyl, naphthyl, fluorenyl, anthracenyl, phenanthryl, biphenyl, terphenyl, tetraphenyl, pentaphenyl, hexaphenyl, benzo[9,10]phenanthryl, pyrenyl, benzofluoranthenyl, phenanthryl, etc.

In this application, a substituted aryl means that one or more hydrogen atoms in the aryl are substituted with other groups. For example, at least one hydrogen atom is substituted with a deuterium atom, F, Cl, I, CN, a hydroxyl, an amino, a branched alkyl, a linear alkyl, a cycloalkyl, an alkoxy, an alkylamino, an alkylthio, an aryl, a heteroaryl or other groups. It can be understood that the number of carbon atoms of the substituted aryl refers to the total number of carbon atoms of the aryl and the substituents on the aryl. For example, a substituted C18 aryl refers to that the total number of carbon atoms of the aryl and the substituents on the aryl is 18. For example, 9,9-dimethylfluorenyl is a substituted C15 aryl.

In this application, the aryl as the substituent is, for example, but not limited to, phenyl, biphenyl, naphthyl, 9,9-dimethylfluorenyl, 9,9-diphenylfluorenyl, phenanthryl, anthryl, 1,10-phenanthrolinyl, etc.

In this application, the heteroaryl may be a heteroaryl having at least one of B, N, O, S, Si, Se, Ge, or P as a heteroatom. The heteroaryl may be a monocyclic heteroaryl or a polycyclic heteroaryl. In other words, the heteroaryl may be a single aromatic ring system or multiple aromatic ring systems conjugated through carbon-carbon bonds, and any aromatic ring system is an aromatic monocyclic ring or an aromatic fused ring. Exemplarily, the heteroaryl may include, but are not limited to, thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, N-arylcarbazolyl, N-heteroarylcarbazolyl, N-alkylcarbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, dibenzosilyl, dibenzofuranyl, phenyl-substituted dibenzofuranyl, dibenzofuranyl-substituted phenyl, etc. Wherein thienyl, furanyl, or phenanthrolinyl is a heteroaryl of a single aromatic ring system, and N-arylcarbazolyl, N-heteroarylcarbazolyl, phenyl-substituted dibenzofuranyl, or dibenzofuranyl-substituted phenyl is a heteroaryl of multiple aromatic ring systems conjugated through carbon-carbon bonds.

In this application, the heteroaryl as a substituent is, for example, pyridyl, carbazolyl, pyrimidinyl, pyridazinyl, triazinyl, quinolinyl, isoquinolinyl, quinazolinyl, pyrazinyl, dibenzothienyl, dibenzofuranyl, etc.

The non-position-specific bond in this application refers to a single bond "⸺" extending from the ring system, which means that one end of the bond can be connected to any position in the ring system through which the bond passes and the other end of the bond is connected to another part of the compound molecule.

For example, as shown in the following formula (f), the naphthyl represented by formula (f) is connected to other positions of the molecule through two non-position-specific bonds that penetrate the bicyclic ring, where the connection includes any possible connection mode shown in formula (f-1) to formula (f-10).

(f)

(f-1)

(f-2)
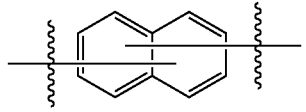

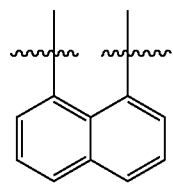

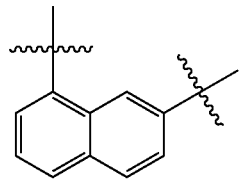

(f-3)
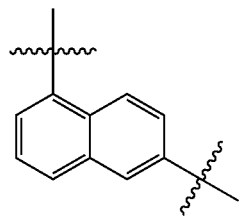

(f-4)

(f-5)
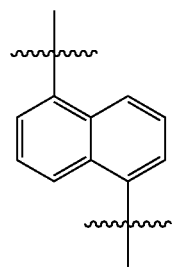

(f-6)
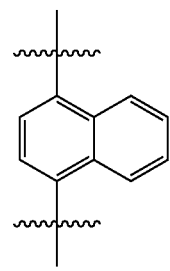

(f-7)
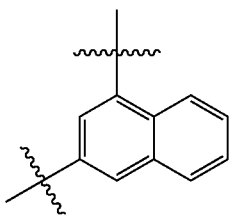

(f-8)
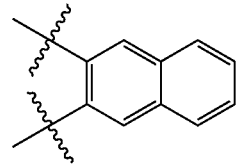

(f-9)
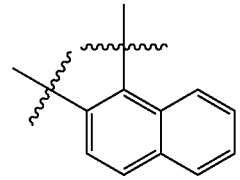

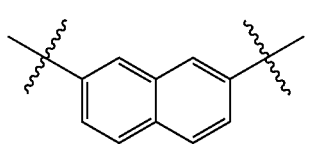

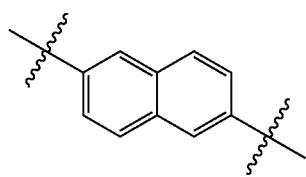
(f-10)

For another example, as shown in the following formula (X'), the phenanthryl represented by formula (X') is connected to other positions of the molecule through a non-position-specific bond extending from the middle of the benzene ring on one side, where the connection includes any possible connection mode shown in formula (X'-1) to formula (X'-4).

(X')

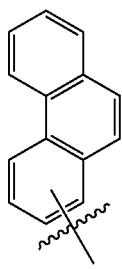

(X'-1)

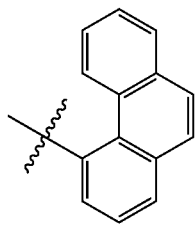

(X'-2)

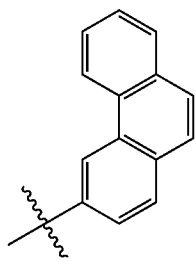

(X'-3)

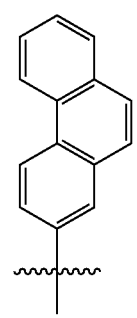

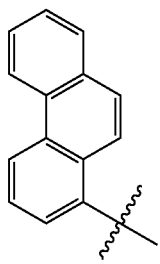
(X'-4)

The non-position-specific substituent in this application refers to a substituent connected by a single bond extending from the center of the ring system, which means that the substituent can be connected at any possible position in the ring system. For example, as shown in the following formula (Y), the substituent R represented by formula (Y) is connected to the quinoline ring through a non-position-specific bond, where the connection includes any possible connection mode shown in formula (Y-1) to formula (Y-7).

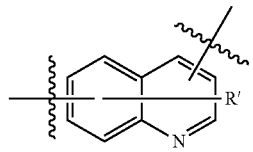
(Y)

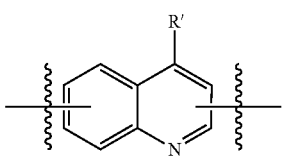
(Y-1)

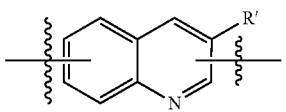
(Y-2)

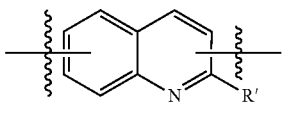
(Y-3)

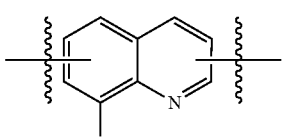
(Y-4)

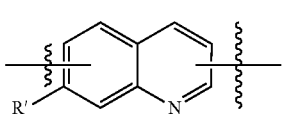
(Y-5)

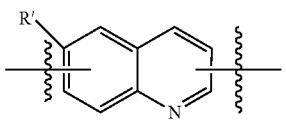
(Y-6)

-continued

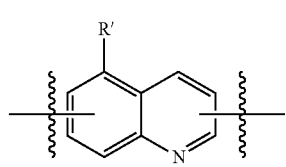
(Y-7)

In this application, the halogen may be, for example, fluorine, chlorine, bromine, or iodine.

In this application, specific examples of the trialkylsilyl include, but are not limited to, trimethylsilyl, triethylsilyl, etc.

In this application, specific examples of the triarylsilyl include, but are not limited to, triphenylsilyl, etc.

In this application, specific examples of the haloalkyl include, but are not limited to, trifluoromethyl.

The meaning of non-position-specific connection or non-position-specific substitution in the following description is the same as that described herein, and will not be repeated hereinafter.

Optionally, the substituents on $Ar_1$, $Ar_2$, and $Ar_3$ are identical or different and are respectively independently selected from deuterium, a cyano, a fluorine, a C1 to C3 linear alkyl, a C3 to C5 branched alkyl, a C6 to C18 aryl, or a C3 to C18 heteroaryl.

Optionally, $Ar_3$ is selected from the group consisting of the following groups:

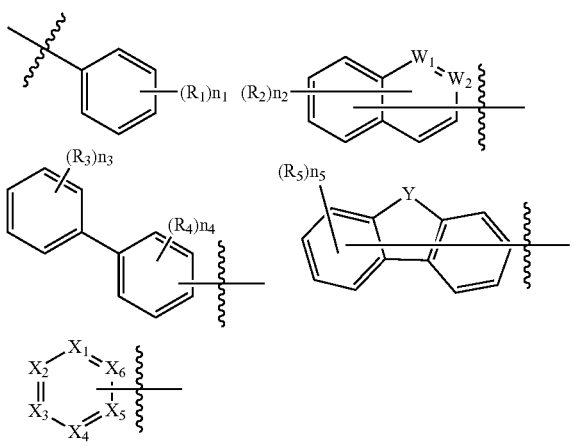

where,
$n_1$ and $n_3$ are identical or different and are respectively independently selected from 1, 2, 3, 4, or 5;
$n_2$ is selected from 1, 2, 3, 4, 5, 6, or 7;
$n_4$ and $n_5$ are identical or different and are respectively independently selected from 1, 2, 3, or 4;
$W_1$ and $W_2$ are identical or different and are respectively independently selected from C or N, where when $W_1$ and $W_2$ are selected from C, it means that $W_1$ and $W_2$ are CH;
Y is selected from O, S, $Si(R_6R_7)$, $C(R_8R_9)$, $N(R_{10})$, or Se;
$R_1$ to $R_{10}$ are identical or different and are respectively independently selected from hydrogen, deuterium, a halogen, a cyano, a C1 to C10 alkyl, a C6 to C18 aryl, a C3 to C18 heteroaryl, or a C3 to C10 cycloalkyl; or $R_6$ and $R_7$ may be linked to form a ring, or $R_8$ and $R_9$ may be linked to form a ring;

$X_1$ to $X_6$ are identical or different and are respectively independently selected from C(R') or N, and at least one of $X_1$ to $X_6$ is N, where, R' in $X_1$ to $X_7$ are identical or different and are respectively independently selected from hydrogen, a C1 to C10 alkyl, a C6 to C18 aryl, a C3 to C18 heteroaryl, or a C3 to C10 cycloalkyl, or any two adjacent R' may be linked to form a ring.

In this application, when $n_1$, $n_2$, $n_3$, $n_4$, and $n_5$ are selected from 0, the benzene ring is not substituted.

In this application, $n_1$ is the number of substituent $R_1$, and when $n_1$ is greater than or equal to 2, any two $R_1$ are identical or different; $n_2$ is the number of substituent $R_2$, and when $n_2$ is greater than or equal to 2, any two $R_2$ are identical or different; $n_3$ is the number of substituent $R_3$, and when $n_3$ is greater than or equal to 2, any two $R_3$ are identical or different; $n_4$ is the number of substituent $R_4$, and when $n_4$ is greater than or equal to 2, any two $R_4$ are identical or different; $n_5$ is the number of substituent $R_5$, and when $n_5$ is greater than or equal to 2, any two $R_5$ are identical or different.

That any two adjacent R' may be linked to form a ring means that $X_1$ and $X_2$ form a ring, or $X_2$ and $X_3$ form a ring, or $X_3$ and $X_4$ form a ring, or $X_4$ and $X_5$ form a ring, or $X_5$ and $X_6$ form a ring, or $X_6$ and $X_1$ form a ring, and certainly includes the case that $X_2$ and $X_3$ form a ring and $X_5$ and $X_6$ also form a ring.

In this application, the meaning that A and B "may be linked to form a ring" includes the case that A and B are independent of each other and are not connected; and also includes the case that A and B are linked to form a ring. For example, that $R_6$ and $R_7$ may be linked to form a ring includes the case that $R_6$ and $R_7$ are independent of each other and are not linked, and also includes the case that $R_6$ and $R_7$ are linked to form a ring; that $R_8$ and $R_9$ may be linked to form a ring includes the case that $R_8$ and $R_9$ are independent of each other and are not linked, and also includes the case that $R_8$ and $R_9$ are linked to form a ring.

For example, that $X_3$ and $X_4$ may be linked to form a ring, includes the case that R' of $X_3$ and R' of $X_4$ are independent of each other and are not linked, and also includes the case that R' of $X_3$, R' of the $X_4$, and the atom connected to R' form a ring.

In this application, the ring refers to a saturated or unsaturated ring. Optionally, the number of carbon atoms of the ring may be 5, e.g.,

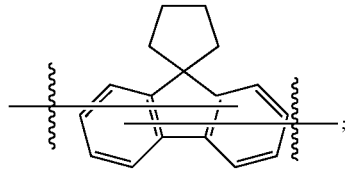

or may be 6, e.g.,

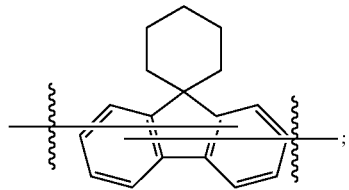

or may be 13, e.g.,

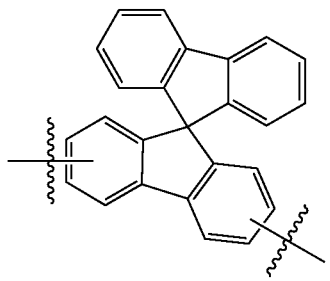

Certainly, the number of carbon atoms that form a ring may also be other values, which will not be enumerated herein. The number of carbon atoms in the ring is not particularly limited in this application.

Optionally, Ar$_3$ is selected from a substituted or unsubstituted C6 to C15 aryl.

Optionally, Ar$_3$ is selected from the group consisting of the following groups:

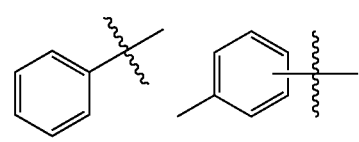

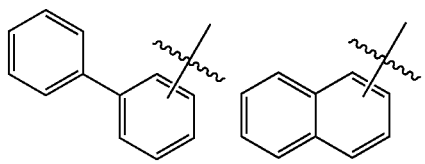

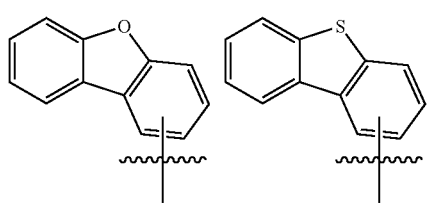

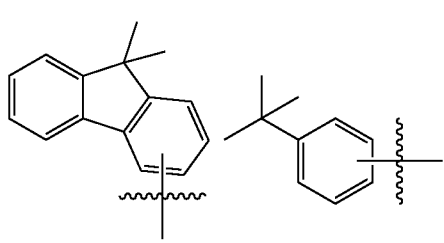

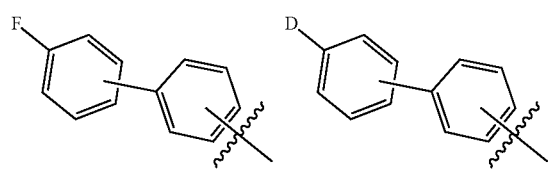

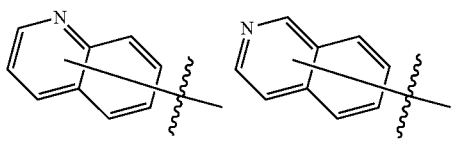

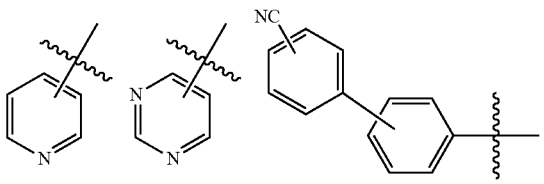

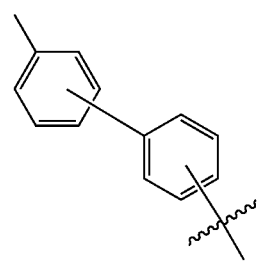

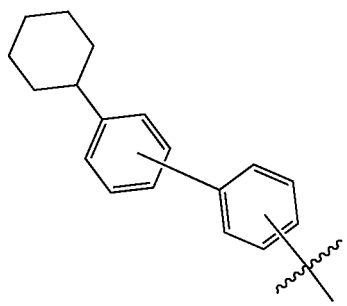

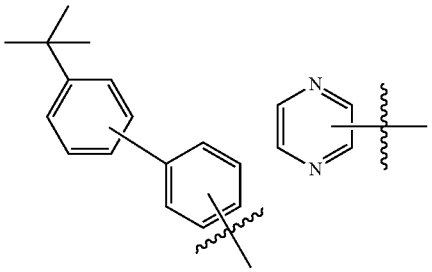

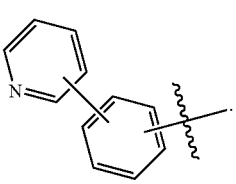

Optionally, Ar$_3$ is selected from the group consisting of the following groups:

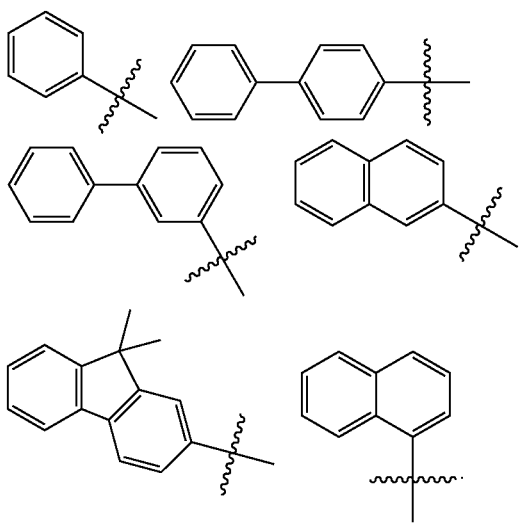

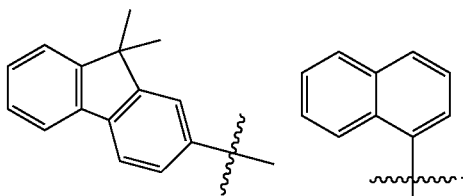

Optionally, Ar$_3$ is selected from the following substituted or unsubstituted groups: phenyl, naphthalyl, biphenyl, terphenyl, phenanthryl, anthracyl, 9,9-dimethylfluorenyl, pyridyl, carbazolyl, pyrimidinyl, 1,10-phenanthrolinyl, pyridazinyl, triazinyl, quinolinyl, isoquinolinyl, quinazolinyl, pyrazinyl, quinoxyl, pyrenyl, N-phenylcarbazolyl, dibenzofuranyl, or dibenzothienyl. http://chanpin.molbase.cn/c4569-45-3/http://chanpin.molbase.cn/c253-82-7/ http://chanpin.molbase.cn/c91-19-0/

The substitution is substitution with a substituent selected from the following groups: deuterium, fluorine, cyano, trimethylsilyl, methyl, ethyl, isopropyl, tert-butyl, phenyl, naphthalyl, pyridyl, dibenzfurfuranyl, cyclohexanyl, carbazolyl or dibenzothienyl. When there are multiple substituents, the multiple substituents are identical or different.

The substituent on Ar$_3$ is selected from deuterium, fluorine, cyano, trimethylsilyl, methyl, ethyl, isopropyl, tert-butyl, phenyl, naphthalyl, pyridyl, dibenzfurfuranyl, cyclohexanyl, carbazolyl or dibenzothienyl.

Optionally, Ar$_1$ and Ar$_2$ are selected from the group consisting of the following groups:

i-1

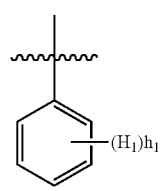

i-2

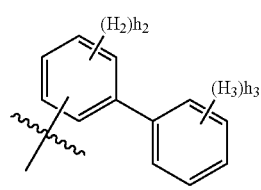

i-3

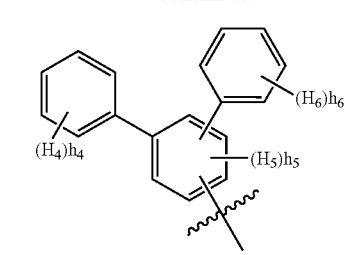

i-4

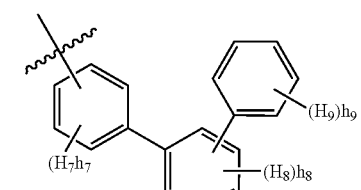

i-5

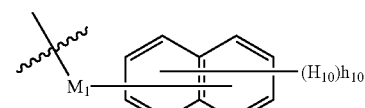

i-6

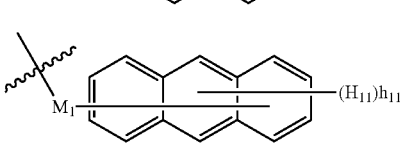

i-7

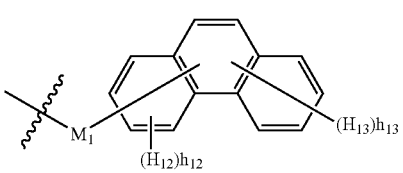

i-8

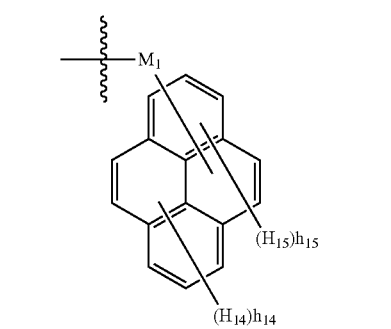

i-9

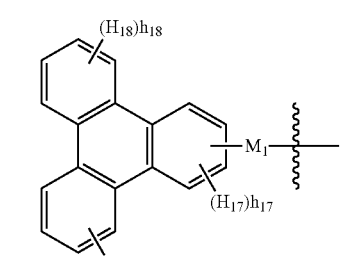

i-10

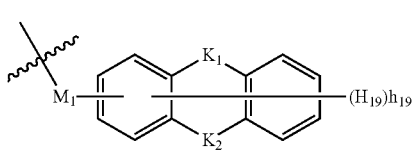

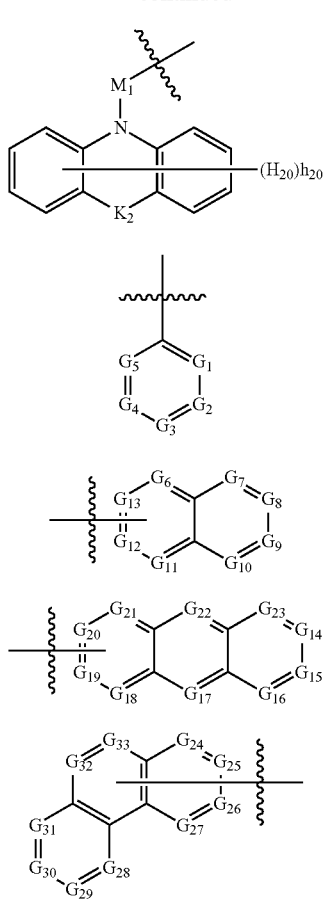

i-11 i-12 i-13 i-14 i-15 wherein, $M_1$ is selected from a single bond or

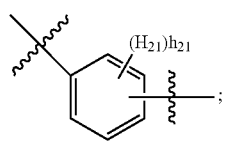

$G_1$ to $G_5$ are each independently selected from N or $C(F_1)$, and at least one of $G_1$ to $G_5$ is selected from N; when two or more of $G_1$ to $G_5$ are selected from $C(F_1)$, any two $F_1$ are identical or different;

$G_6$ to $G_{13}$ are each independently selected from N or $C(F_2)$, and at least one of $G_6$ to $G_{13}$ is selected from N; when two or more of $G_6$ to $G_{13}$ are selected from $C(F_2)$, any two $F_2$ are identical or different;

$G_{14}$ to $G_{23}$ are each independently selected from N or $C(F_3)$, and at least one of $G_{14}$ to $G_{23}$ is selected from N; when two or more of $G_{14}$ to $G_{23}$ are selected from $C(F_3)$, any two $F_3$ are identical or different;

$G_{24}$ to $G_{33}$ are each independently selected from N or $C(F_4)$, and at least one of $G_{24}$ to $G_{33}$ is selected from N; when two or more of $G_{24}$ to $G_{33}$ are selected from $C(F_4)$, any two $F_4$ are identical or different;

$H_1$ to $H_{21}$ and $F_1$ to $F_4$ are identical or different from each other and are each independently selected from: hydrogen, deuterium, a fluorine, a chlorine, a bromine, a cyano, a C6 to C18 aryl, a C3 to C18 heteroaryl, a C3 to C12 trialkylsilyl, a C8 to C12 arylsilyl, a C1 to C10 alkyl, a C1 to C10 haloalkyl, a C3 to C10 cycloalkyl, a C2 to C10 heterocycloalkyl, or a C1 to C10 alkoxy, where, $H_1$ to $H_3$ and $H_{21}$ cannot be aryl;

$h_k$ is the number of Substituent $H_k$, where k is any integer from 1 to 21; where, when k is selected from 5 or 17, $h_k$ is selected from 1, 2, or 3; when k is selected from 2, 7, 8, 12, 15, 16, 18, or 21, $h_k$ is selected from 1, 2, 3, or 4; when k is selected from 1, 3, 4, 6, 9, or 14, $h_k$ is selected from 1, 2, 3, 4, or 5; when k is 13, $h_k$ is selected from 1, 2, 3, 4, 5, or 6; when k is selected from 10 or 19, $h_k$ is selected from 1, 2, 3, 4, 5, 6, or 7; when k is selected from 20, $h_k$ is selected from 1, 2, 3, 4, 5, 6, 7, or 8; when k is 11, $h_k$ is selected from 1, 2, 3, 4, 5, 6, 7, 8, or 9; when $h_k$ is greater than 1, any two $H_k$ are identical or different;

$K_1$ is selected from O, S, Se, $N(H_{22})$, $C(H_{23}H_{24})$, or $Si(H_{23}H_{24})$; where, $H_{22}$, $H_{23}$, and $H_{24}$ are identical or different from each other and are each independently selected from: a C6 to C18 aryl, a C3 to C18 heteroaryl, a C1 to C10 alkyl, a C3 to C10 cycloalkyl, or a C2 to C10 heterocycloalkyl, or $H_{23}$ and $H_{24}$ may be linked to form a ring;

$K_2$ is selected from a single bond, O, S, Se, $N(H_{25})$, $C(H_{26}H_{27})$, or $Si(H_{26}H_{27})$; where, $H_{25}$, $H_{26}$, and $H_{27}$ are identical or different from each other and are each independently selected from: a C6 to C18 aryl, a C3 to C18 heteroaryl, a C1 to C10 alkyl, a C3 to C10 cycloalkyl, or a C2 to C10 heterocycloalkyl, or $H_{26}$ and $H_{27}$ may be linked to form a ring.

Optionally, $Ar_1$ and $Ar_2$ are selected from a substituted or unsubstituted C6 to C25 aryl, or a substituted or unsubstituted C4 to C20 heteroaryl.

The substituents on $Ar_1$ and $Ar_2$ are selected from deuterium, a fluorine, a cyano, a trimethylsilyl, a methyl, an ethyl, an isopropyl, a tert-butyl, a phenyl, a naphthalyl, a pyridyl, a dibenzfurfuranyl, a cyclohexanyl, a 9,9-dimethylfluorenyl, a carbazolyl or a dibenzothienyl.

Optionally, $Ar_1$ and $Ar_2$ are selected from the group consisting of the following groups:

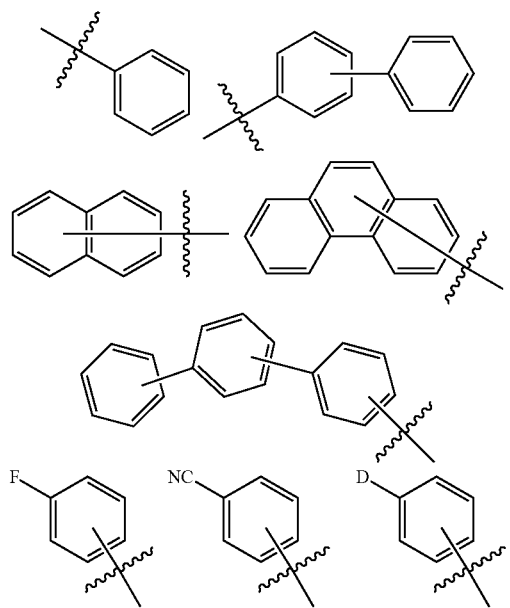

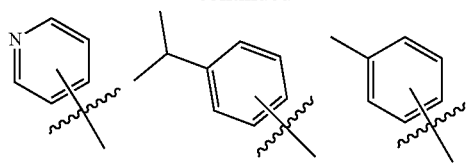
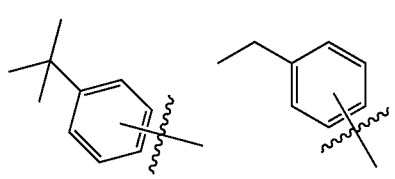
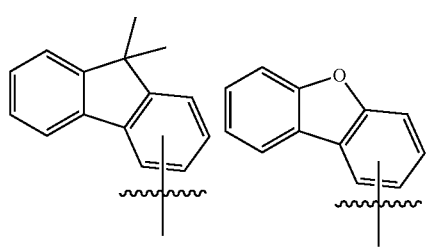
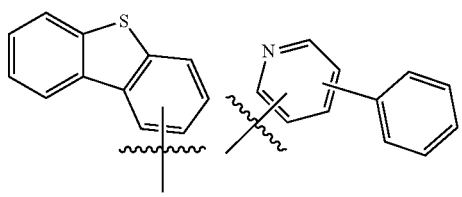
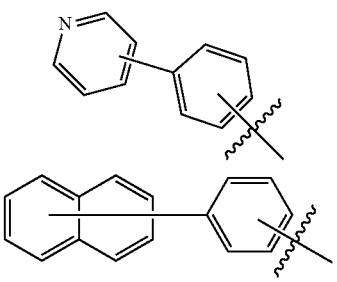
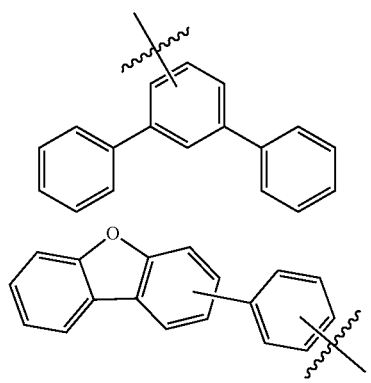
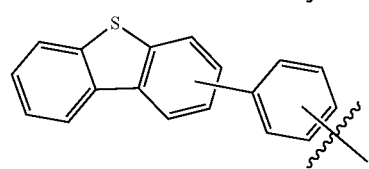
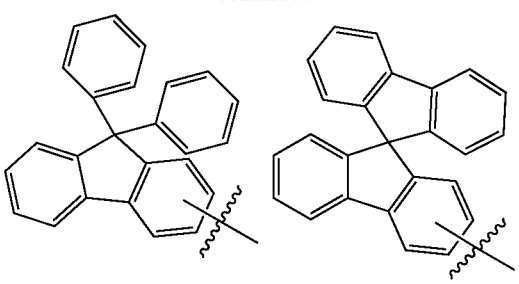
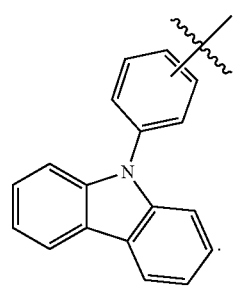
Optionally, Ar$_1$ and Ar$_2$ are selected from the group consisting of the following groups:
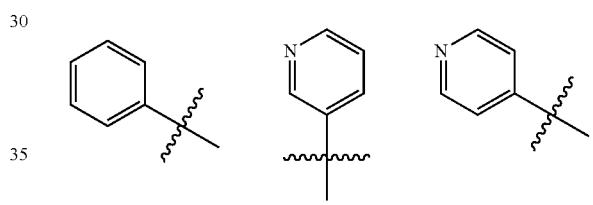
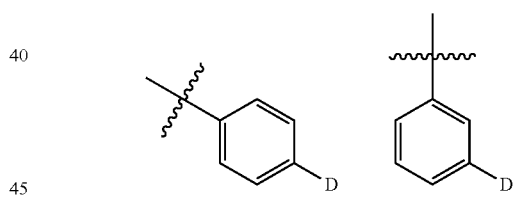
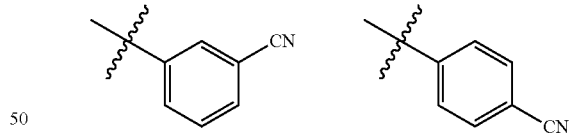
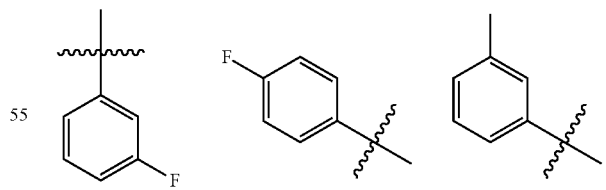
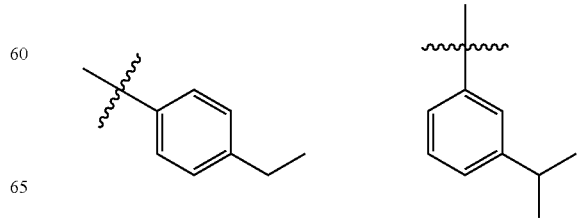

21
-continued
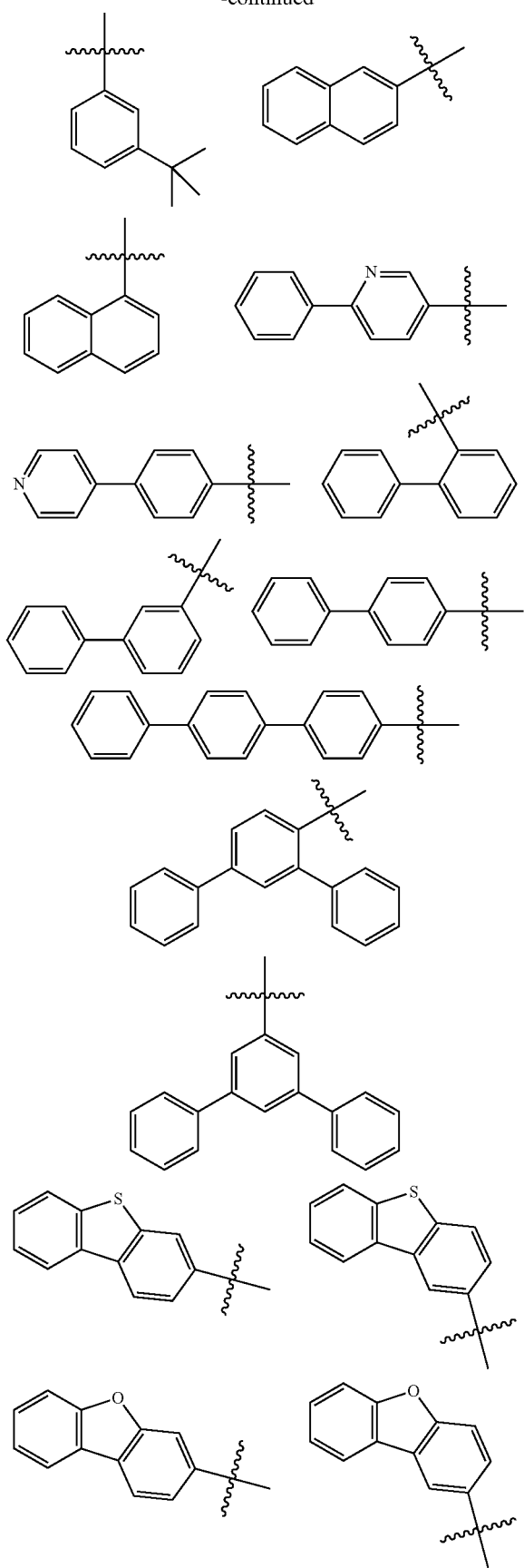
22
-continued
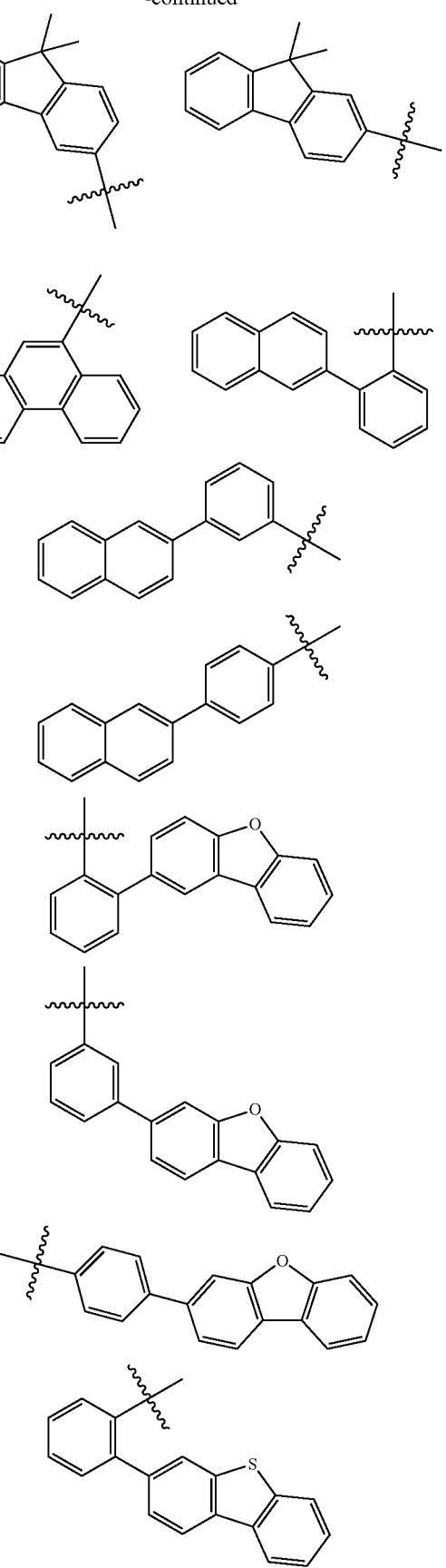

-continued

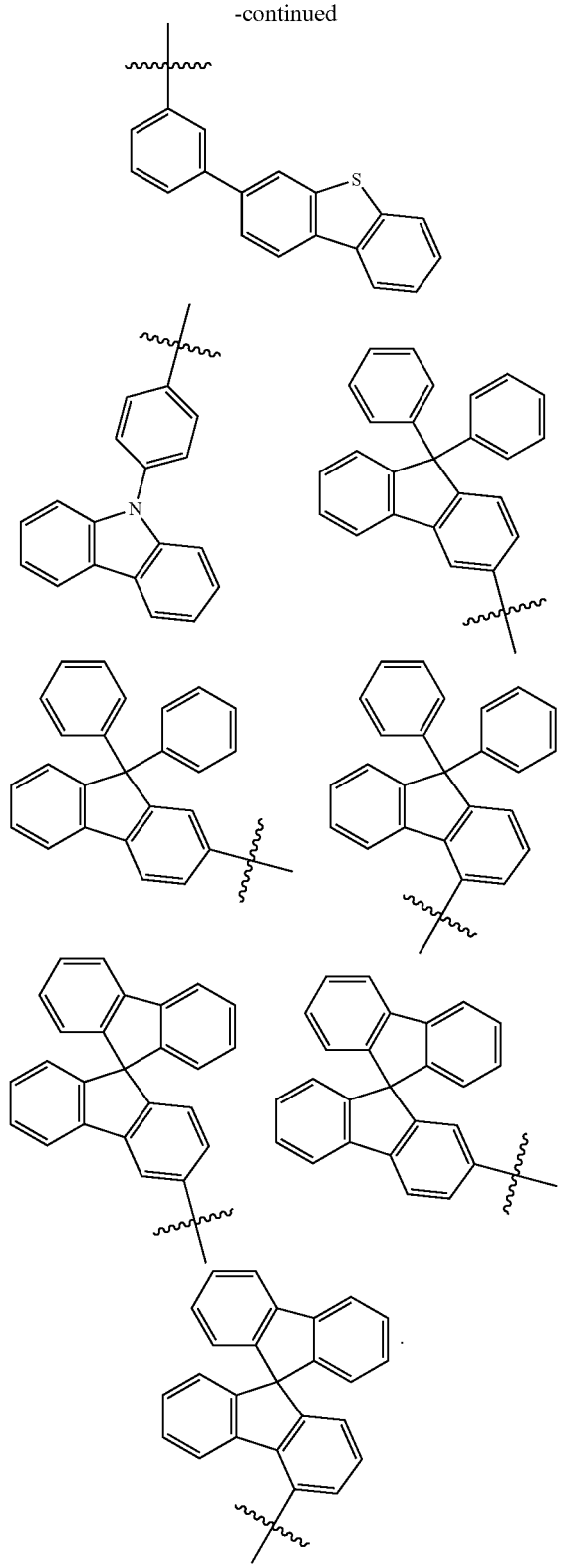

Optionally, Ar₁ and Ar₂ are identical or different and are respectively independently selected from the following substituted or unsubstituted groups: phenyl, naphthalyl, biphenyl, terphenyl, phenanthryl, anthracyl, 9,9-spirobifluorenyl, 9,9-dimethylfluorenyl, pyridyl, carbazolyl, pyrimidinyl, 1,10-phenanthrolinyl, pyridazinyl, triazinyl, quinolinyl, isoquinolinyl, quinazolinyl, pyrazinyl, phenylpyridyl, quinoxyl, pyrenyl, N-phenylcarbazolyl, dibenzofuranyl, or dibenzothienyl. The substitution is substitution with a substituent selected from the following groups: deuterium, fluorine, cyano, trimethylsilyl, methyl, ethyl, isopropyl, tert-butyl, phenyl, naphthalyl, pyridyl, dibenzfurfuranyl, cyclohexanyl, 9,9-dimethylfluorenyl, carbazolyl or dibenzothienyl. When there are multiple substituents, the multiple substituents are identical or different.

Optionally, the nitrogen-containing compound of this application is selected from the group consisting of the following compounds:

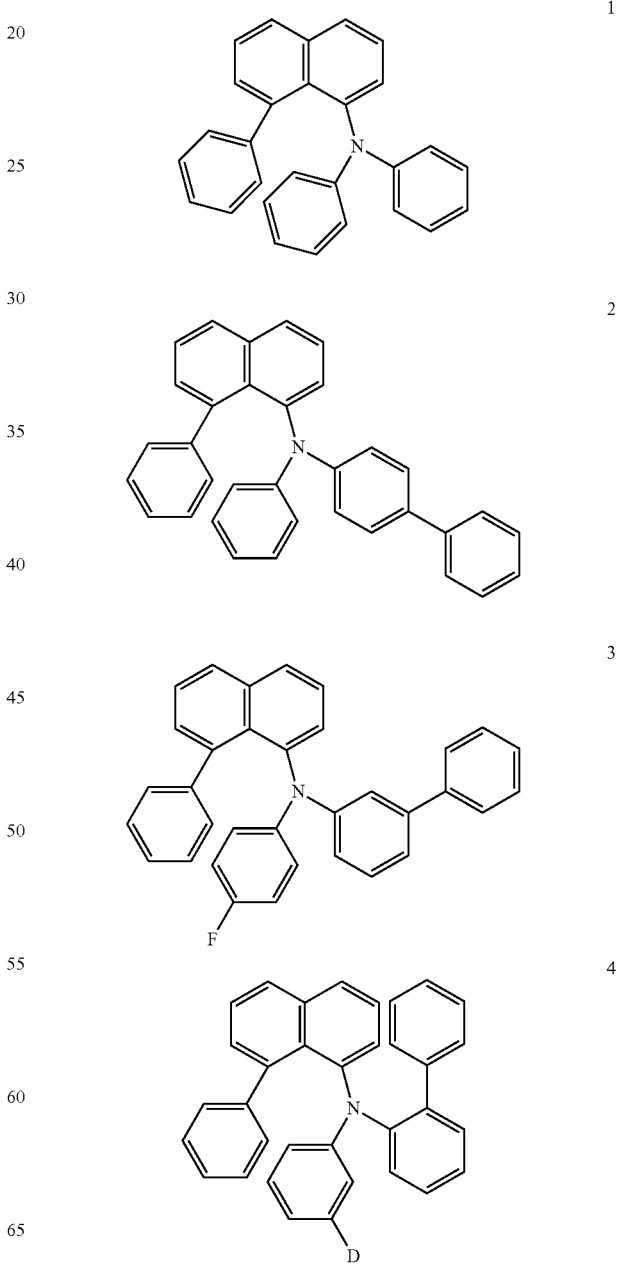

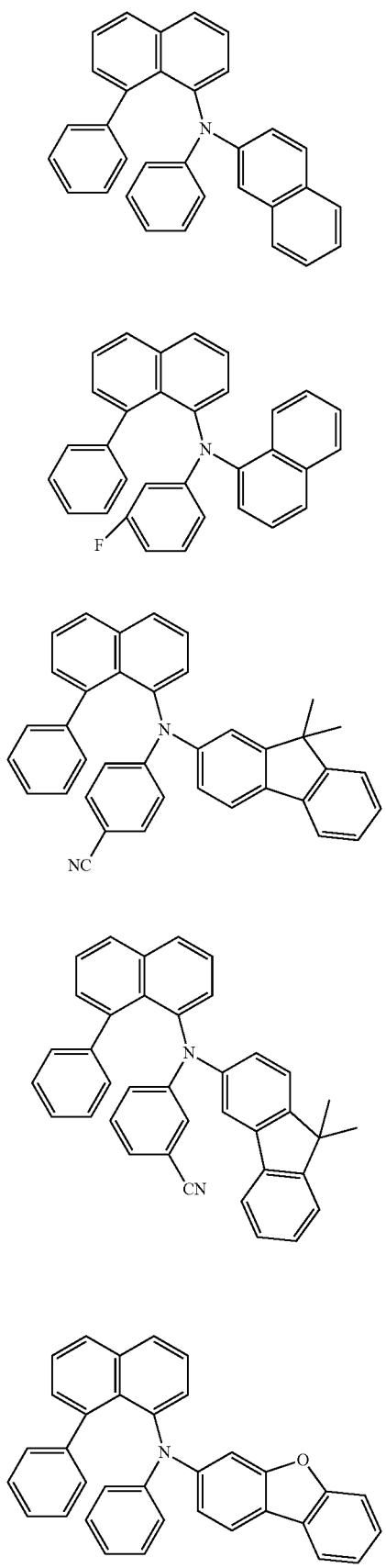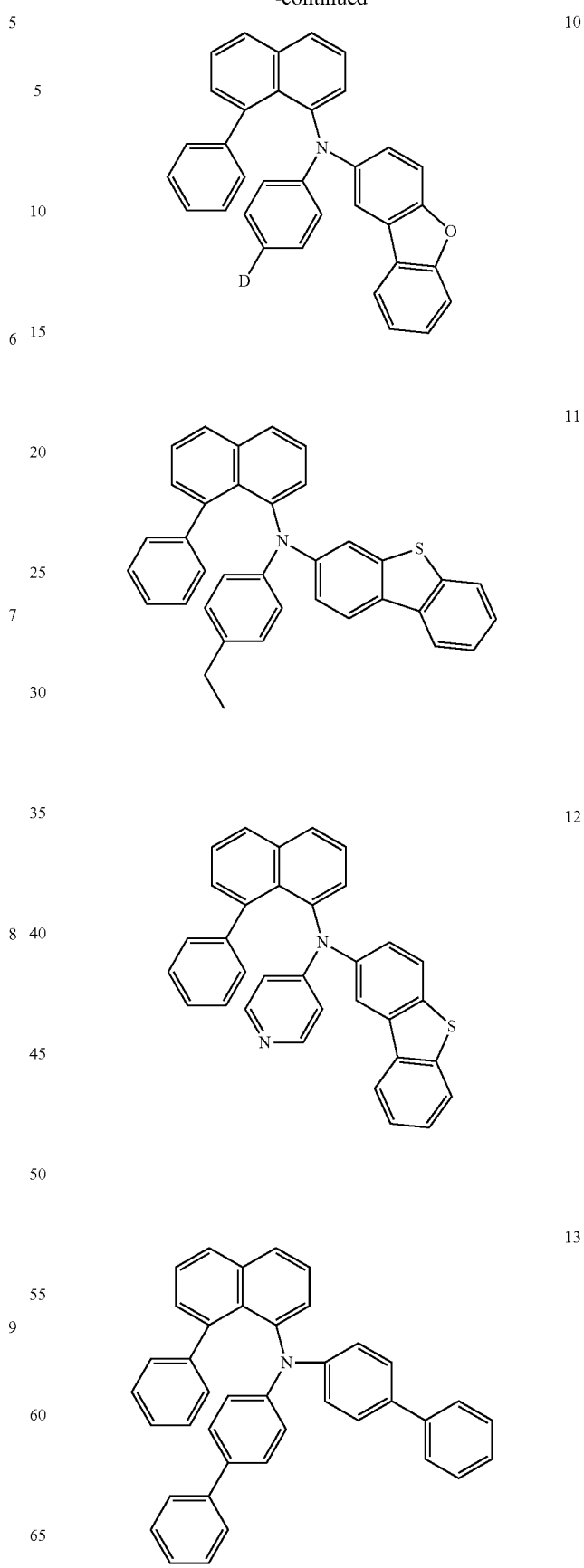

14
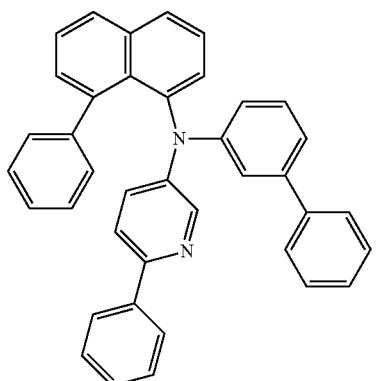
15
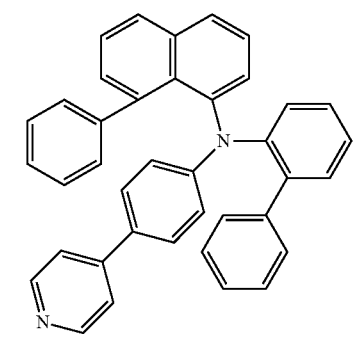
16
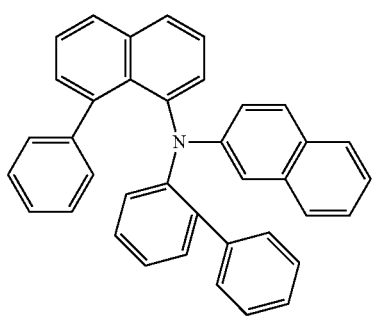
17
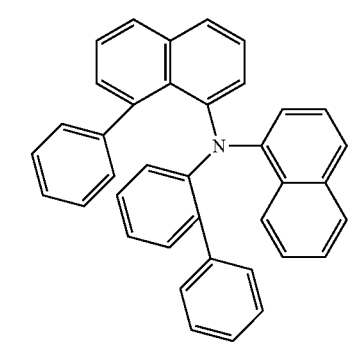
18
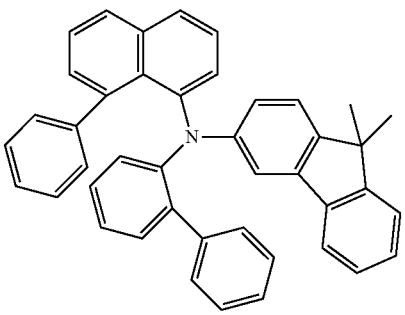
19
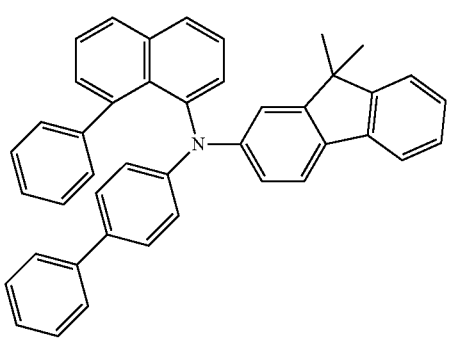
20
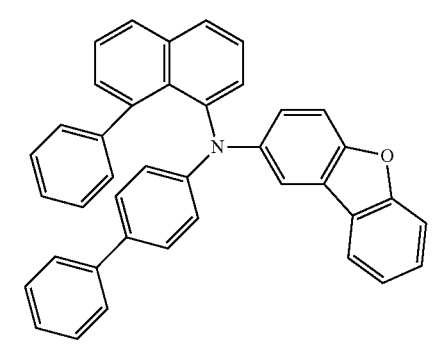
21
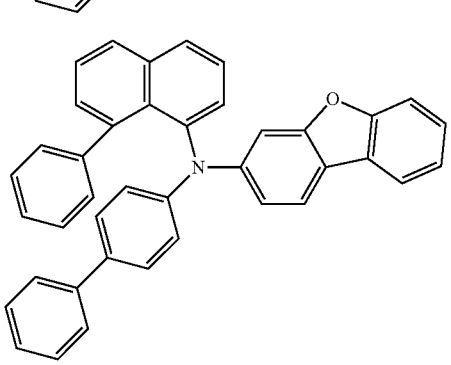
22
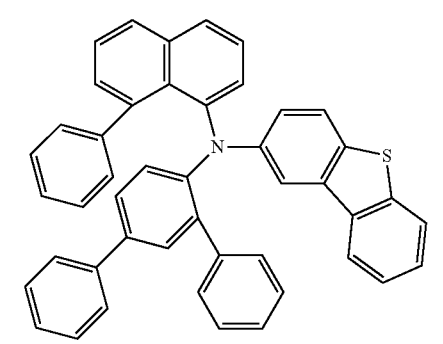

23
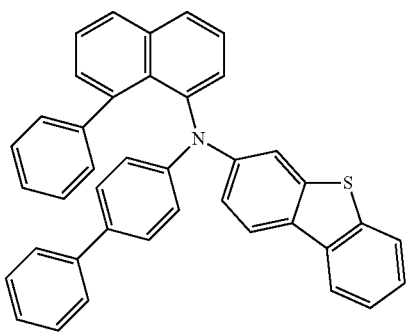
24
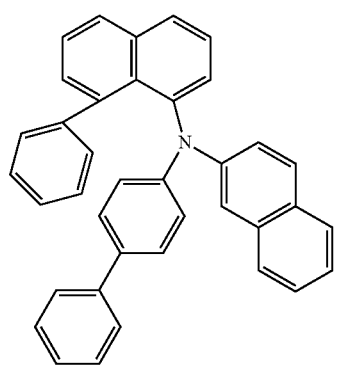
25
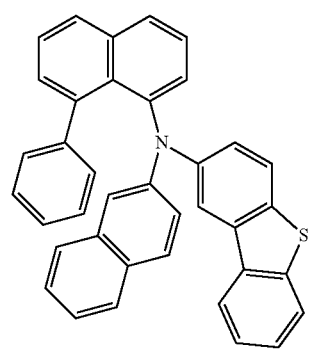
26
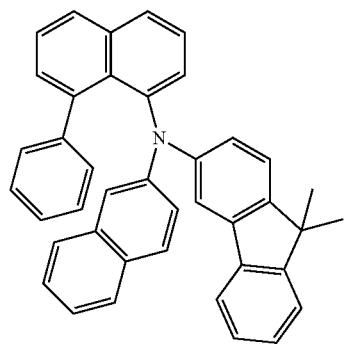
27
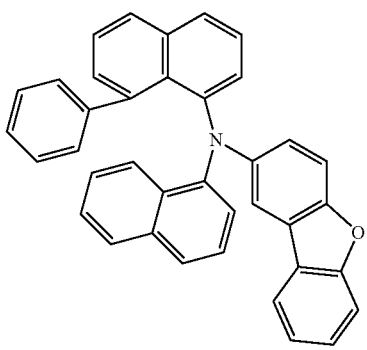
28
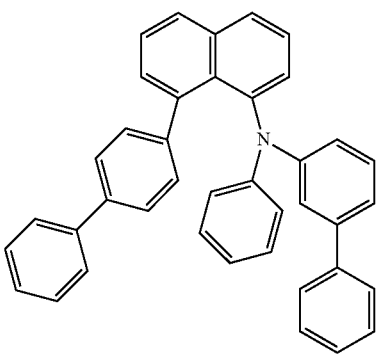
29
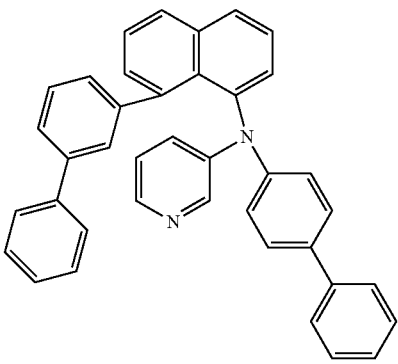
30
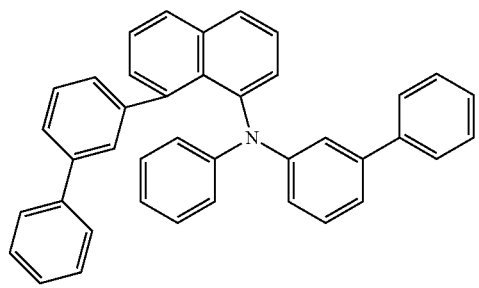

-continued
31
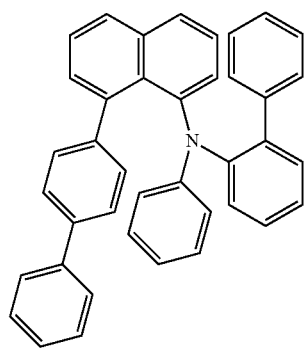
32
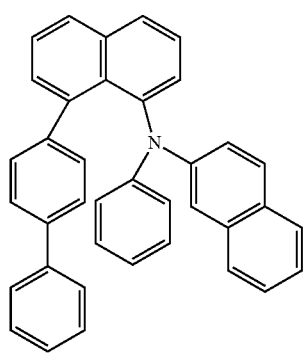
33
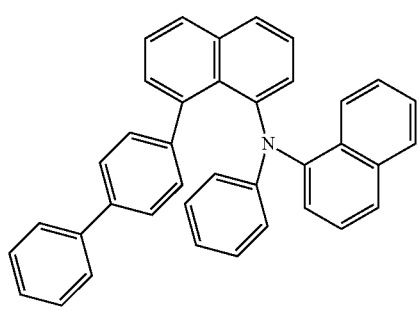
34
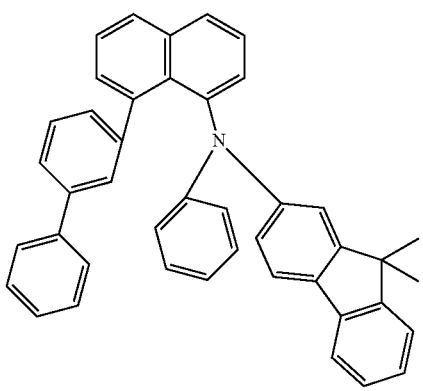
35
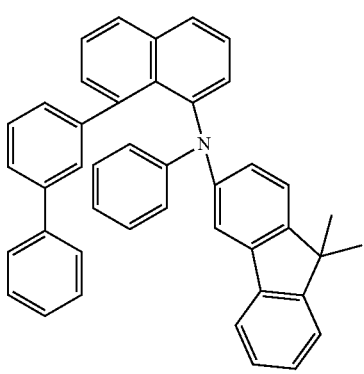
36
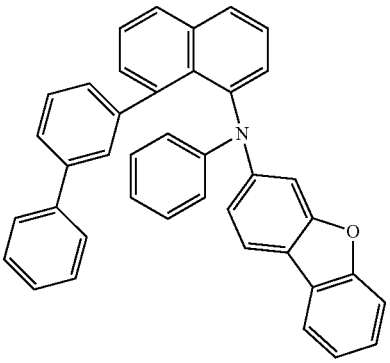
37
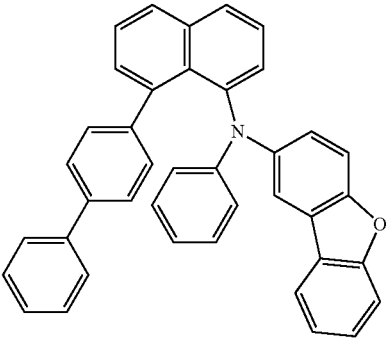
38
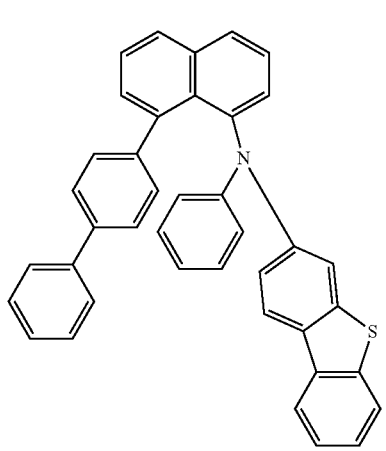

39
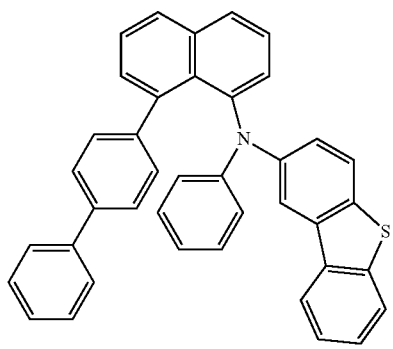
40
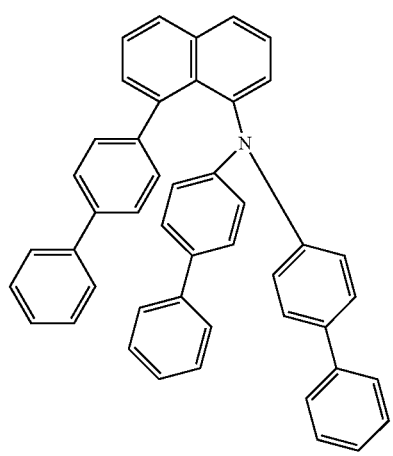
41
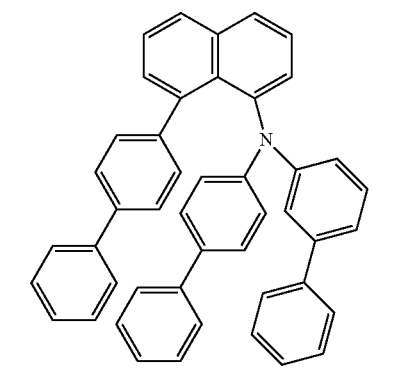
42
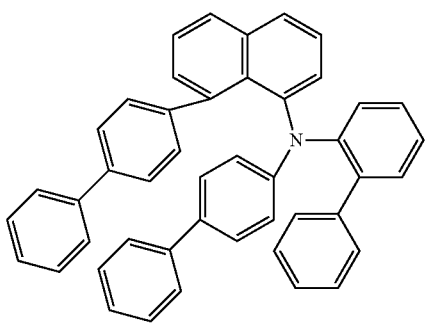
43
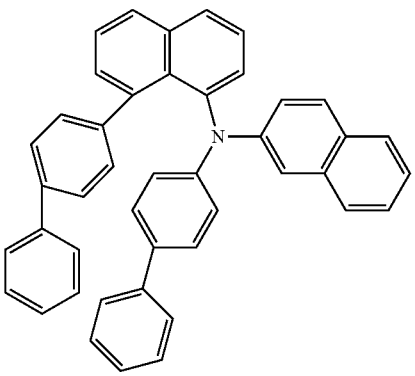
44
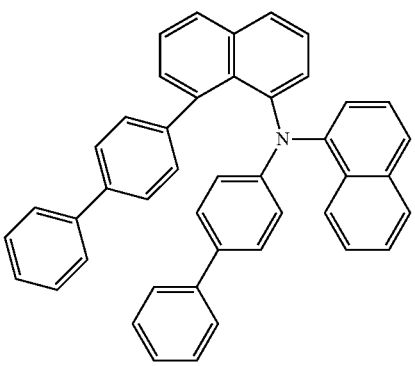
45
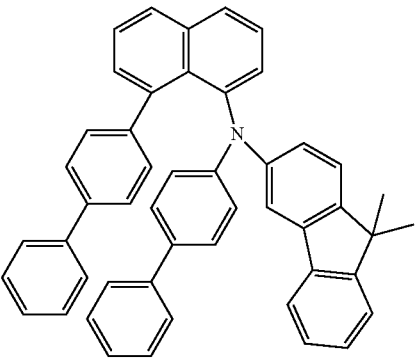
46
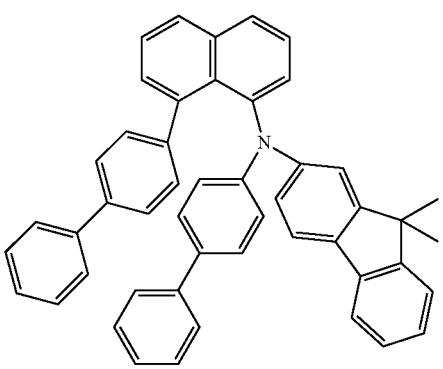

47
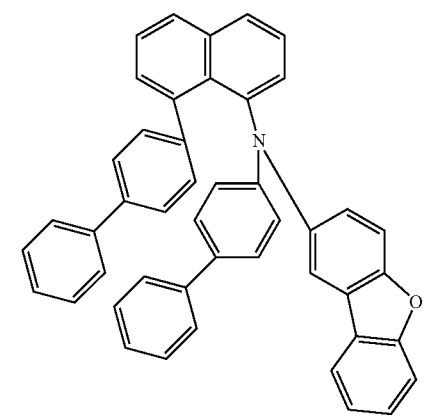
48
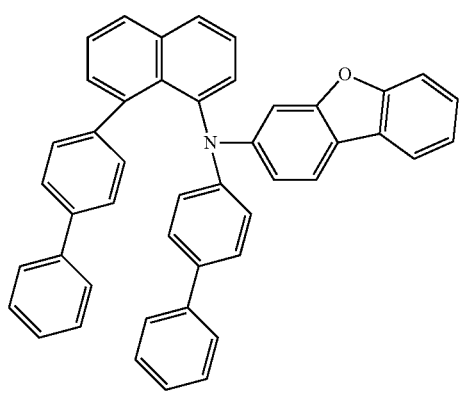
49
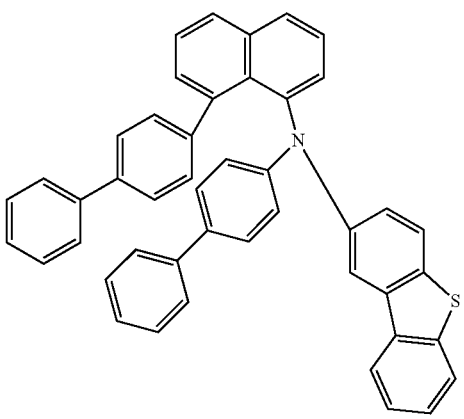
50
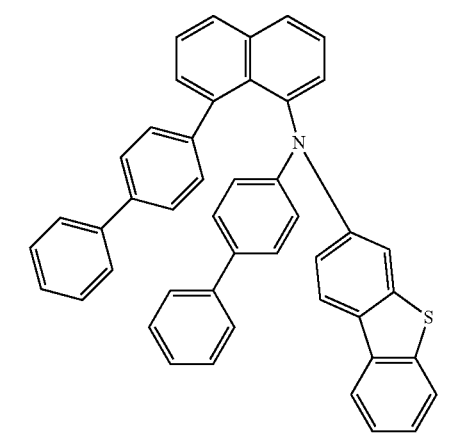
51
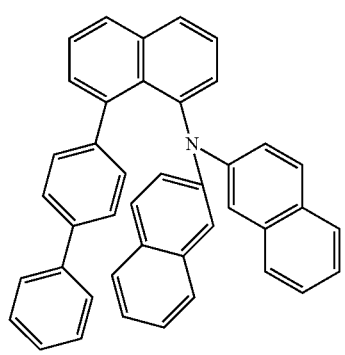
52
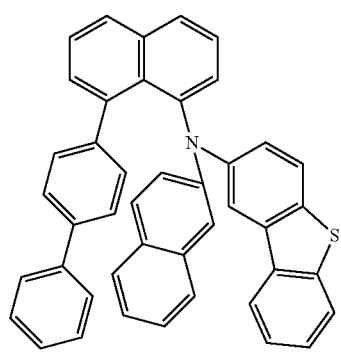
53
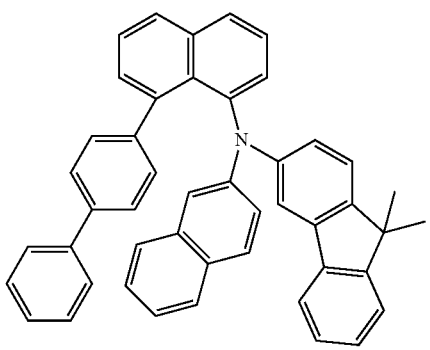
54
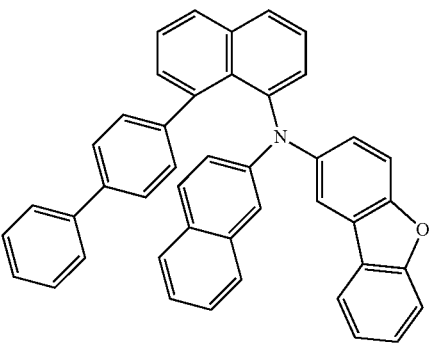

| 37 -continued | 38 -continued |
|---|---|
| 55 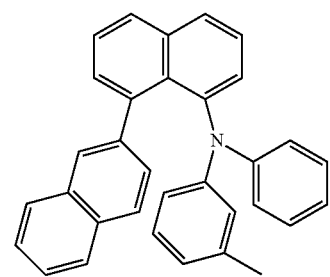 | 60 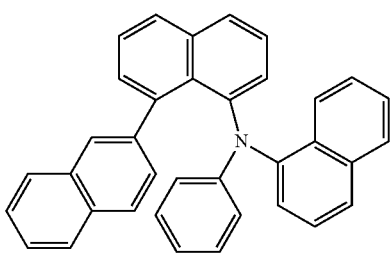 |
| 56 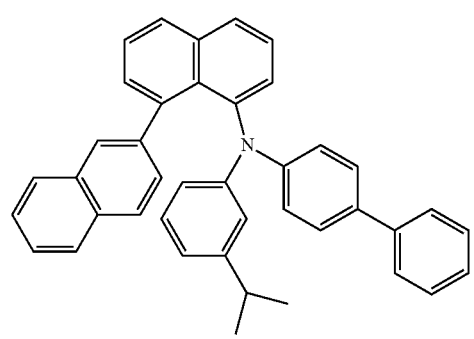 | 61 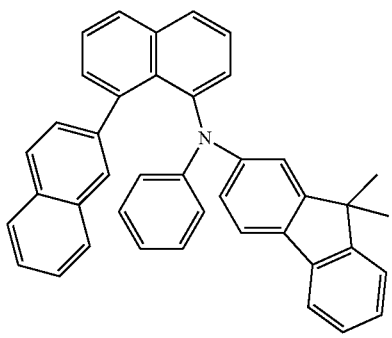 |
| 57 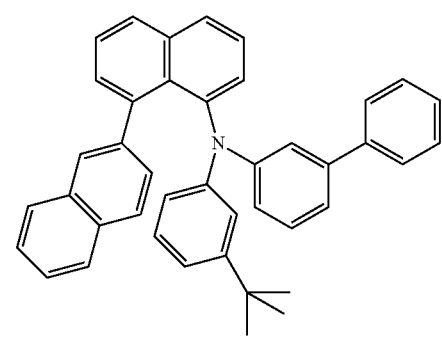 | 62 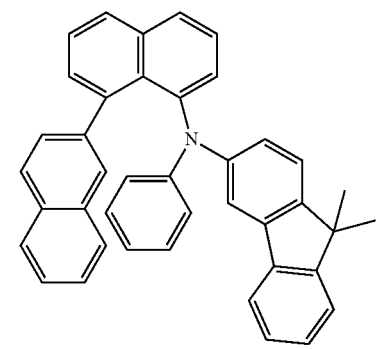 |
| 58 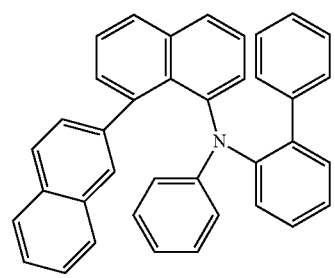 | |
| 59 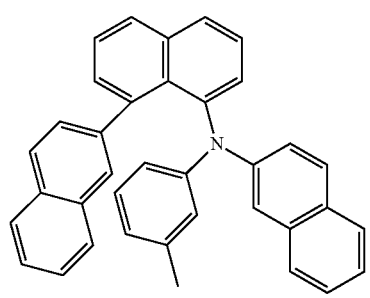 | 63 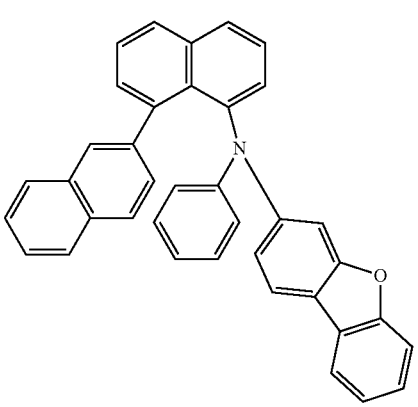 |

64
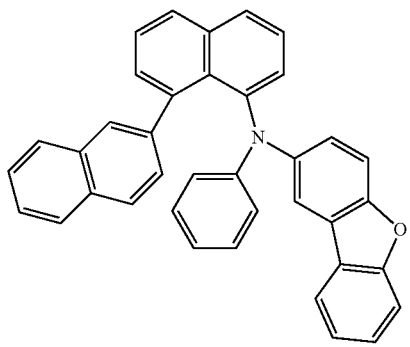
65
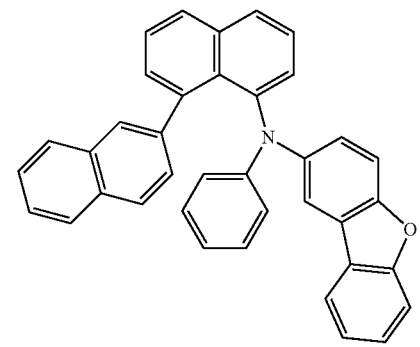
66
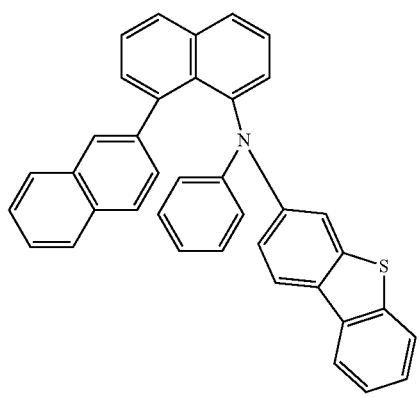
67
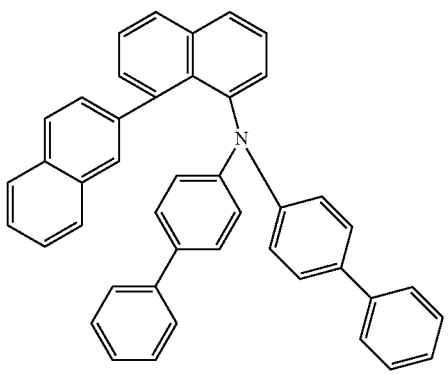
68
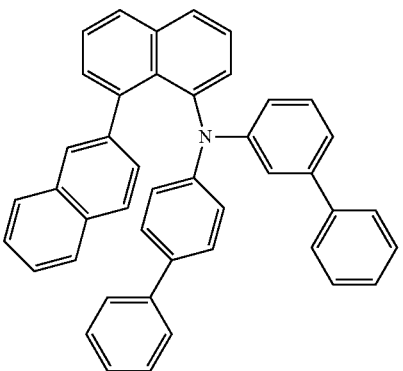
69
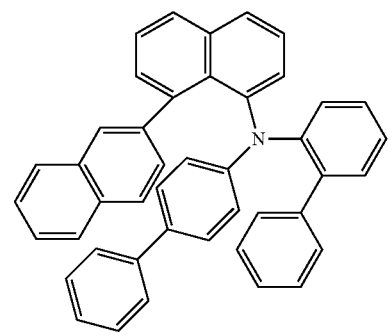
70
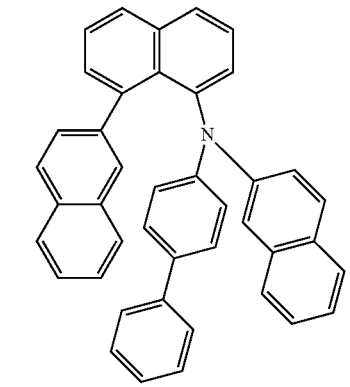
71
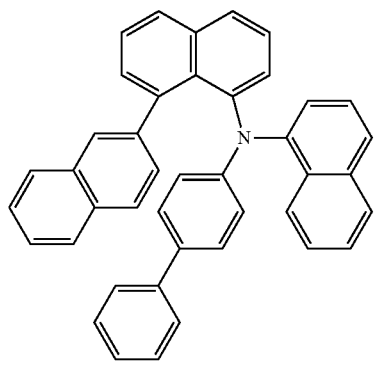

72 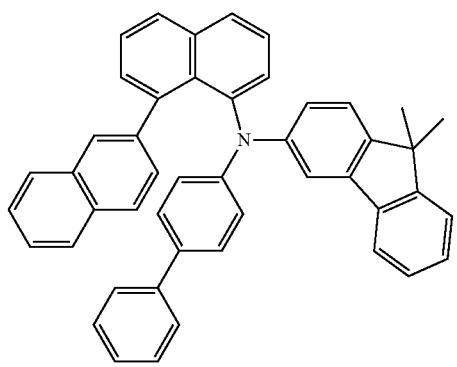
76 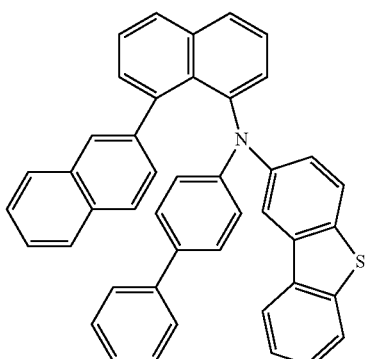
73 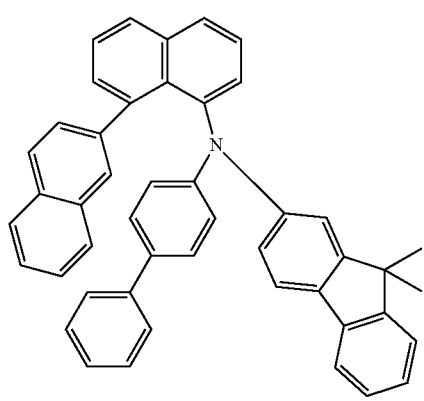
77 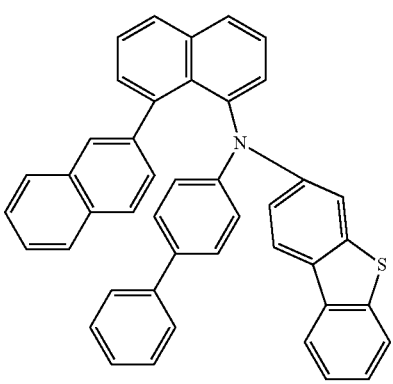
74 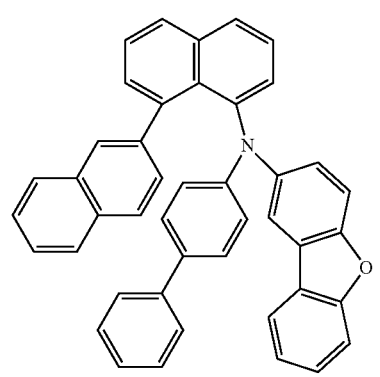
78 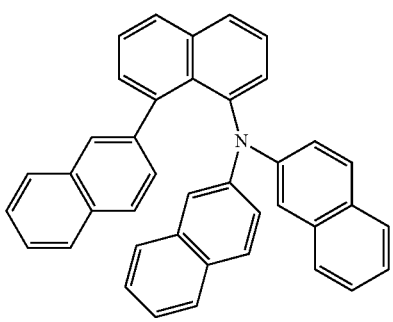
75 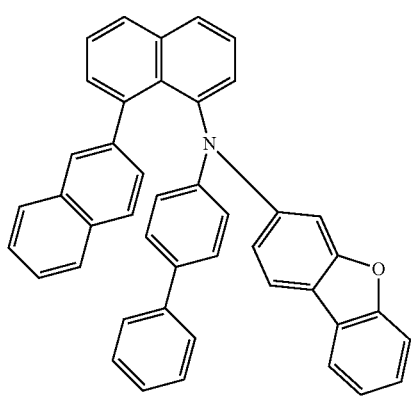
79 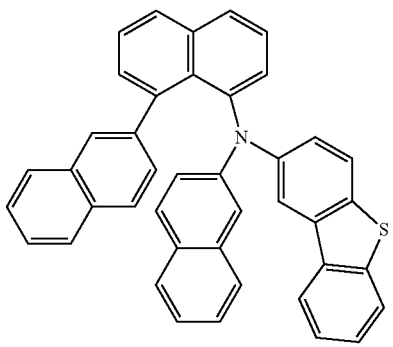

80
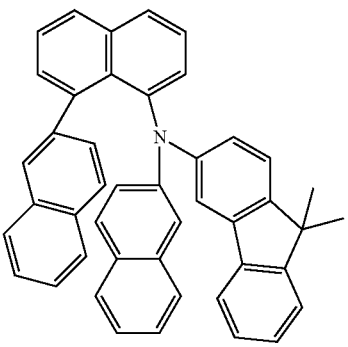
81
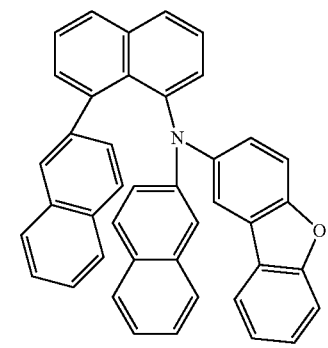
82
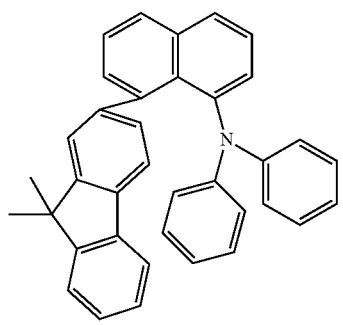
83
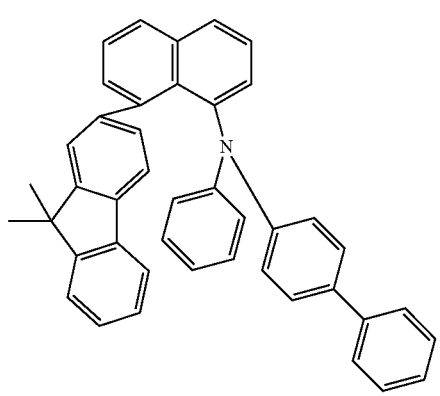
84
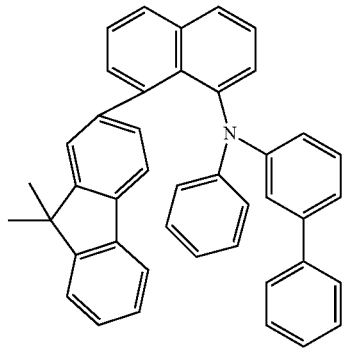
85
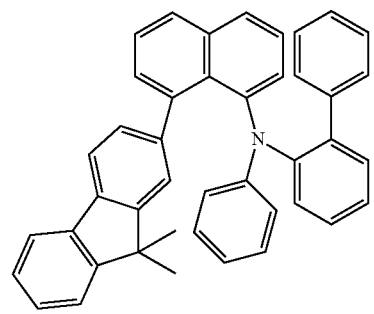
86
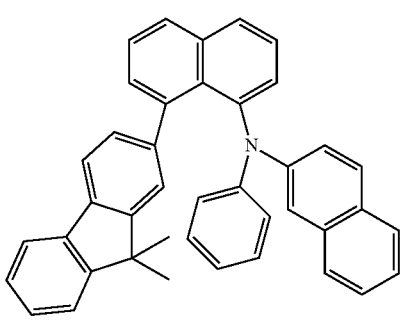
87
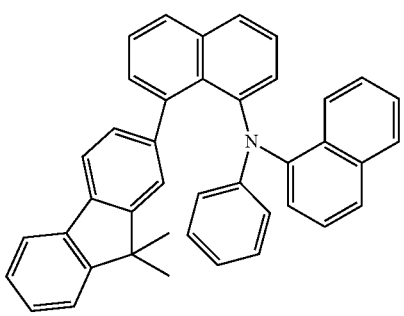
88
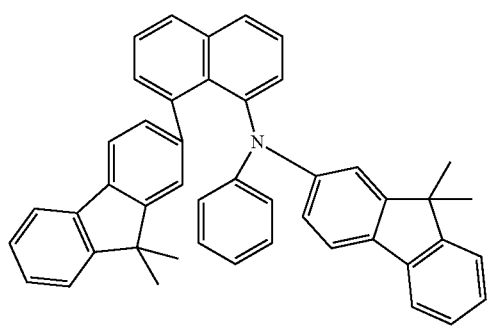

89 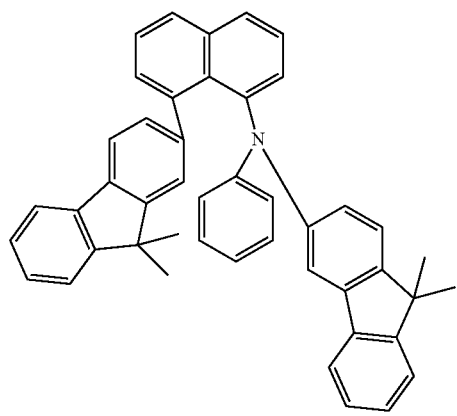
90 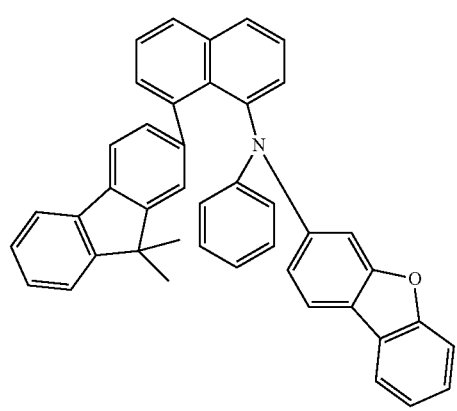
91 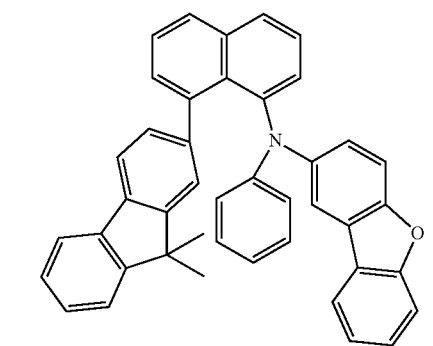
92 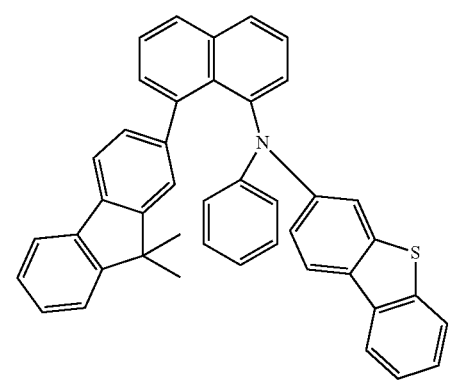
93 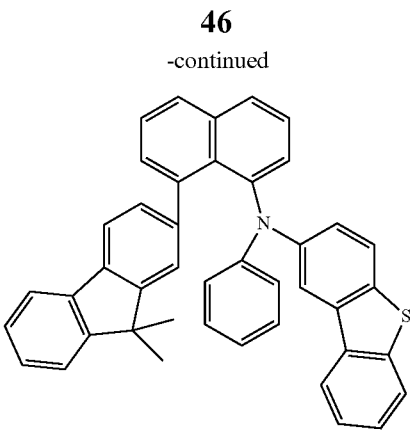
94 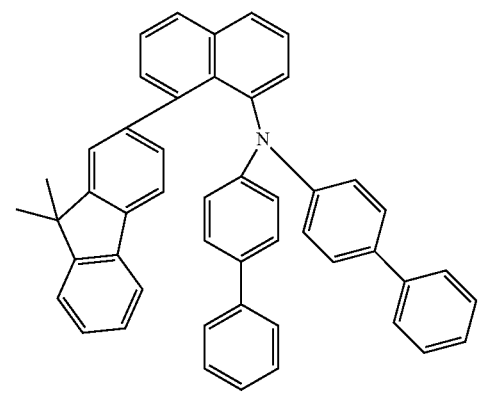
95 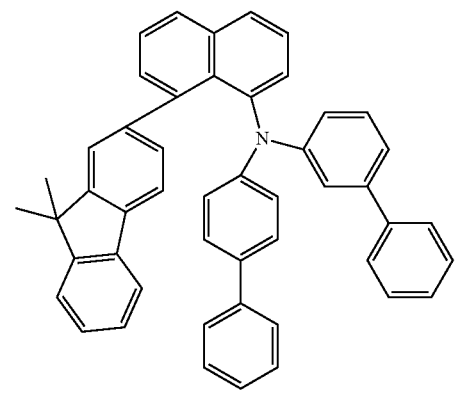
96 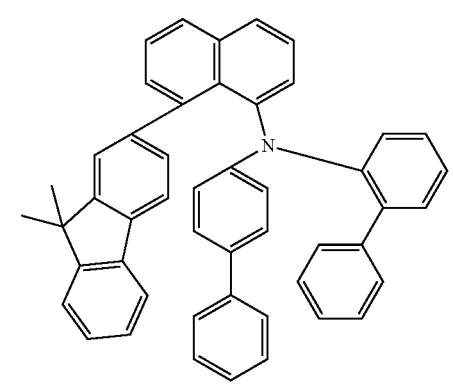

97 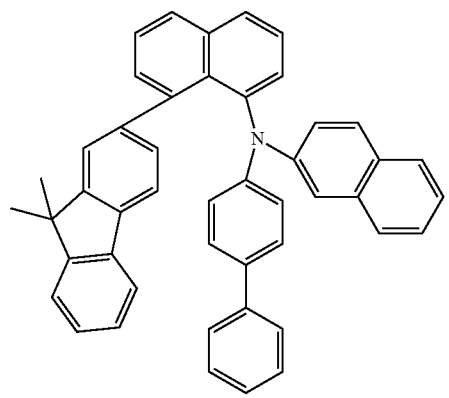
98 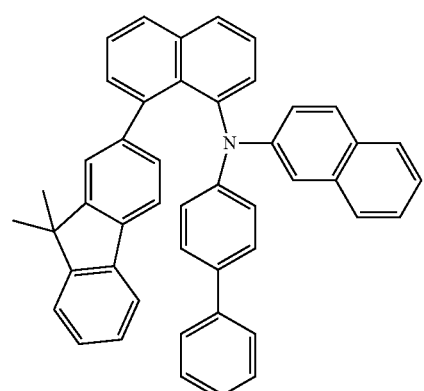
99 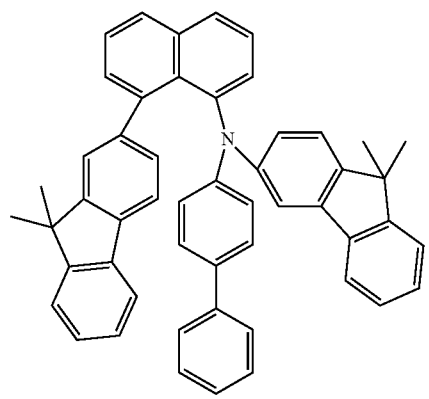
100 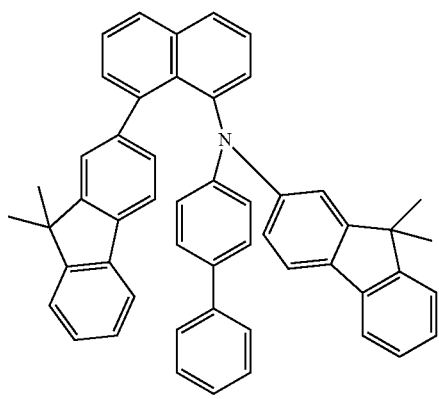
101 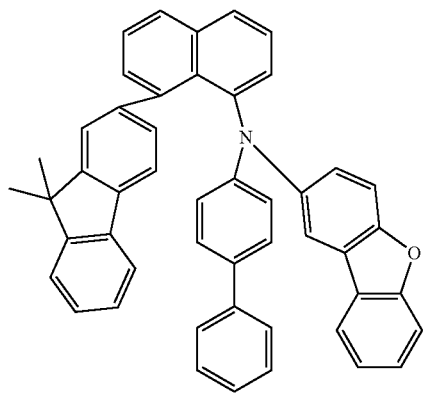
102 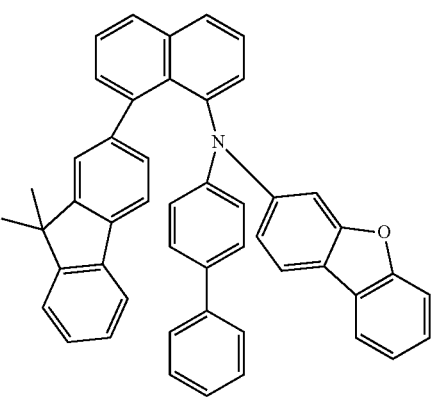
103 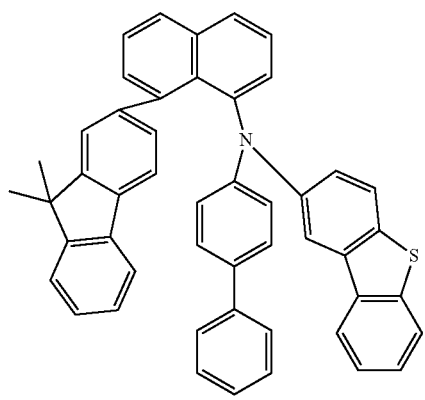
104 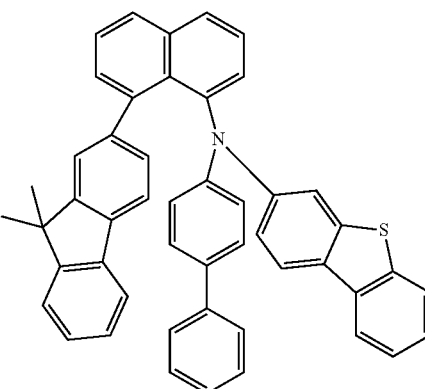

105
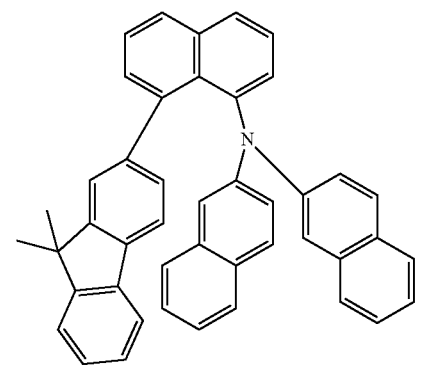
106
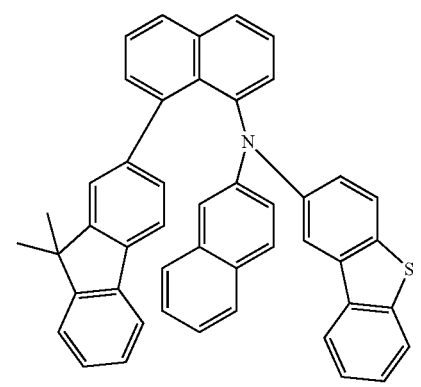
107
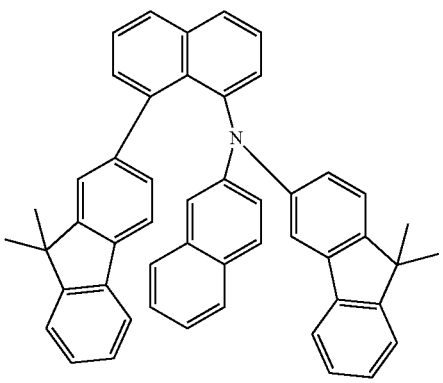
108
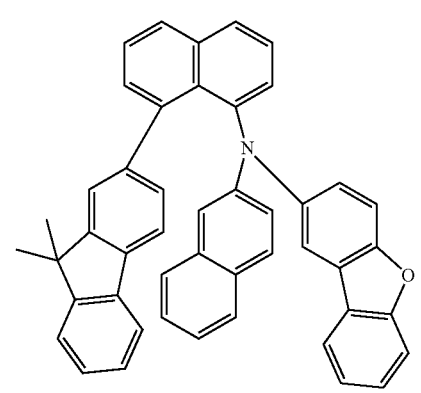
109
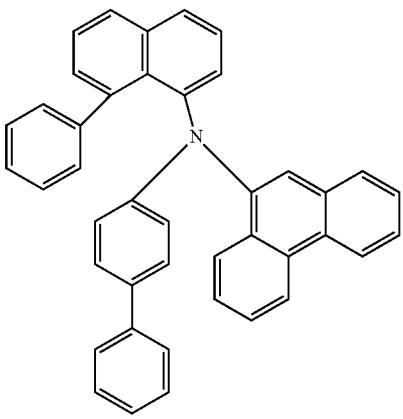
110
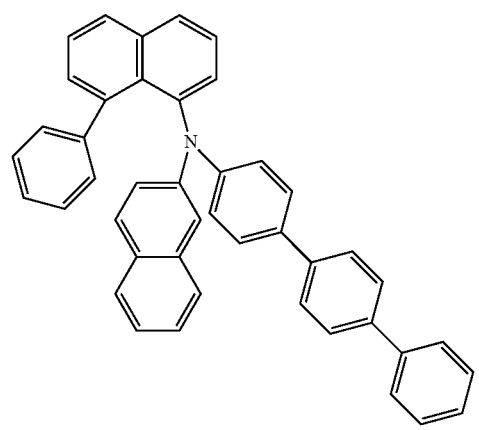
111
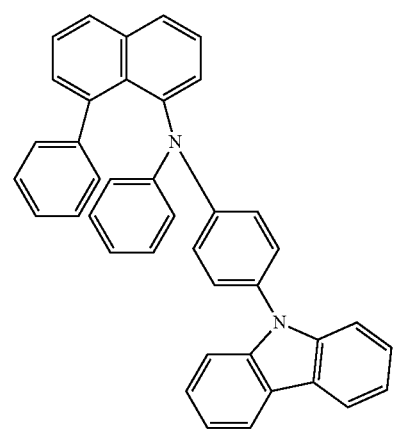

112
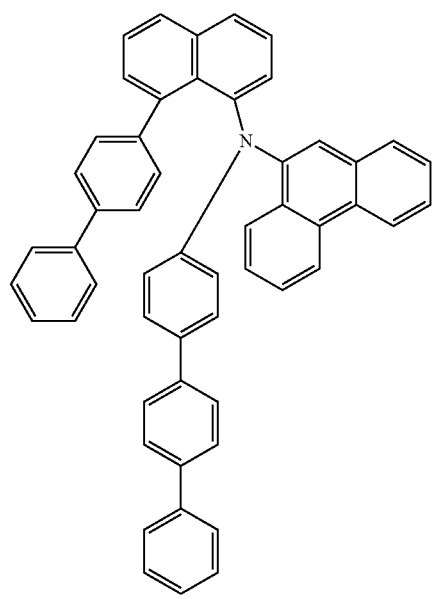
113
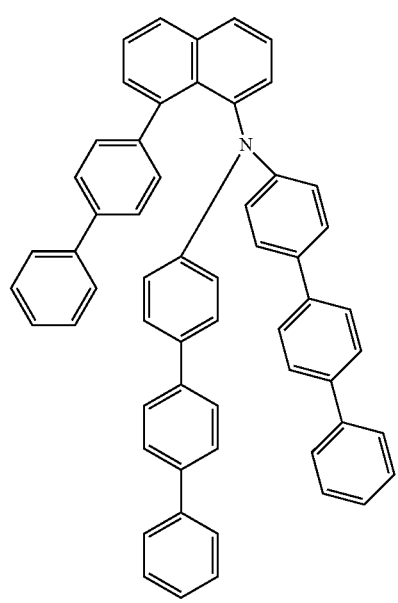
114
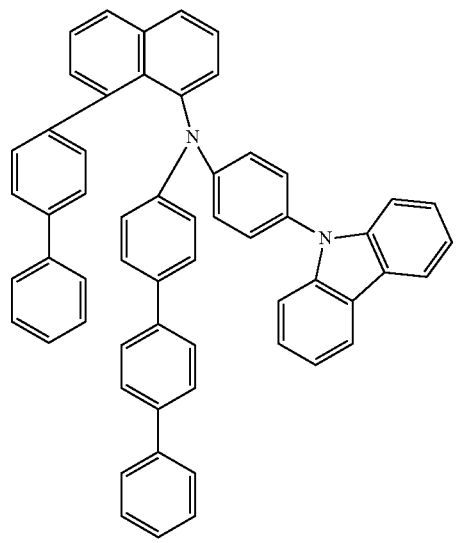
115
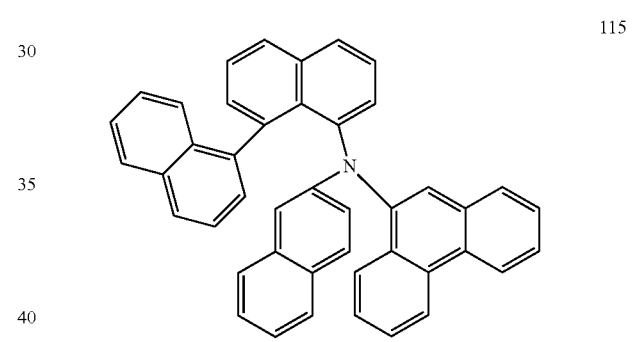
116
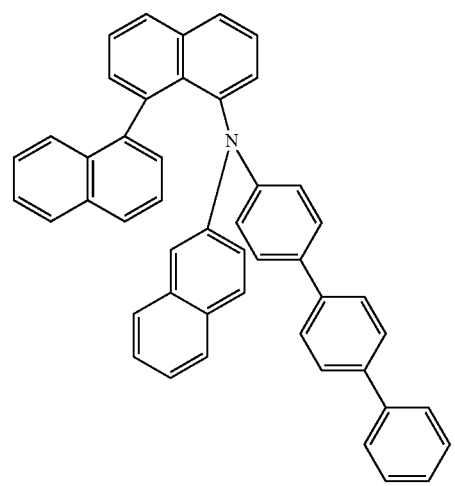

-continued
117
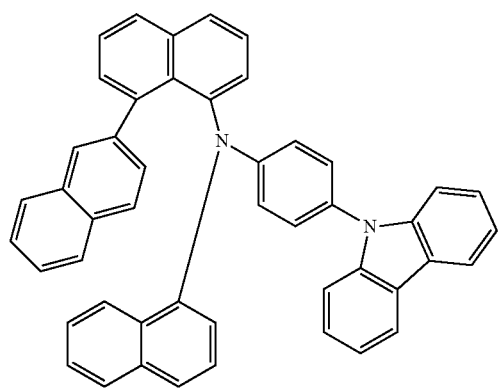
118
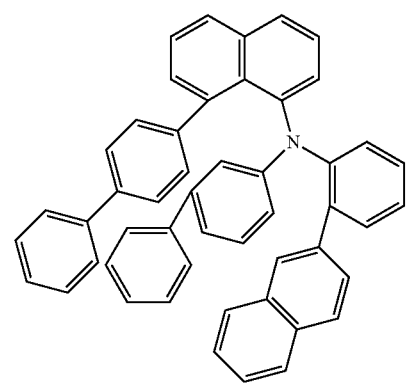
119
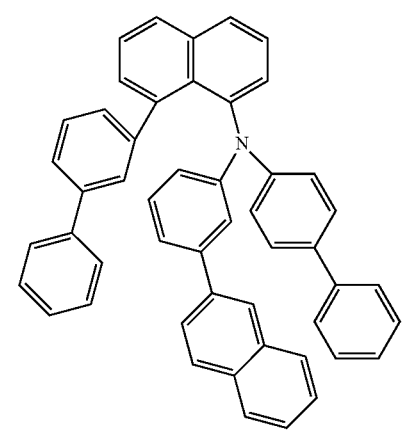
120
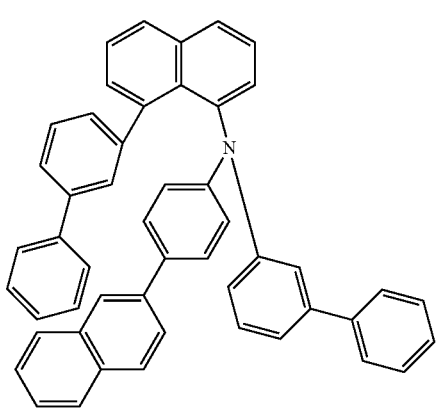
-continued
121
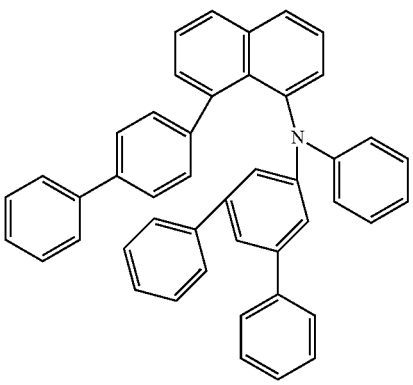
122
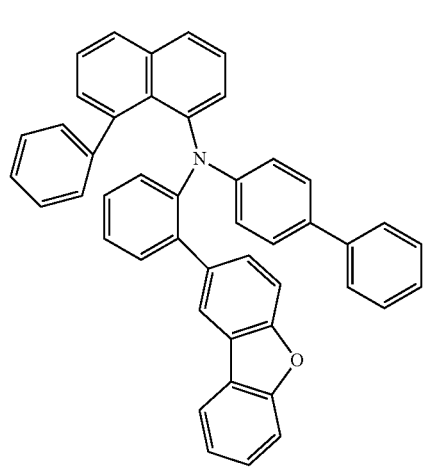
123
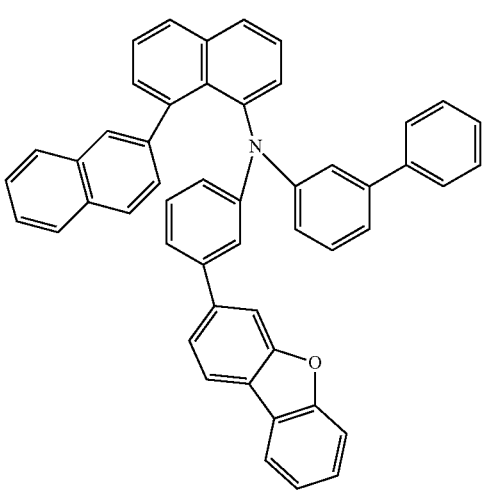

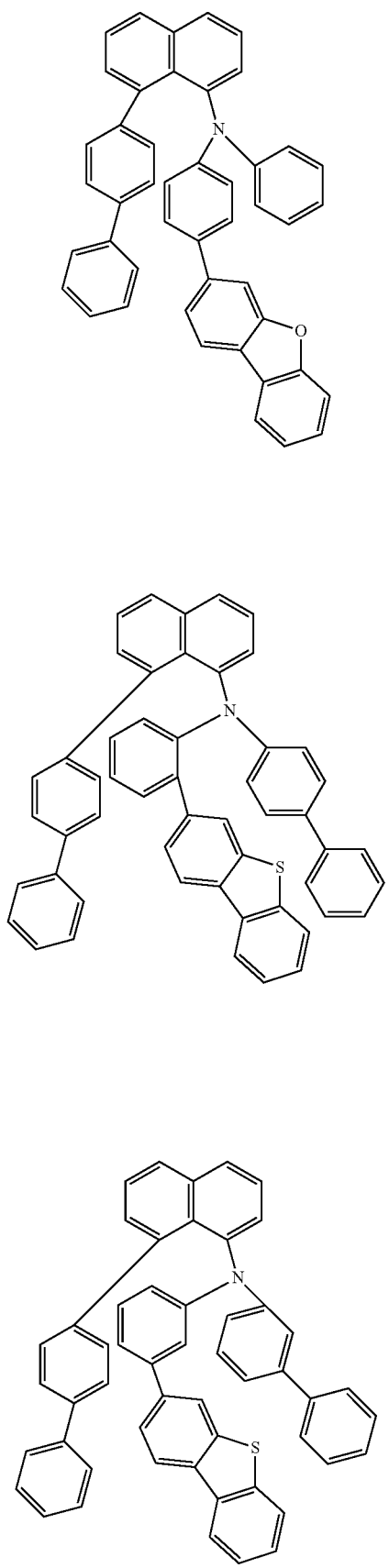
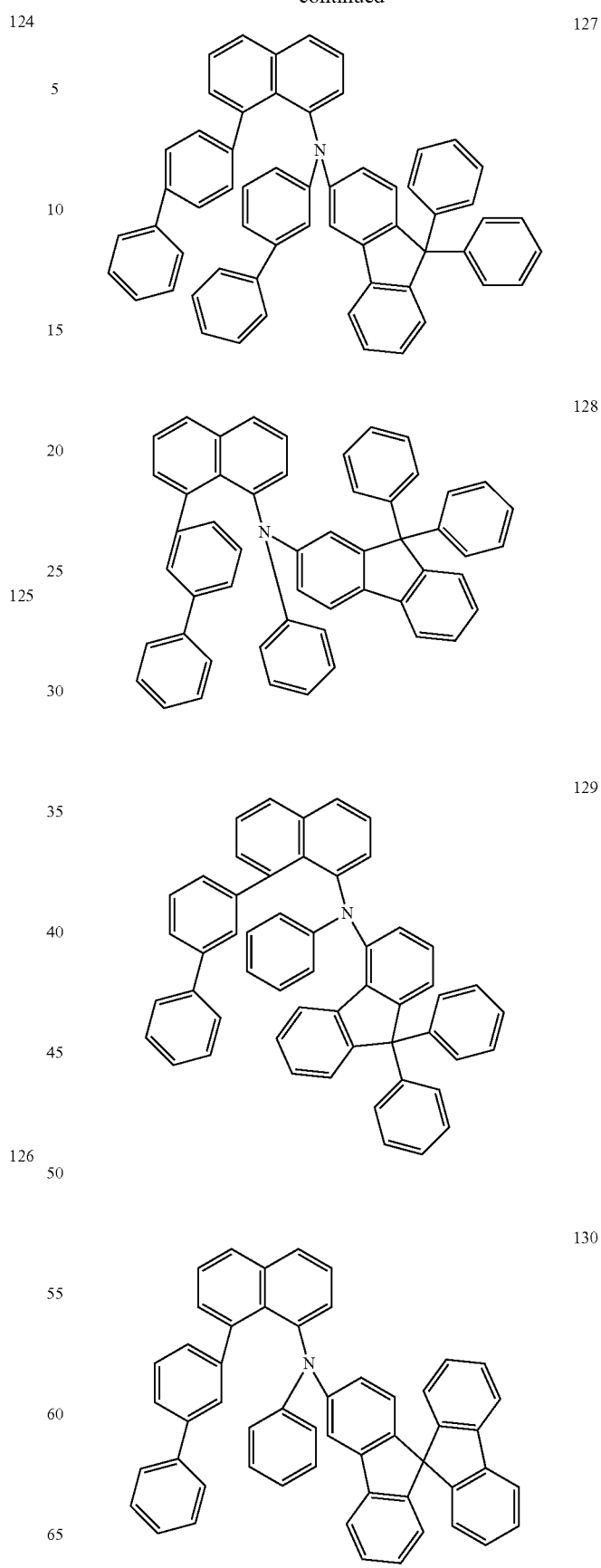

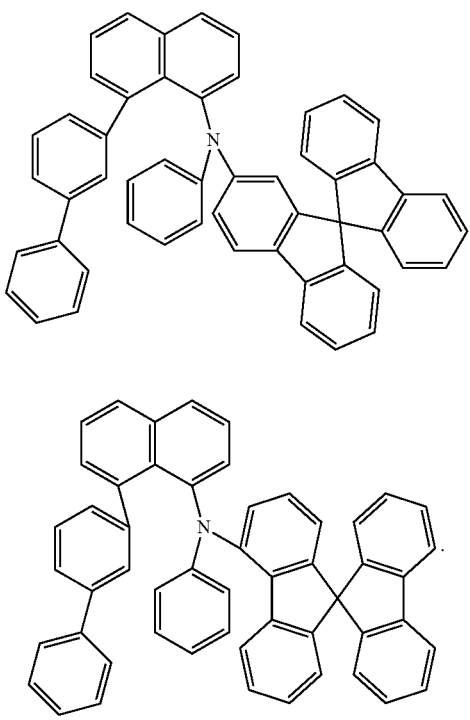

131

132

This application also provides an electronic element configured to implement electrical-to-optical conversion or optical-to-electrical conversion. The electronic element comprises an anode and a cathode disposed oppositely, and a functional layer disposed between the anode and the cathode; the functional layer comprises the nitrogen-containing compound of this application.

For example, the electronic element may be an organic electroluminescent device. Wherein, as shown in FIG. 1, the organic electroluminescent device includes an anode 100 and a cathode 200 disposed oppositely, and a functional layer 300 disposed between the anode 100 and the cathode 200; the functional layer 300 comprises the nitrogen-containing compound provided in this application.

Optionally, the nitrogen-containing compound provided in this application may be used for forming at least one organic thin layer in the functional layer 300 to improve the life and efficiency performance of the organic electroluminescent device and reduce its driving voltage. In some embodiments, it can also improve the electrochemical stability and thermal stability of the organic electroluminescent device, and improve the performance uniformity of mass-produced organic electroluminescent devices.

Optionally, the functional layer 300 includes a hole transport layer 320, and the hole transport layer 320 includes the nitrogen-containing compound provided in this application. Where, the hole transport layer 320 may consist of the nitrogen-containing compound provided in this application, or may consist of the nitrogen-containing compound provided in this application and other materials.

Optionally, the hole transport layer 320 includes a first hole transport layer 321 and a second hole transport layer 322, and the first hole transport layer 321 is disposed on a surface of the second hole transport layer 322 close to the anode 100; the first hole transport layer 321 or the second hole transport layer 322 includes the nitrogen-containing compound provided in this application. Wherein, one of the first hole transport layer 321 or the second hole transport layer 322 includes the nitrogen-containing compound provided in this application, or both the first hole transport layer 321 and the second hole transport layer 322 include the nitrogen-containing compound provided in this application. It can be understood that the first hole transport layer 321 or the second hole transport layer 322 may also comprise other materials, or may not comprise other materials. It can be understood that, in another embodiment of this application, the second hole transport layer 322 may serve as an electron blocking layer of the organic electroluminescent device.

In an embodiment of this application, as shown in FIG. 1, the organic electroluminescent device may include an anode 100, a first hole transport layer 321, a second hole transport layer 322, an organic light-emitting layer 330, an electron transport layer 340, and a cathode 200 arranged in sequence. The nitrogen-containing compound provided in this application may be applied in the first hole transport layer 321 or the second hole transport layer 322 of the organic electroluminescent device to effectively improve the hole characteristic of the organic electroluminescent device. Where the hole characteristic means that the hole formed in the anode 100 is easily injected into the organic light-emitting layer 330 and is transported in the organic light-emitting layer 330 according to the conduction characteristic of the HOMO level.

Optionally, the anode 100 includes the following anode materials, which is preferably a material having a large work function that facilitates injection of holes into the functional layer. Specific examples of the anode material include, but are not limited to: a metal, such as nickel, platinum, vanadium, chromium, copper, zinc or gold, or an alloy thereof, a metal oxide, such as zinc oxide, indium oxide, indium tin oxide (ITO) or indium zinc oxide (IZO); a combination of a metal and an oxide, such as ZnO:Al or $SnO_2$:Sb; or a conductive polymer, such as poly(3-methylthiophene), poly [3,4-(ethylene-1,2-dioxy)thiophene] (PEDT), polypyrrole or polyaniline. Preferably, the organic electroluminescent device includes a transparent electrode containing indium tin oxide (ITO) as the anode.

Optionally, the organic light-emitting layer 330 may consist of a single light-emitting material, or may include a host material and a guest material. Optionally, the organic light-emitting layer 330 consists of a host material and a guest material. The holes injected into the organic light-emitting layer 330 and the electrons injected into the organic light-emitting layer 330 can recombine in the organic light-emitting layer 330 to form excitons. The excitons transfer energy to the host material, and the host material transfers energy to the guest material to enable the guest material to emit light.

The host material of the organic light-emitting layer 330 may be a metal chelated oxinoid compound, a bis-styryl derivative, an aromatic amine derivative, a dibenzofuran derivative or other types of materials, and is not particularly limited in this disclosure. In an embodiment of this disclosure, the host material of the organic light-emitting layer 330 may be CBP. In another embodiment of this disclosure, the host material of the organic light-emitting layer 330 may be α,β-ADN.

The guest material of the organic light-emitting layer 330 may be a compound having a condensed aryl ring or a derivative thereof, a compound having a heteroaryl ring or a derivative thereof, an aromatic amine derivative or other materials, and is not particularly limited in this application. In an embodiment of this disclosure, the guest material of the organic light-emitting layer 330 may be $Ir(piq)_2(acac)$. In another embodiment of this disclosure, the guest material of the organic light-emitting layer 330 may be BD-1.

The electron transport layer 340 may be a single-layer structure or a multilayer structure, and may include one or more electron transport materials. The electron transport materials may be selected from benzimidazole derivatives, oxadiazole derivatives, quinoxaline derivatives or other electron transport materials, and are not particularly limited in this disclosure. For example, in an embodiment of this disclosure, the electron transport layer 340 may consist of DBimiBphen and LiQ.

Optionally, the cathode 200 includes the following cathode materials, which are materials with a small work function that facilitate injection of electrons into the functional layer. Specific examples of the cathode materials include, but are not limited to: a metal, such as magnesium, calcium, sodium, potassium, titanium, indium, yttrium, lithium, gadolinium, aluminum, silver, tin, or lead, or an alloy thereof, or a multilayer material, such as LiF/Al, Liq/Al, LiO$_2$/Al, LiF/Ca, LiF/Al or BaF$_2$/Ca. Preferably, the organic electroluminescent device includes a metal electrode containing aluminum as the cathode.

Optionally, as shown in FIG. 1, a hole injection layer 310 may further be disposed between the anode 100 and the first hole transport layer 321 to enhance the ability to inject holes into the first hole transport layer 321. The material of the hole injection layer 310 may be selected from a benzidine derivative, a starburst arylamine compound, a phthalocyanine derivative or other materials, which are not particularly limited in this application. In an embodiment of this disclosure, the hole injection layer 310 may consist of m-MTDATA.

Optionally, as shown in FIG. 1, an electron injection layer 350 may further be disposed between the cathode 200 and the electron transport layer 340 to enhance the ability to inject electrons into the electron transport layer 340. The electron injection layer 350 may include an inorganic material, such as an alkali metal sulfide or an alkali metal halide, or may include a complex of an alkali metal and an organic substance. In an embodiment of this disclosure, the electron injection layer 350 may include Yb.

Optionally, an electron injection layer 350 may further be disposed between the cathode 200 and the electron transport layer 340.

Figure 3:
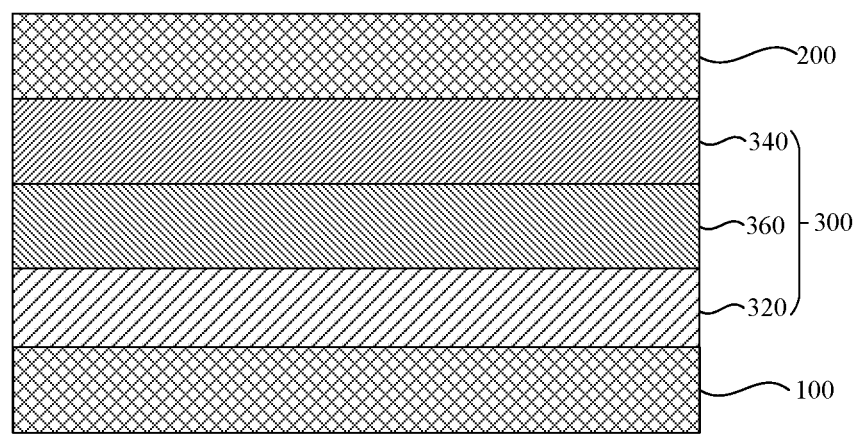
FIG. 3 is a schematic structural diagram of a photoelectric conversion device according to an embodiment of this application.

For another example, the electronic element may be a photoelectric conversion device, As shown in FIG. 3, the photoelectric conversion device may include an anode 100 and a cathode 200 disposed oppositely, and a functional layer 300 disposed between the anode 100 and the cathode 200. The functional layer 300 comprises the nitrogen-containing compound of this application.

Optionally, the nitrogen-containing compound provided in this application may be used for forming at least one organic thin layer in the functional layer 300 to improve the performance of the photoelectric conversion device, especially to increase the life of the photoelectric conversion device, increase the open circuit voltage of the photoelectric conversion device, or increase the uniformity and stability of performance of mass-produced photoelectric conversion devices.

Optionally, the functional layer 300 includes a hole transport layer 320, and the hole transport layer 320 includes the nitrogen-containing compound of this application. Where the hole transport layer 320 may consist of the nitrogen-containing compound provided in this application, or may consist of the nitrogen-containing compound provided in this application and other materials.

Optionally, the hole transport layer 320 comprises a first hole transport layer 321 and a second hole transport layer 322 (as an electron blocking layer of the photoelectric conversion device), and the first hole transport layer 321 is disposed on a surface of the second hole transport layer 322 close to the anode 100. The first hole transport layer 321 or the second hole transport layer 322 comprises the nitrogen-containing compound provided in this application. One of the first hole transport layer 321 or the second hole transport layer 322 comprises the nitrogen-containing compound provided in this application, or both the first hole transport layer 321 and the second hole transport layer 322 comprise the nitrogen-containing compound provided in this application. It can be understood that the first hole transport layer 321 or the second hole transport layer 322 may also comprise other materials, or may not contain other materials.

Optionally, the hole transport layer 320 may further include an inorganic doping material to improve the hole transport performance of the hole transport layer 320.

In an embodiment of this application, as shown in FIG. 3, the photoelectric conversion device may include an anode 100, a first hole transport layer 321, a second hole transport layer 322 (as an electron blocking layer of the photoelectric conversion device), an photoelectric conversion layer 360 as an energy conversion layer, an electron transport layer 340, and a cathode 200 stacked in sequence.

Optionally, the photoelectric conversion device may be a solar cell, especially an organic thin film solar cell. For example, in an embodiment of this application, the solar cell includes an anode 100, a first hole transport layer 321, a second hole transport layer 322 (as an electron blocking layer of the photoelectric conversion device), an photoelectric conversion layer 360, an electron transport layer 340, and a cathode 200 stacked in sequence. The second hole transport layer 322 includes the nitrogen-containing compound of this application.

The embodiments of this application also provide an electronic device, which includes any one of the electronic elements described in the above electronic element embodiments. Because the electronic device includes any one of the electronic elements described in the above electronic element embodiments, the electronic device has the same beneficial effects as the electronic elements, so the beneficial effects will not be repeated herein.

Figure 2:
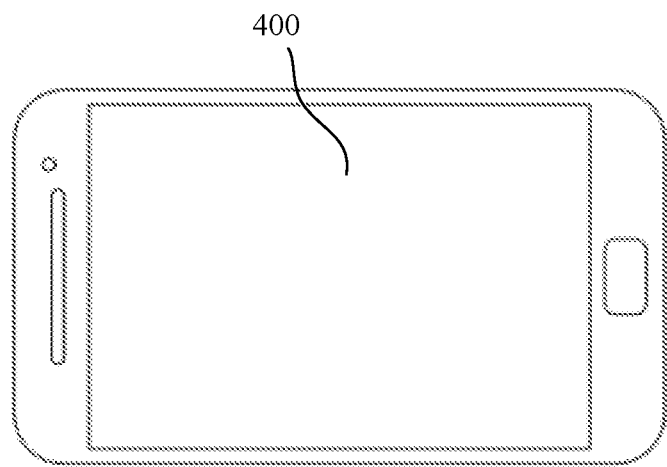
FIG. 2 is a schematic structural diagram of an electronic device according to an embodiment of this application.

For example, as shown in FIG. 2, this application provides an electronic device 400. The electronic device 200 includes any one of the organic electroluminescent devices described in the above organic electroluminescent device embodiments. The electronic device 400 may be a display device, a lighting device, an optical communication device or other types of electronic devices, for example, including, but not limited to, a computer screen, a mobile phone screen, a television, an electronic paper, an emergency lighting, an optical module, etc. Because the electronic device 400 includes any one of the organic electroluminescent devices described in the above organic electroluminescent device embodiments, the electronic device 400 has the same beneficial effects as the organic electroluminescent devices, so the beneficial effects will not be repeated herein.

Figure 4:
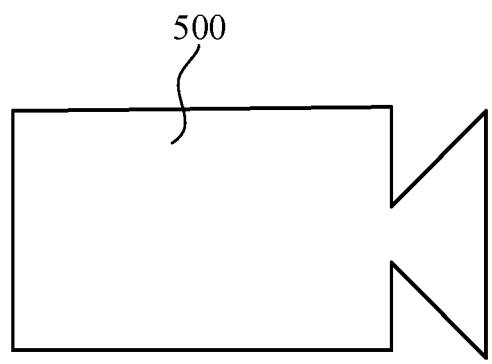
FIG. 4 is a schematic structural diagram of an electronic device according to an embodiment of this application.

For another example, as shown in FIG. 4, this application provides an electronic device 500. The electronic device 500 includes any one of the organic electroluminescent devices described in the above organic electroluminescent device embodiments. The electronic device 500 may be a solar power generation device, an optical detector, a fingerprint recognition device, an optical module, a charge-coupled device (CCD) camera, or other types of electronic devices.

Because the electronic device 500 includes any one of the photoelectric conversion devices described in the above photoelectric conversion device embodiments, the electronic device 500 has the same beneficial effects as the optical-to-electrical conversions, so the beneficial effects will not be repeated herein.

Below, this application will be described in further detail through examples. However, the following examples are merely for describing this application, rather than limiting this application.

Generally, the nitrogen-containing compounds of this application may be prepared by the method described in this application. Unless further stated, the meanings of the substituent symbols in this application are the same as those of the substituent symbols in chemical formula 1. It is to be appreciated by those skilled in the art that: the chemical reactions described in this application may be used to properly prepare many other compounds of this application, and other methods for preparing the nitrogen-containing compounds of this application are to be construed as falling within the scope of this application. For example, those skilled in the art may synthesize other nitrogen-containing compounds of this application by making reference to or appropriately modifying the preparation methods provided in this application, for example, by virtue of appropriate protection groups, using other known reagents other than those described in this application, modifying the reaction conditions, etc.

In the synthesis examples described below, the temperatures are in degrees Celsius unless otherwise stated.

Synthesis of Compound 1

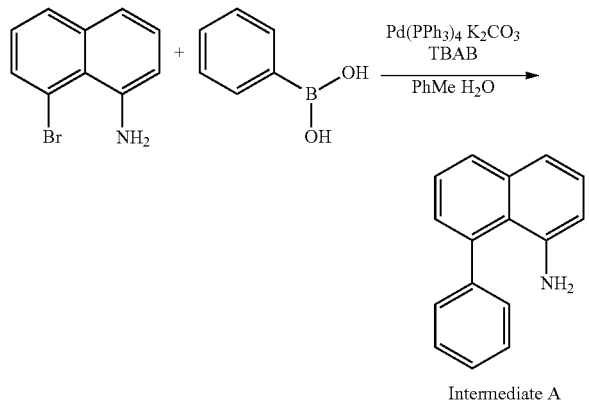

Intermediate A 8-bromo-1-naphthylamine (22.21 g, 100 mmol), benzoboric acid (12.19 g, 100 mmol), potassium carbonate (43.85 g, 200 mmol), tetrabutyl ammonium bromide (6.44 g, 20 mmol), toluene (160 mL), and ultrapure water (40 mL) were added to a 500 mL of three-necked flask with nitrogen protection and condensation reflux device, and heated and stirred under the protection of nitrogen. When the temperature rose to 40° C., tetrakis(triphenylphosphine)palladium (0.57 g, 0.5 mmol) was added. The mixture was heated to 100° C. under reflux, and reacted for 12 h. After the reaction was completed and the temperature of the reaction liquid dropped to room temperature, the reaction liquid was extracted with 200 mL of toluene, washed with 400 mL of ultrapure water, and dried with anhydrous sodium sulfate. After the extraction, the product was passed through a silica gel column. The residual solution from the column was concentrated to 80 mL, heated to make the solid completely dissolved, and slowly cooled for recrystallization. The recrystallization was carried out twice to obtain Intermediate A (15.35 g, yield: 70%).

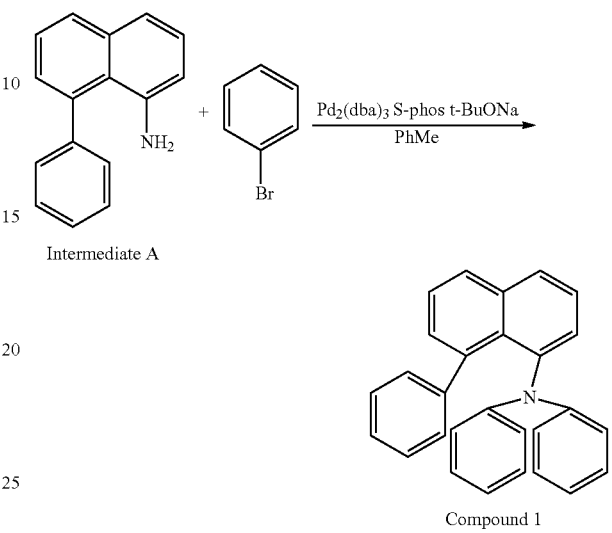

Intermediate A (15.35 g, 69.9 mmol), bromophenzene (23.1 g, 146.8 mmol), and toluene (150 mL) were added to a 500 mL of three-necked flask with nitrogen protection and condensation reflux device, and heated and stirred under the protection of nitrogen. When the temperature rose to 50° C., terterbutanol sodium (10.07 g, 104.8 mmol), S-phos (0.25 g, 0.69 mmol), and Pd$_2$(dba)$_3$ (0.2 g, 0.35 mmol) were added sequentially. The mixture was heated to 110° C. under toluene reflux, and reacted for 10 h. The stirring and heating were stopped after the reaction was completed. The reaction liquid was treated after the temperature dropped to room temperature. 100 mL of ultrapure water was added to the reaction liquid, and stirred for liquid separation. The aqueous phase was extracted twice with 100 mL of toluene. The organic phases were combined and washed three times with 100 mL of ultrapure water, dried with anhydrous sodium sulfate, and passed through a silica gel column. Then the column was washed with 200 mL of toluene. The organic phases were concentrated to 100 mL, heated to make the solid completely dissolved, and cooled for crystallization. The solid was filtered, and recrystallized with 60 mL of dichloroethane to obtain Compound 1 as a white solid (15.55 g, yield: 60%).

$^1$H NMR (400 MHz, CDCl$_3$): 7.64-7.57 (m, 4H), 7.47-7.40 (m, 4H), 7.33 (t, 1H), 7.26 (t, 4H), 7.00 (d, 1H), 6.67-6.61 (m, 3H), 6.42 (d, 4H);

Mass spectrum: m/z=372.17[M+H]$^+$.

Compound 2 to Compound 27 were Synthesized by the Following Synthesis Route

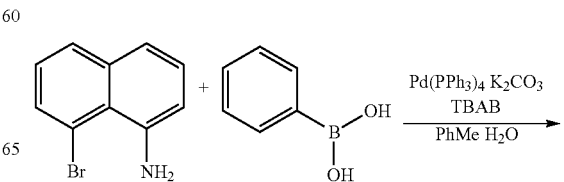

-continued

Intermediate A

Compound 2 to 27

Synthesis of Compound 2

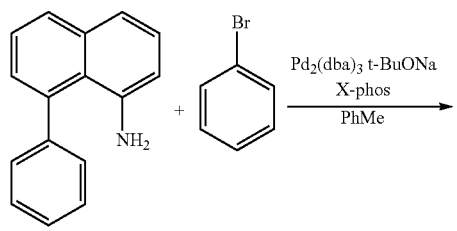

Intermediate A

Intermediate B

Intermediate A (15.35 g, 69.9 mmol), bromophenzene (11.0 g, 69.9 mmol), and toluene (150 mL) were added to a 500 mL of three-necked flask with nitrogen protection and condensation reflux device, and heated and stirred under the protection of nitrogen. When the temperature rose to 50° C., terterbutanol sodium (10.07 g, 104.8 mmol), X-phos (0.32 g, 0.69 mmol), and Pd$_2$(dba)$_3$ (0.2 g, 0.35 mmol) were added. The mixture was heated to 110° C. under toluene reflux, and reacted for 4 h. The stirring and heating were stopped after the reaction was completed. The reaction liquid was treated after the temperature dropped to room temperature. 100 mL of ultrapure water was added to the reaction liquid, and stirred for liquid separation. The aqueous phase was extracted twice with 100 mL of toluene. The organic phases were combined and washed three times with 100 mL of ultrapure water, dried with anhydrous sodium sulfate, and passed through a silica gel column. Then the column was washed with 200 mL of toluene. The organic phases were concentrated to 100 mL, heated to make the solid completely dissolved, and cooled for crystallization. The solid was filtered, and recrystallized with 50 mL of dichloroethane to obtain Intermediate B as a white solid (10.87 g, yield: 60%).

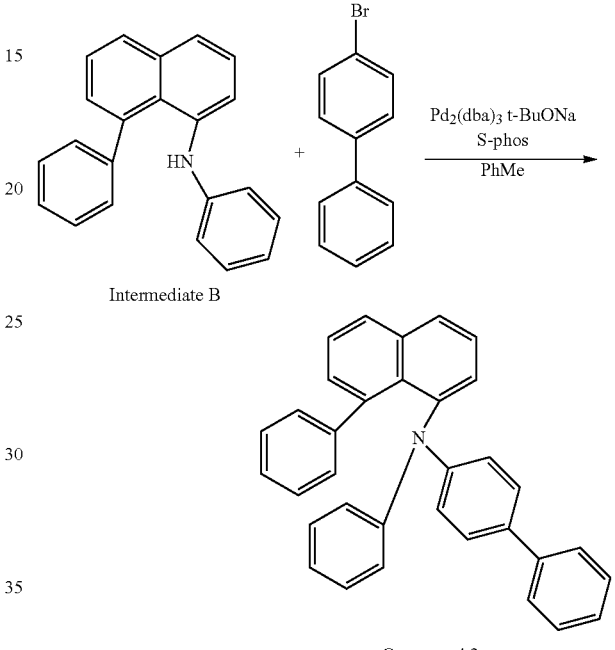

Compound 2

Intermediate B (10.87 g, 37 mmol), 4-bromobiphenyl (8.62 g, 37 mmol), and toluene (100 mL) were added to a 500 mL of three-necked flask with nitrogen protection and condensation reflux device, and heated and stirred under the protection of nitrogen. When the temperature rose to 50° C., terterbutanol sodium (5.28 g, 55 mmol), S-phos (0.37 g, 0.37 mmol), and Pd$_2$(dba)$_3$ (0.1 g, 0.18 mmol) were added. The mixture was heated to toluene reflux, and reacted for 8 h. The stirring and heating were stopped after the reaction was completed. The reaction liquid was treated after the temperature dropped to room temperature. 80 mL of ultrapure water was added to the reaction liquid, and stirred for liquid separation. The aqueous phase was extracted twice with 100 mL of toluene. The organic phases were combined and washed three times with 100 mL of ultrapure water, dried with anhydrous sodium sulfate, and passed through a silica gel column. Then the column was washed with 200 mL of toluene. The organic phases were concentrated to 80 mL, heated to make the solid completely dissolved, and cooled for crystallization. The solid was filtered, and recrystallized with 45 mL of dichloroethane to obtain Compound 2 as a white solid (9.11 g, yield: 550%).

$^1$H NMR (400 MHz, CDCl$_3$): 7.64-7.50 (m, 8H), 7.47-7.39 (m, 7H), 7.33 (t, 1H), 7.25 (t, 2H), 6.99 (d, 1H), 6.66-6.61 (m, 4H), 6.49 (d, 2H);

Mass spectrum: m/z=448.20[M+H]$^+$.

The compounds in Table 1 below were prepared with reference to the synthesis method of Compound 2 by using Raw material 2 to replace 4-bromobiphenyl and using Raw material 1 to replace bromobenzene.

TABLE 1
Compound structure, preparation, and characterization data
| Compound | Raw material 1 | Raw material 2 | Compound structure | Second-step yield (%) | Third-step yield (%) | Mass spectrum (m/z) [M + H]+ |
|---|---|---|---|---|---|---|
| 5 |  | 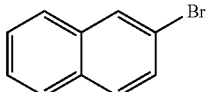 | 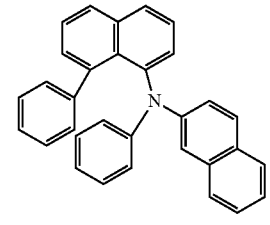 [SMILES: c1ccc(-c2cccc3cccc(N(c4ccccc4)c4ccc5ccccc5c4)c23)cc1] | 54 | 55 | 422.18 |
| 9 |  | 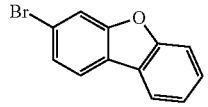 [SMILES: Brc1ccc2c(c1)oc1ccccc12] | 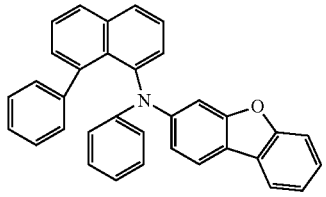 [SMILES: c1ccc(-c2cccc3cccc(N(c4ccccc4)c4ccc5c(c4)oc4ccccc45)c23)cc1] | 45 | 54 | 462.18 |
| 13 |  | 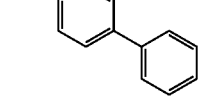 | 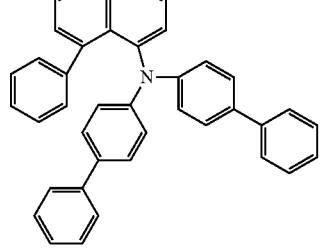 | 44 | 48 | 524.23 |
| 23 |  | 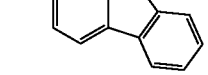 | 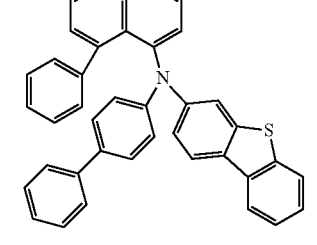 | 55 | 60 | 554.19 |
| 27 |  | 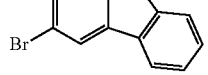 | 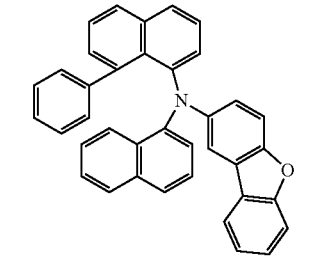 [SMILES: c1ccc(-c2cccc3cccc(N(c4ccc5oc6ccccc6c5c4)c4cccc5ccccc45)c23)cc1] | 54 | 50 | 512.19 |

Compound 28 to Compound 117 were Synthesized by the Following Synthesis Route

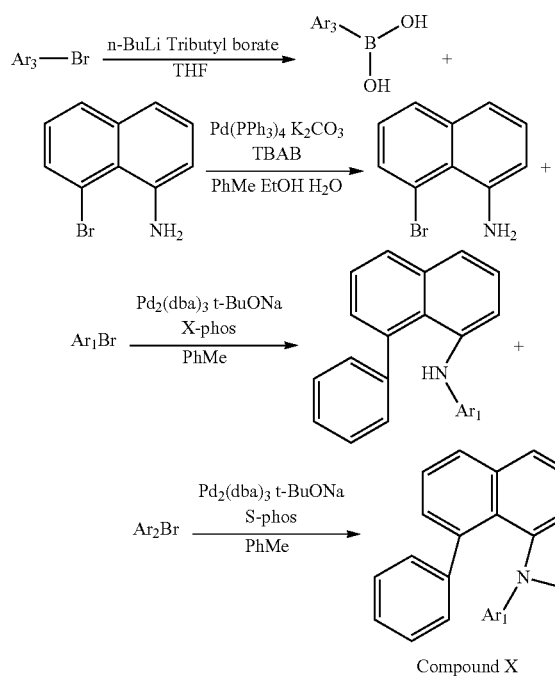

Synthesis of Compound 28

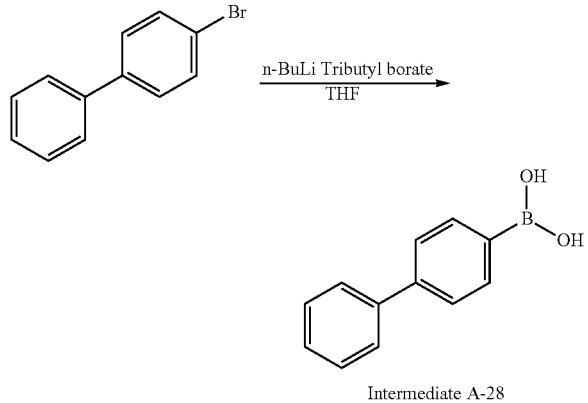

THF (230 mL) and 4-bromobiphenyl (23.3 g, 100 mmol) were added to a 500 mL of three-necked flask equipped with a mechanical stirrer and a y-tube fitted with a thermometer, stirred, and cooled to −85° C. to −80° C. by liquid nitrogen. Then n-butyl lithium (55 mL, 110 mmol) was added dropwise with the temperature being controlled to be −85° C. to −80° C. After the dropwise addition, the mixture was reacted at −85° C. to −80° C. for 1.0 h. Tributyl borate (27.6 g, 120 mmol) was added dropwise with the temperature being controlled to be −85° C. to −80° C. After the dropwise addition, the mixture was reacted at −85° C. to −80° C. for 2.0 h. Then the temperature control was stopped, and the temperature naturally rose to 20° C. to 25° C. After the reaction was completed, the reaction liquid was poured into concentrated hydrochloric acid (20 mL, 12 mol/L) and stirred for 5 min. Then 200 mL of petroleum ether and 200 mL of ultrapure water were added to the mixture and stirred for 5 min for liquid separation. The aqueous phase was extracted twice with 100 mL of petroleum ether. The organic phases were combined, and washed with 300 mL of water until no more product precipitates. The product was obtained by filtration, heated and slurried in n-heptane, to obtain Intermediate A-28 as a white solid (13.89 g, yield: 70%).

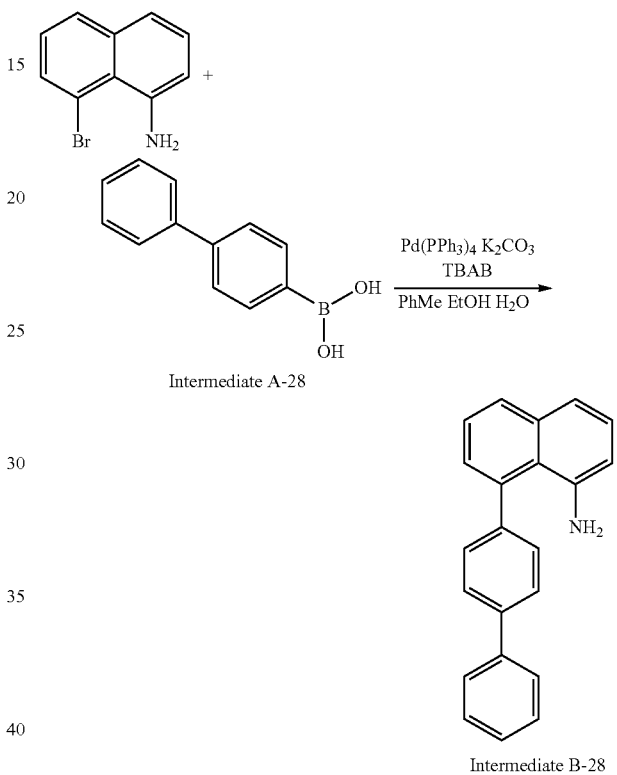

8-bromo-1-naphthylamine (15.54 g, 70 mmol), 4-biphenylboronic acid (13.89 g, 70 mmol), potassium carbonate (30.69 g, 140 mmol), tetrabutylammonium bromide (4.5 g, 14 mmol), toluene (120 mL), ethanol (30 mL), and ultrapure water (30 mL) were added to a 500 mL of three-necked flask with nitrogen protection and condensation reflux device, and heated and stirred under the protection of nitrogen. When the temperature rose to 40° C., tetrakis(triphenylphosphine) palladium (0.45 g, 0.4 mmol) was added. The mixture was heated to reflux, and reacted for 18 h. After the reaction was completed and the temperature of the reaction liquid dropped to room temperature, the reaction liquid was extracted with 200 mL of toluene, washed with 400 mL of ultrapure water, and dried with anhydrous sodium sulfate. After the extraction, the product was passed through a silica gel column. The residual solution from the column was concentrated to 80 mL, heated to make the solid completely dissolved, and slowly cooled for recrystallization. The product was separated through a column, which was eluted with petroleum ether:acetic ether (6:1) to obtain Product Intermediate B-28 (12.4 g, yield: 60%).

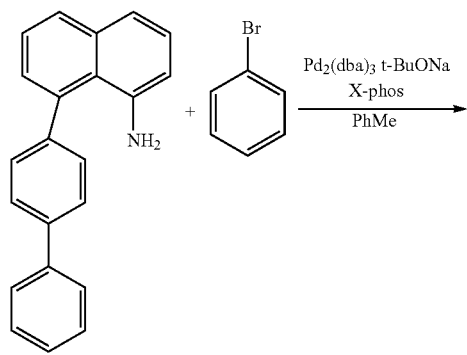

Intermediate B-28

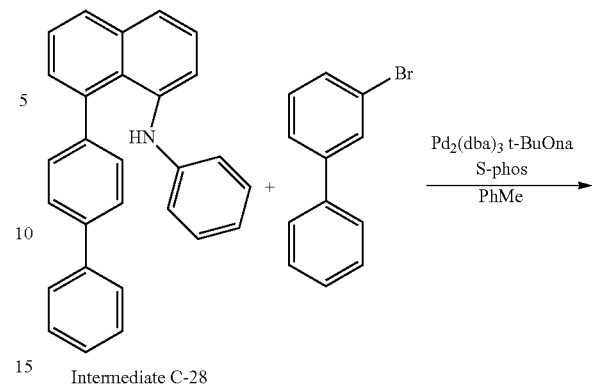

Intermediate C-28

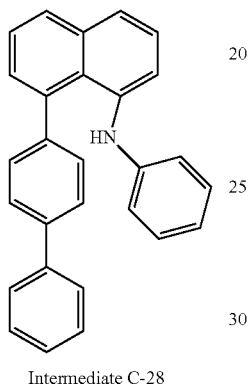

Intermediate C-28

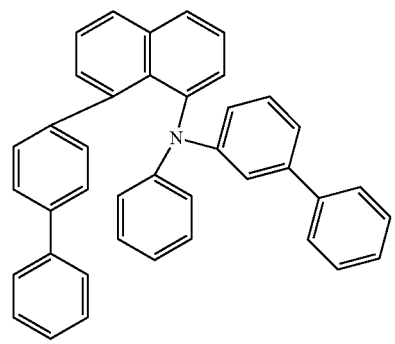

Compound 28

Intermediate B-28 (12.4 g, 41.9 mmol), bromophenzene (6.59 g, 41.9 mmol), and toluene (130 mL) were added to a 500 mL of three-necked flask with nitrogen protection and condensation reflux device, and heated and stirred under the protection of nitrogen. When the temperature rose to 50° C., terterbutanol sodium (6.03 g, 62.82 mmol), X-phos (0.19 g, 0.41 mmol), and Pd$_2$(dba)$_3$ (0.12 g, 0.21 mmol) were added. The mixture was heated to 110° C. under toluene reflux, and reacted for 4 h. The stirring and heating were stopped after the reaction was completed. The reaction liquid was treated after the temperature dropped to room temperature. 100 mL of ultrapure water was added to the reaction liquid, and stirred for liquid separation. The aqueous phase was extracted twice with 100 mL of toluene. The organic phases were combined and washed three times with 100 mL of ultrapure water, dried with anhydrous sodium sulfate, and passed through a silica gel column. Then the column was washed with 200 mL of toluene. The organic phases were concentrated to 100 mL, heated to make the solid completely dissolved, and cooled for crystallization. The solid was filtered, and recrystallized with 60 mL of dichloroethane to obtain Intermediate C-28 as a white solid (9.45 g, yield: 60%).

Intermediate C-28 (9.45 g, 25.43 mmol), 3-bromobiphenyl (5.9 g, 25.43 mmol), and toluene (100 mL) were added to a 500 mL of three-necked flask with nitrogen protection and condensation reflux device, and heated and stirred under the protection of nitrogen. When the temperature rose to 50° C., terterbutanol sodium (3.67 g, 38.16 mmol), S-phos (0.21 g, 0.51 mmol), and Pd$_2$(dba)$_3$ (0.23 g, 0.25 mmol) were added. The mixture was heated to toluene reflux, and reacted for 8 h. The stirring and heating were stopped after the reaction was completed. The reaction liquid was treated after the temperature dropped to room temperature. 80 mL of ultrapure water was added to the reaction liquid, and stirred for liquid separation. The aqueous phase was extracted twice with 100 mL of toluene. The organic phases were combined and washed three times with 100 mL of ultrapure water, dried with anhydrous sodium sulfate, and passed through a silica gel column. Then the column was washed with 200 mL of toluene. The organic phases were concentrated to 80 mL, heated to make the solid completely dissolved, and cooled for crystallization. The solid was filtered, and recrystallized with 45 mL of dichloroethane to obtain Compound 28 as a white solid (7.3 g, yield: 55%).

$^1$H NMR (400 MHz, CDCl$_3$): 7.69 (d, 2H), 7.60-7.57 (m, 4H), 7.55-7.48 (m, 8H), 7.47-7.38 (m, 3H), 7.35-7.24 (m, 4H), 7.11 (d, 1H), 6.95 (d, 1H), 6.87 (t, 1H), 6.65-6.57 (m, 3H), 6.45 (d, 2H);

Mass spectrum: m/z=524.23[M+H]$^+$.

The compounds in Table 2 below were prepared with reference to the synthesis method of Compound 28 by using Raw material 1 to replace 4-bromobiphenyl, using Raw material 2 to replace bromobenzene and using Raw material 3 to replace 3-bromobiphenyl.

TABLE 2

Compound structure, preparation, and characterization data

| Compound | Raw material 1 | Raw material 2 | Raw material 3 | Compound structure | Mass spectrum [M + H]+ |
|---|---|---|---|---|---|
| 34 | 3-bromobiphenyl | bromobenzene | 2-bromo-9,9-dimethylfluorene | (structure) | 564.26 |
| 36 | 3-bromobiphenyl | bromobenzene | 2-bromodibenzofuran | (structure) | 538.21 |
| 38 | 4-bromobiphenyl | bromobenzene | 2-bromodibenzothiophene | (structure) | 554.19 |
| 41 | 4-bromobiphenyl | 4-bromobiphenyl | 3-bromobiphenyl | (structure) | 600.26 |
| 53 | 4-bromobiphenyl | 2-bromonaphthalene | 2-bromo-9,9-dimethylfluorene | (structure) | 614.28 |

TABLE 2-continued
Compound structure, preparation, and characterization data
| Compound | Raw material 1 | Raw material 2 | Raw material 3 | Compound structure | Mass spectrum [M + H]+ |
|---|---|---|---|---|---|
| 74 | 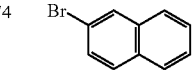 | 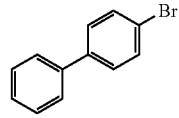 [SMILES: Brc1ccc(-c2ccccc2)cc1] | 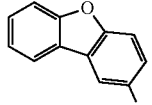 | 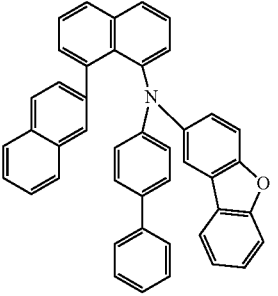 [SMILES: c1ccc(-c2ccc(N(c3ccc4oc5ccccc5c4c3)c3cccc4cccc(-c5ccc6ccccc6c5)c34)cc2)cc1] | 588.22 |
| 83 | 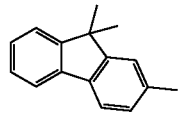 [SMILES: Cc1ccc2c(c1)C(C)(C)c1ccccc1-2] | 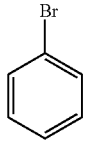 | 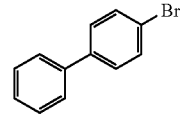 [SMILES: Brc1ccc(-c2ccccc2)cc1] | 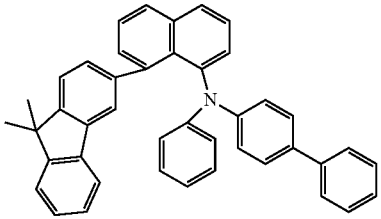 [SMILES: CC1(C)c2ccccc2-c2cc(-c3cccc4cccc(N(c5ccccc5)c5ccc(-c6ccccc6)cc5)c34)ccc21] | 564.26 |
| 109 | 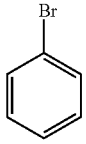 | 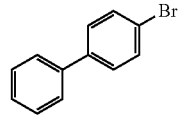 [SMILES: Brc1ccc(-c2ccccc2)cc1] | 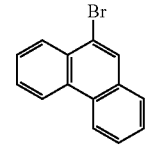 [SMILES: Brc1cc2ccccc2c2ccccc12] | 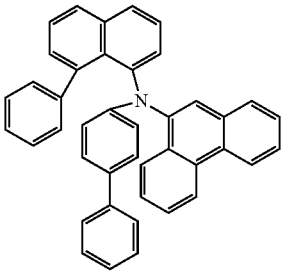 [SMILES: c1ccc(-c2ccc(N(c3cc4ccccc4c4ccccc34)c3cccc4cccc(-c5ccccc5)c34)cc2)cc1] | 548.23 |
| 110 | 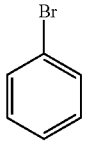 | 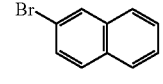 | 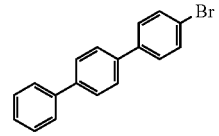 [SMILES: Brc1ccc(-c2ccc(-c3ccccc3)cc2)cc1] | 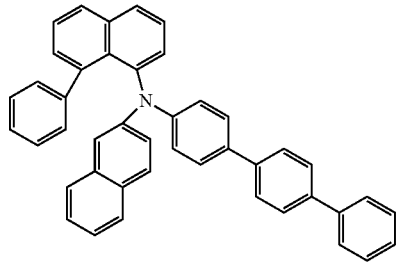 [SMILES: c1ccc(-c2ccc(-c3ccc(N(c4ccc5ccccc5c4)c4cccc5cccc(-c6ccccc6)c45)cc3)cc2)cc1] | 574.25 |
| 111 | 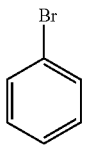 | 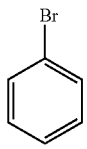 | 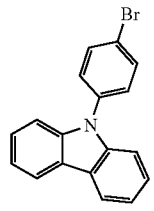 [SMILES: Brc1ccc(-n2c3ccccc3c3ccccc32)cc1] | 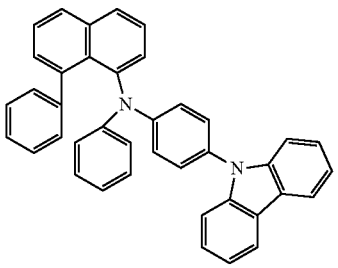 [SMILES: c1ccc(-c2cccc3cccc(N(c4ccccc4)c4ccc(-n5c6ccccc6c6ccccc65)cc4)c23)cc1] | 537.23 |

TABLE 2-continued
Compound structure, preparation, and characterization data
| Compound | Raw material 1 | Raw material 2 | Raw material 3 | Compound structure | Mass spectrum [M + H]+ |
|---|---|---|---|---|---|
| 112 | 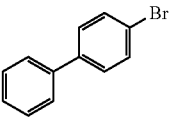 [SMILES: Brc1ccc(-c2ccccc2)cc1] | 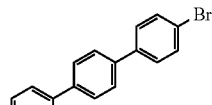 | 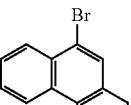 | 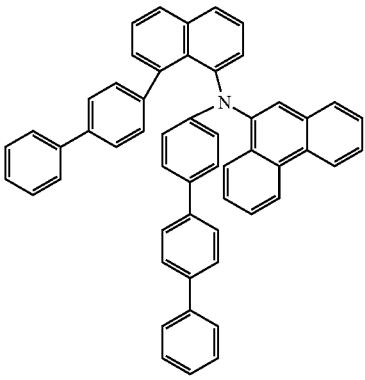 [SMILES: c1ccc(-c2ccc(-c3ccc(N(c4cc5ccccc5c5ccccc45)c4cccc5cccc(-c6ccc(-c7ccccc7)cc6)c45)cc3)cc2)cc1] | 700.29 |
| 113 | 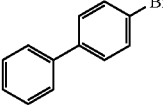 | 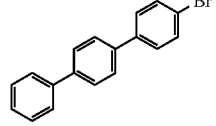 | 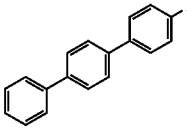 | 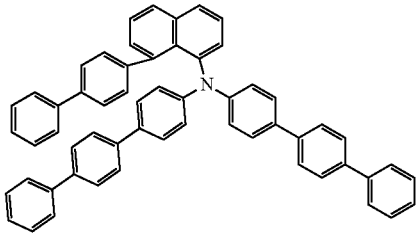 [SMILES: c1ccc(-c2ccc(-c3ccc(N(c4ccc(-c5ccc(-c6ccccc6)cc5)cc4)c4cccc5cccc(-c6ccc(-c7ccccc7)cc6)c45)cc3)cc2)cc1] | 752.32 |
| 114 | 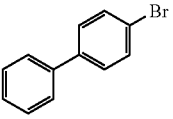 [SMILES: Brc1ccc(-c2ccccc2)cc1] | 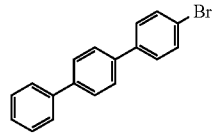 [SMILES: Brc1ccc(-c2ccc(-c3ccccc3)cc2)cc1] | 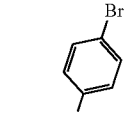 | 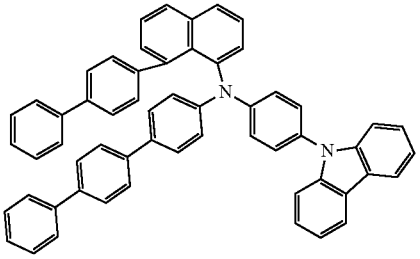 [SMILES: c1ccc(-c2ccc(-c3ccc(N(c4ccc(-n5c6ccccc6c6ccccc65)cc4)c4cccc5cccc(-c6ccc(-c7ccccc7)cc6)c45)cc3)cc2)cc1] | 765.32 |
| 115 | 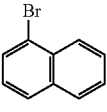 | 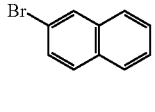 | 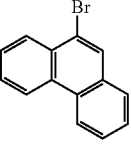 [SMILES: Brc1cc2ccccc2c2ccccc12] | 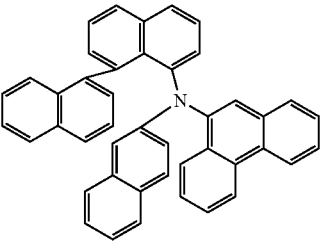 [SMILES: c1ccc2cc(N(c3cc4ccccc4c4ccccc34)c3cccc4cccc(-c5cccc6ccccc56)c34)ccc2c1] | 572.23 |
| 116 |  | 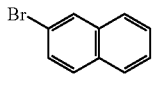 | 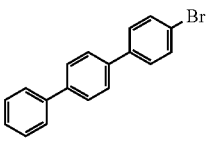 [SMILES: Brc1ccc(-c2ccc(-c3ccccc3)cc2)cc1] | 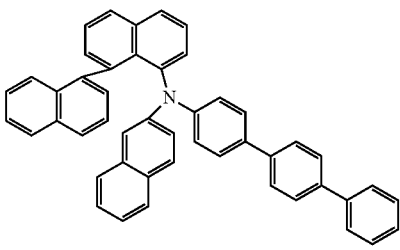 [SMILES: c1ccc(-c2ccc(-c3ccc(N(c4ccc5ccccc5c4)c4cccc5cccc(-c6cccc7ccccc67)c45)cc3)cc2)cc1] | 624.26 |

TABLE 2-continued

Compound structure, preparation, and characterization data

| Compound | Raw material 1 | Raw material 2 | Raw material 3 | Compound structure | Mass spectrum [M + H]+ |
|---|---|---|---|---|---|
| 117 | 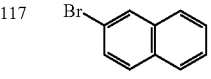 | 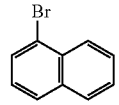 | 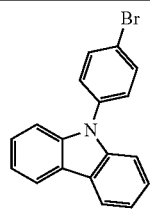 | 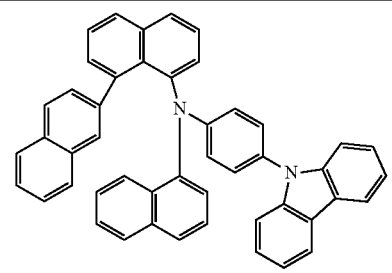 | 637.26 |

Preparation and Performance Evaluation of Organic Electroluminescent Device

A blue organic electroluminescent device was prepared by the following method.

An ITO substrate with an ITO thickness of 1150 Å (manufactured by Corning) was cut into a size of 40 mm (long) by 40 mm (wide) by 0.7 mm (thick), which was prepared into a TOP substrate having a cathode, an anode and an insulating layer pattern by lithography. The TOP substrate was surface-treated with UV-ozone and $O_2:N_2$ plasma to increase the work function of the anode (experimental substrate) and remove the slag.

m-MTDATA was vacuum evaporated on the experimental substrate (anode) to form a hole injection layer (HIL) with a thickness of 100 Å, and compound 1 was vacuum evaporated on the hole injection layer to form a first hole transport layer with a thickness of 1000 Å.

TCTA was vacuum evaporated on the first hole transport layer to form a second hole transport layer with a thickness of 100 Å.

A light-emitting layer (EML) with a thickness of 200 Å was formed by using α,β-ADN as the host and doping with BD-1 according to a film thickness ratio of 3%.

DBimiBphen and LiQ were mixed at a weight ratio of 2:1 and evaporated to form a 300 Å thick electron transport layer (ETL), Yb was evaporated on the electron transport layer to form a 10 Å thick electron injection layer (EIL), and then magnesium (Mg) and silver (Ag) were mixed at an evaporation rate of 1:9 and vacuum-evaporated on the electron injection layer to form a 120 Å thick cathode.

Furthermore, a 650 Å thick CP-1 was evaporated on the cathode to protect the cathode and enhance the optical coupling output.

In addition, when the electroluminescent device is prepared, the structures of the above materials are as follows:

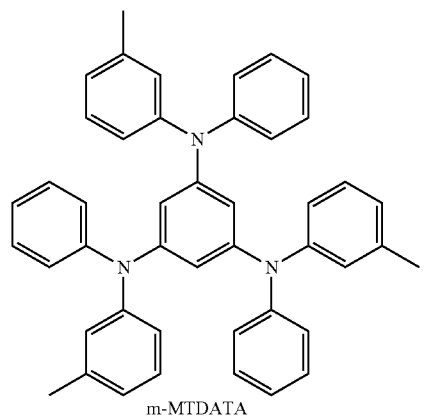

m-MTDATA

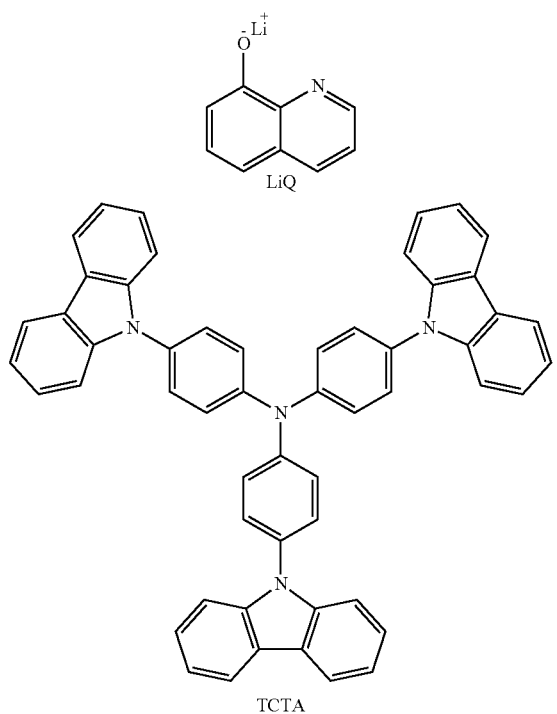

LiQ

TCTA

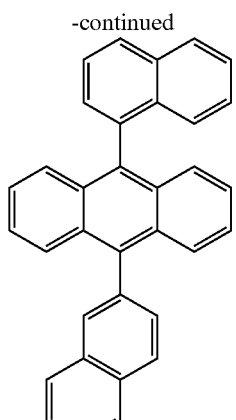

α,β-ADN

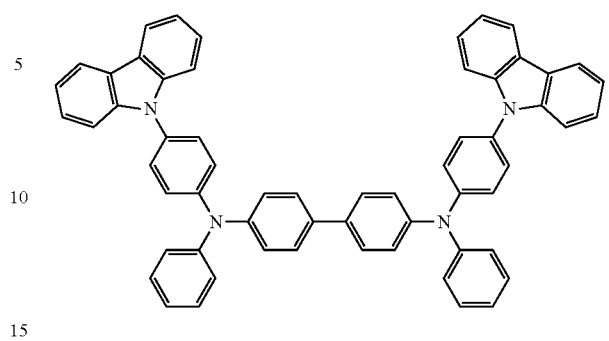

CP-1

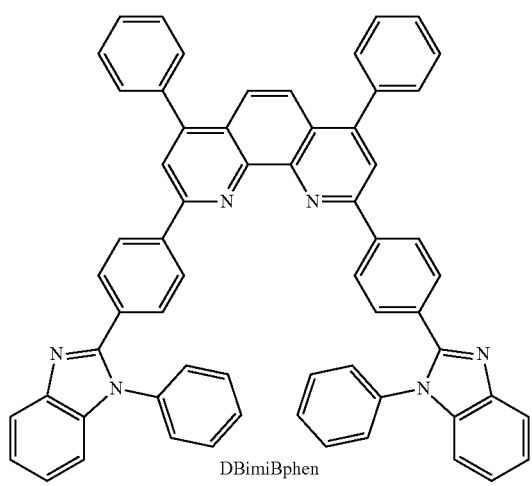

DBimiBphen

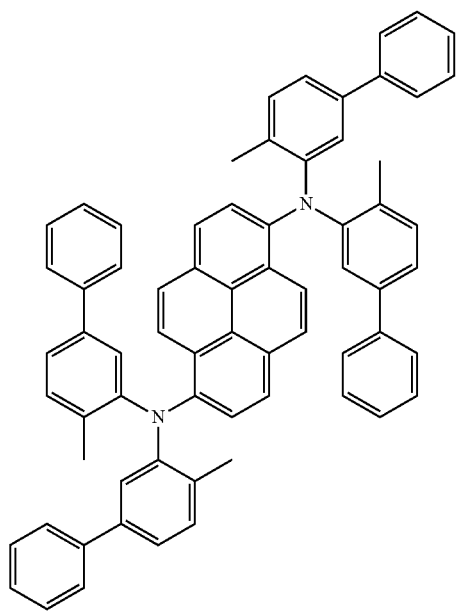

BD-1

Examples 2 to 7

Examples 2 to 7 were the same as Example 1 except that the compound 1 of the first hole transport layer (HTL) in the above device structure in Example 1 was replaced with Compounds 2, 5, 9, 13, 23, or 27 respectively. The organic electroluminescent devices in these examples were prepared by the same preparation process as that in Example 1.

Example 8

In Example 8, the device was prepared based on the same structure and process as those in Example 1 except that the first hole transport layer was replaced with the compound NPB and the second hole transport layer was replaced with the compound 28.

Examples 9 to 24

Examples 9 to 24 were the same as Example 8 except that the compound 28 of the second hole transport layer (HTL) in the above device structure in Example 8 was replaced with Compounds 34, 36, 38, 41, 53, 74, 83, 109, 110, 111, 112, 113, 114, 115, 116, or 117 respectively. The organic electroluminescent devices in these examples were prepared by the same preparation process as that in Example 8.

Comparative Example 1

The structure of the device in Comparative Example 1 was the same as that in Example 1 except that the compound 1 of the first hole transport layer (HTL) in Example 1 was replaced with the compound NPB. The organic electroluminescent device in this comparative example was prepared by the same preparation process as that in Example 1.

Comparative Example 2

The structure of the device in Comparative Example 2 was the same as that in Example 1 except that the compound 1 of the first hole transport layer (HTL) in Example 1 was replaced with the compound A. The organic electroluminescent device in this comparative example was prepared by the same preparation process as that in Example 1.

Comparative Example 3

The structure of the device in Comparative Example 3 was the same as that in Example 8 except that the compound 28 of the second hole transport layer (HTL) in Example 8 was replaced with the compound B. The organic electroluminescent device in this comparative example was prepared by the same preparation process as that in Example 8.

Comparative Example 4

The structure of the device in Comparative Example 4 was the same as that in Example 8 except that the compound 28 of the second hole transport layer (HTL) in Example 8 was replaced with Compound C. The organic electroluminescent device in this comparative example was prepared by the same preparation process as that in Example 8.

The structures of the NPB, Compound A, Compound B, and Compound C are as follows:

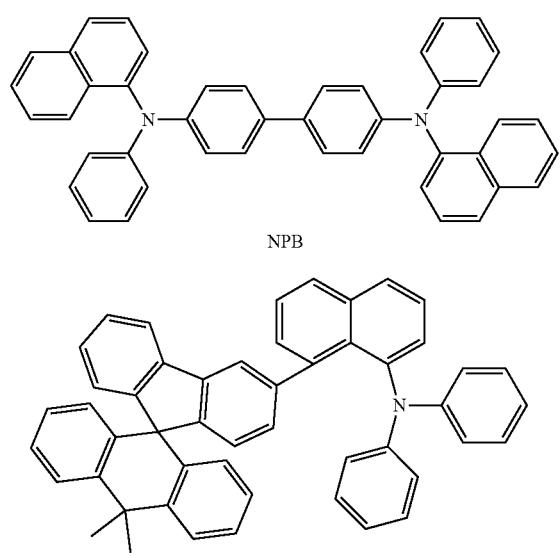

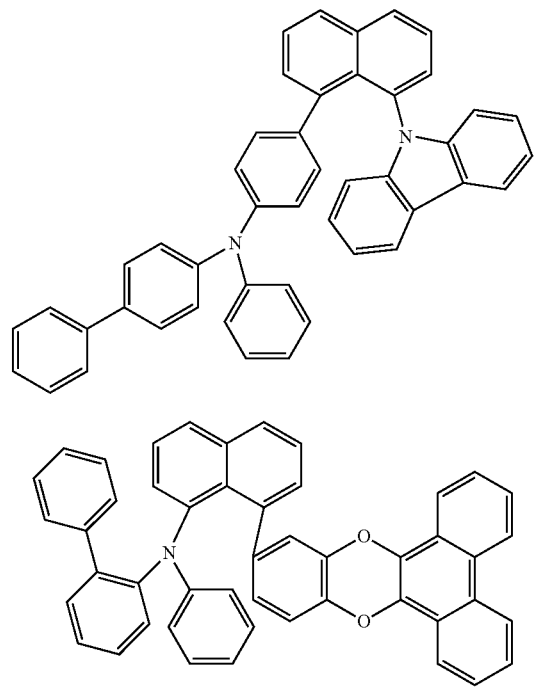

The IVL performance of the blue organic electroluminescent device prepared in Examples 1 to 24 and Comparative Examples 1 to 3 was tested under the condition of 10 mA/cm$^2$, and the T95 lifespan of the devices was tested at a constant current density of 20 mA/cm$^2$. The test results are shown in Table 3.

TABLE 3

Test results of performance of blue organic electroluminescent devices

| | Material of first hole transport layer | Material of second hole transport layer | Driving voltage (V) | Current efficiency (Cd/A) | Chromaticity coordinate CIEy | External quantum efficiency EQE (%) | T95 life (h) 20 mA/cm$^2$ |
|---|---|---|---|---|---|---|---|
| Example 1 | Compound 1 | TCTA | 3.92 | 6.11 | 0.047 | 12.5 | 120 |
| Example 2 | Compound 2 | TCTA | 3.95 | 6.12 | 0.048 | 12.6 | 117 |
| Example 3 | Compound 5 | TCTA | 4.08 | 6.09 | 0.048 | 12.2 | 118 |
| Example 4 | Compound 9 | TCTA | 4.08 | 5.89 | 0.046 | 12.0 | 123 |
| Example 5 | Compound 13 | TCTA | 3.99 | 6.19 | 0.047 | 12.7 | 118 |
| Example 6 | Compound 23 | TCTA | 3.97 | 5.93 | 0.046 | 12.2 | 121 |
| Example 7 | Compound 27 | TCTA | 3.98 | 5.79 | 0.048 | 11.8 | 123 |
| Example 8 | NPB | Compound 28 | 4.05 | 5.92 | 0.047 | 12.1 | 116 |
| Example 9 | NPB | Compound 34 | 3.93 | 6.11 | 0.047 | 12.4 | 119 |
| Example 10 | NPB | Compound 36 | 4.05 | 5.79 | 0.047 | 11.7 | 125 |
| Example 11 | NPB | Compound 38 | 4.04 | 6.12 | 0.048 | 12.6 | 120 |
| Example 12 | NPB | Compound 41 | 3.93 | 6.10 | 0.047 | 12.6 | 116 |
| Example 13 | NPB | Compound 53 | 3.95 | 5.93 | 0.048 | 12.2 | 115 |
| Example 14 | NPB | Compound 74 | 3.96 | 5.87 | 0.046 | 11.9 | 115 |
| Example 15 | NPB | Compound 83 | 3.92 | 5.86 | 0.048 | 12.0 | 121 |
| Example 16 | NPB | Compound 109 | 4.04 | 5.89 | 0.047 | 11.9 | 115 |
| Example 17 | NPB | Compound 110 | 3.90 | 6.11 | 0.046 | 12.5 | 119 |
| Example 18 | NPB | Compound 111 | 4.08 | 6.01 | 0.047 | 12.2 | 122 |
| Example 19 | NPB | Compound 112 | 3.94 | 5.99 | 0.048 | 12.2 | 118 |
| Example 20 | NPB | Compound 113 | 4.07 | 6.10 | 0.047 | 12.4 | 125 |
| Example 21 | NPB | Compound 114 | 4.09 | 6.03 | 0.046 | 12.4 | 121 |
| Example 22 | NPB | Compound 115 | 3.93 | 5.93 | 0.047 | 12.2 | 124 |
| Example 23 | NPB | Compound 116 | 4.07 | 6.11 | 0.048 | 12.4 | 121 |
| Example 24 | NPB | Compound 117 | 4.06 | 6.05 | 0.047 | 12.3 | 118 |

TABLE 3-continued

Test results of performance of blue organic electroluminescent devices

| | Material of first hole transport layer | Material of second hole transport layer | Driving voltage (V) | Current efficiency (Cd/A) | Chromaticity coordinate CIEy | External quantum efficiency EQE (%) | T95 life (h) 20 mA/cm² |
|---|---|---|---|---|---|---|---|
| Comparative Example 1 | NPB | TCTA | 4.21 | 5.19 | 0.048 | 10.6 | 95 |
| Comparative Example 2 | Compound A | TCTA | 4.19 | 5.21 | 0.047 | 10.81 | 98 |
| Comparative Example 3 | NPB | Compound B | 4.18 | 5.16 | 0.047 | 10.41 | 96 |
| Comparative Example 4 | NPB | Compound C | 4.20 | 5.17 | 0.047 | 10.51 | 97 |

As can be seen from Table 3, when the color coordinate CIEy does not vary greatly, the blue organic electroluminescent devices prepared in Examples 1 to 7 had lower driving voltage, better quantum efficiency and longer device life compared with Comparative Examples 1 and 2. Wherein compared with Comparative Examples 1 and 2, the lowest driving voltage of the blue organic electroluminescent devices prepared in Examples 1 to 7 is 3.92 V, which is reduced by up to 7.4%; the highest external quantum efficiency is 12.7, which is improved by up to 19.8%; and the T95 life is extended by at least 31.5%. This shows a very significant improvement for blue light-emitting devices.

As can be seen from Table 3, when the color coordinate CIEy does not vary greatly, the blue organic electroluminescent devices prepared in Examples 8 to 24 had lower driving voltage, higher efficiency and longer service life compared with Comparative Examples 1, 3 and 4. Wherein compared with Comparative Examples 1, 3 and 4, the driving voltage of the blue organic electroluminescent devices prepared in Examples 8 to 24 is reduced by up to 6.8%, the current efficiency is increased by at least 11.6%, the external quantum efficiency is increased by at least 10.4%, and the T95 life is extended by at least 19.8%.

Therefore, it can be concluded that the use of the compound of this application for preparing an organic electroluminescent device can effectively reduce the driving voltage of the electroluminescent device, improve the external quantum efficiency, and extend the life of the organic electroluminescent device.

It should be noted that only a method for preparing a blue organic electroluminescent device is given above, and the organic compound of this application can also be used in the electron transport layers of other colored organic electroluminescent devices, such as a red organic electroluminescent device and a green organic electroluminescent device to bring the same technical effects.

What is claimed is:

1. A nitrogen-containing compound having a structural formula as shown in Chemical Formula (1):

Chemical Formula (1)

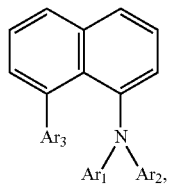

wherein $Ar_1$ and $Ar_2$ are selected from the group consisting of the following groups:

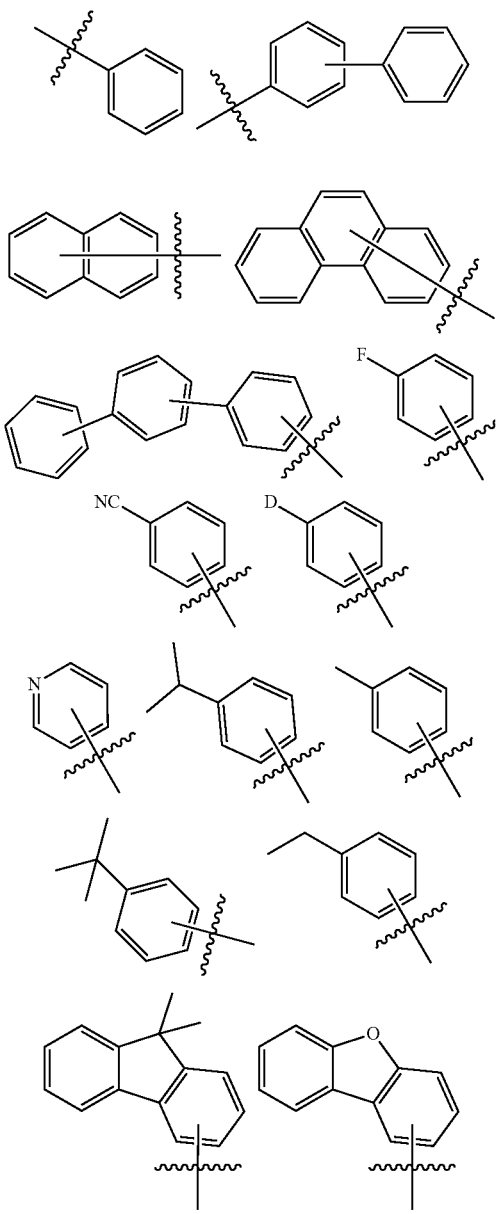

-continued
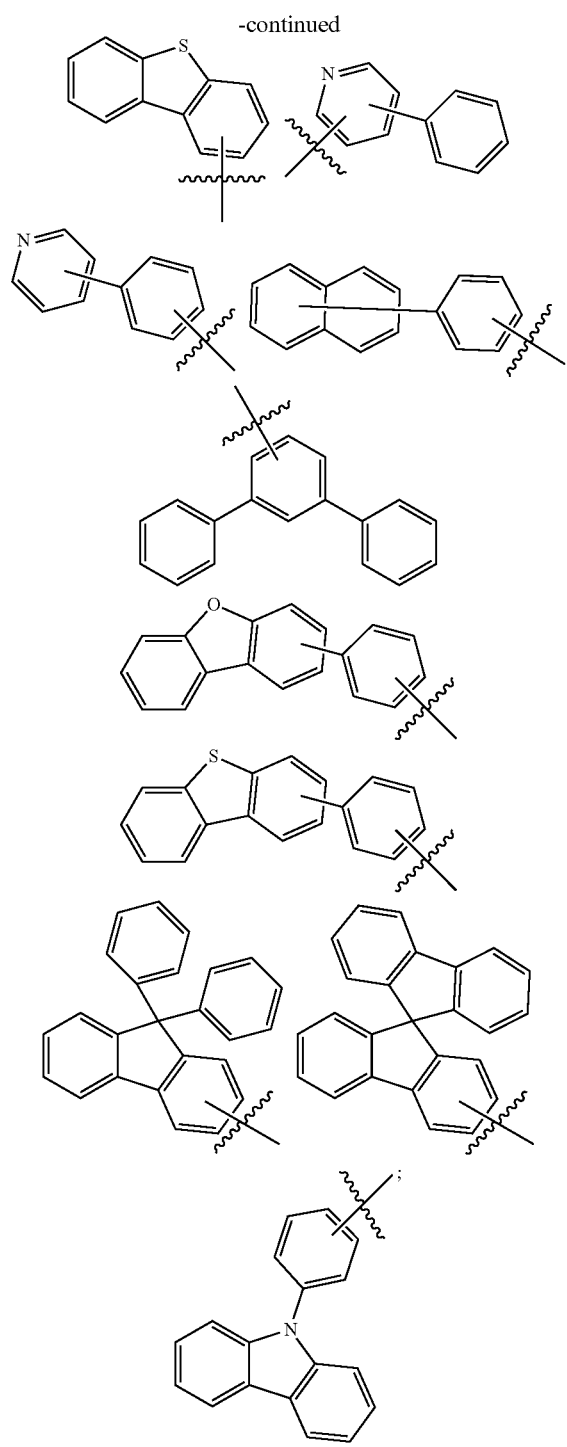
Ar₃ is selected from the group consisting of the following groups:
-continued
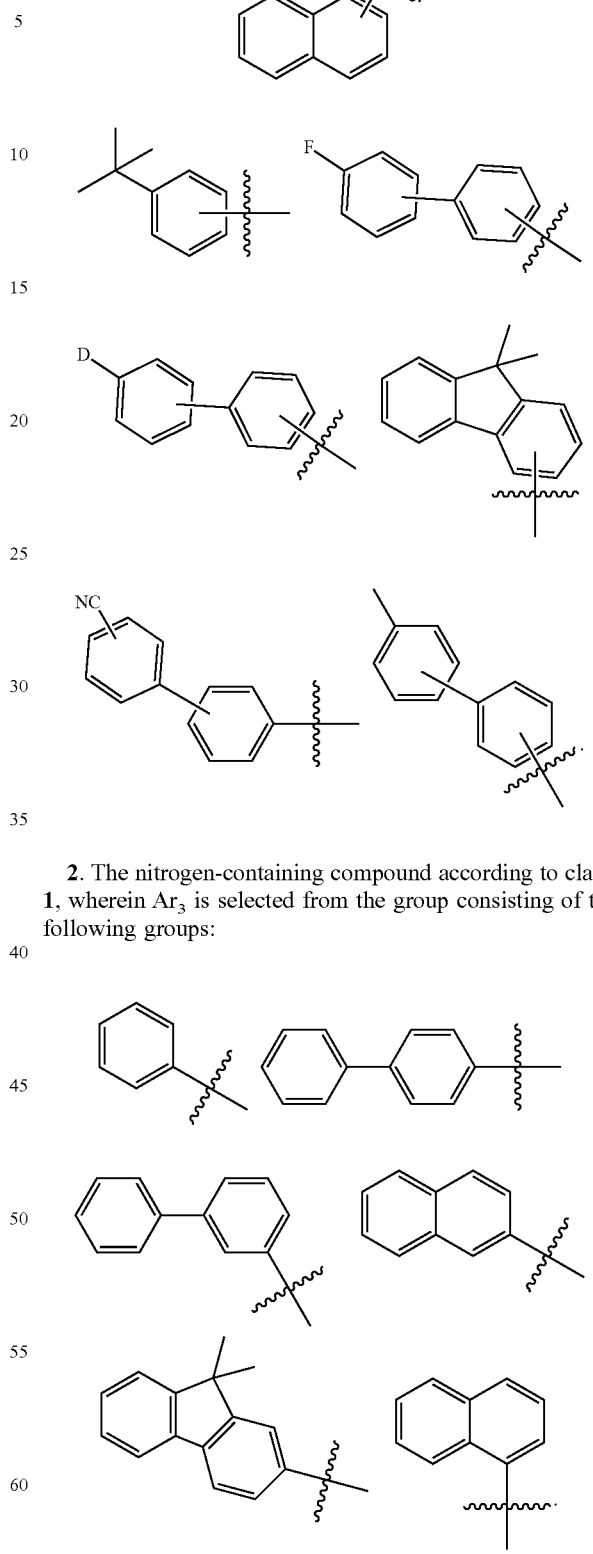
2. The nitrogen-containing compound according to claim 1, wherein Ar₃ is selected from the group consisting of the following groups:
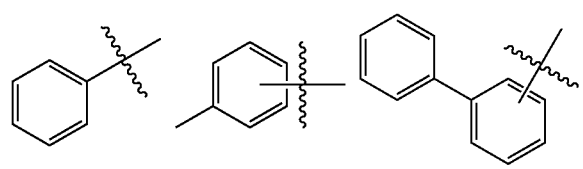
3. The nitrogen-containing compound according to claim 1, wherein Ar₁ and Ar₂ are selected from the group consisting of the following groups:

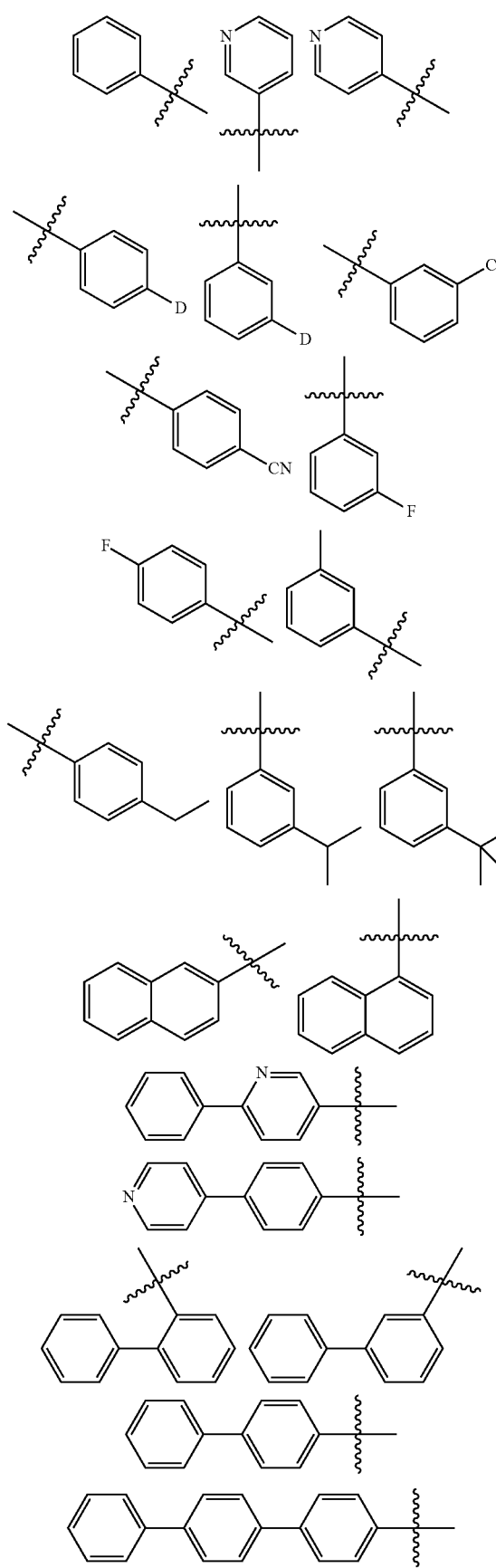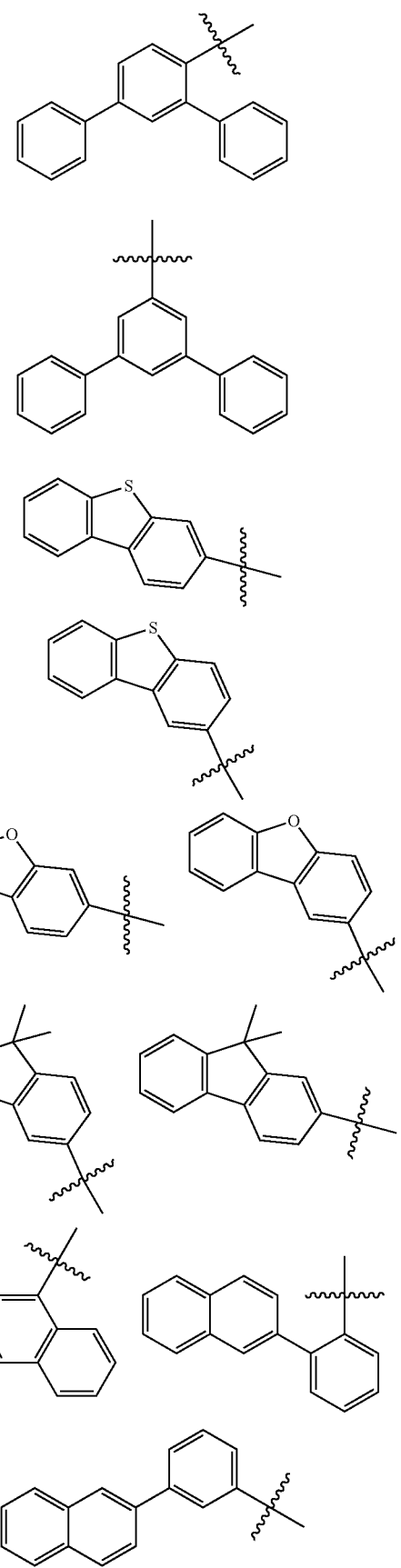

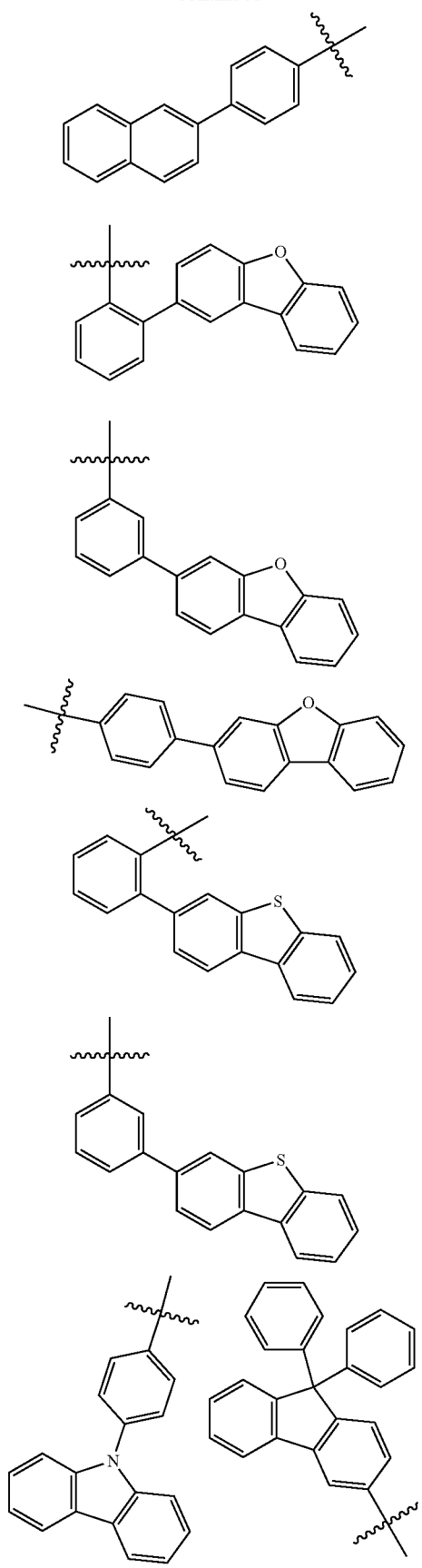
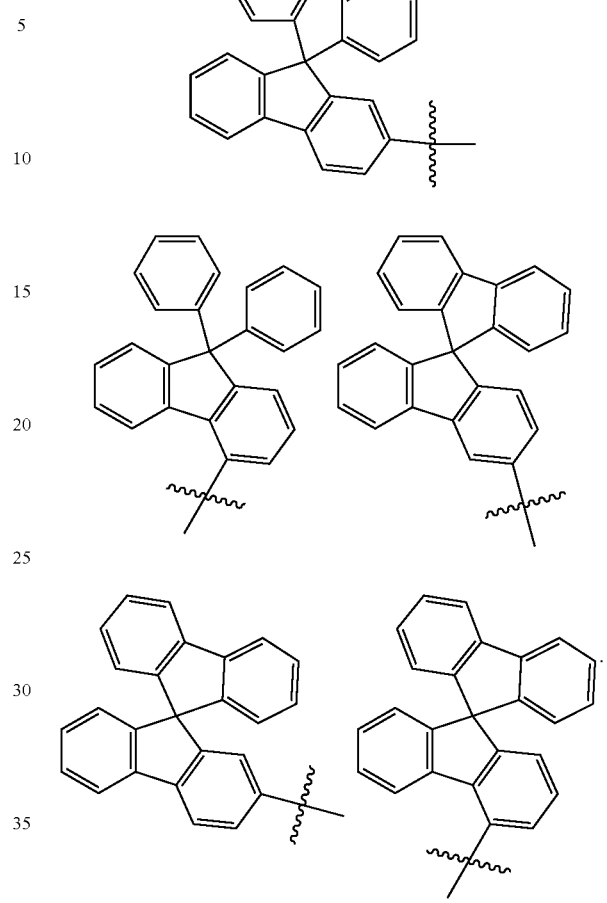
4. The nitrogen-containing compound according to claim 1, wherein the nitrogen-containing compound is selected from the group consisting of the following compounds:
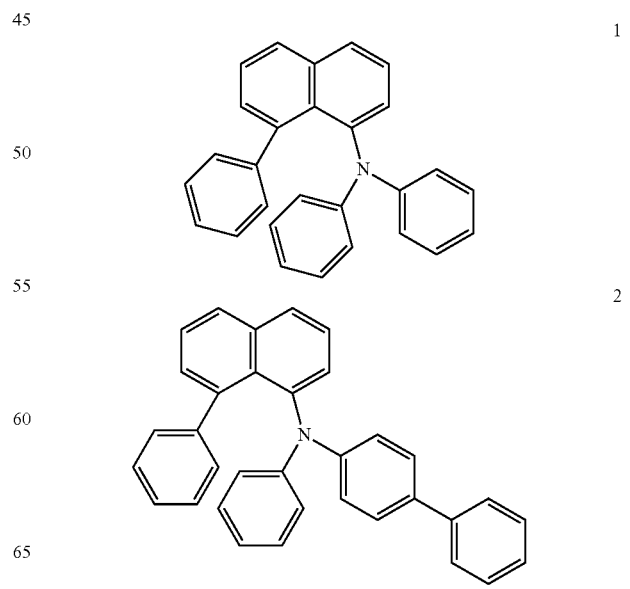

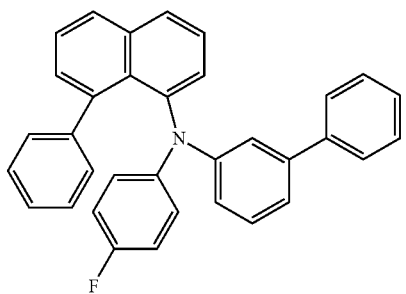
3
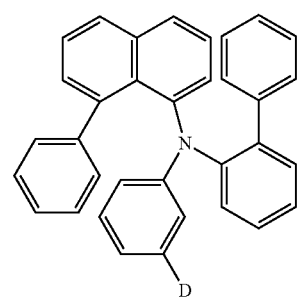
4
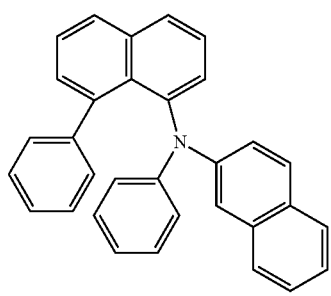
5
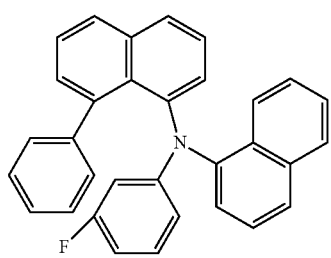
6
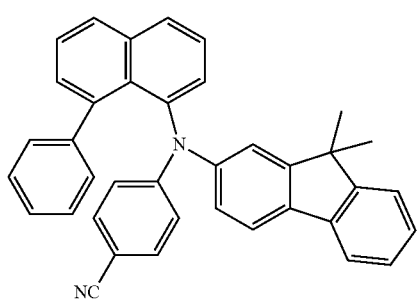
7
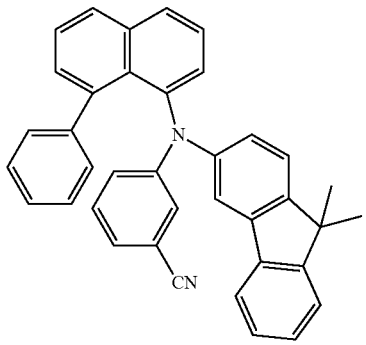
8
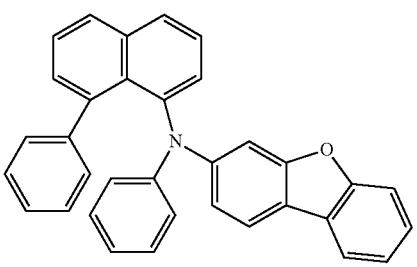
9
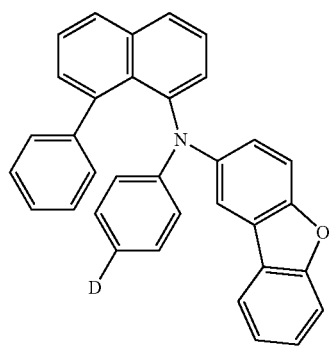
10
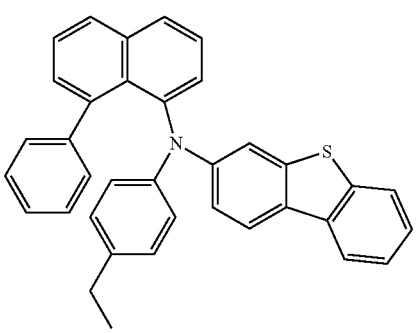
11
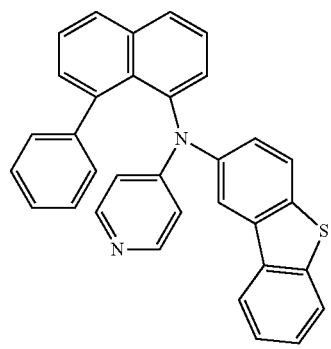
12

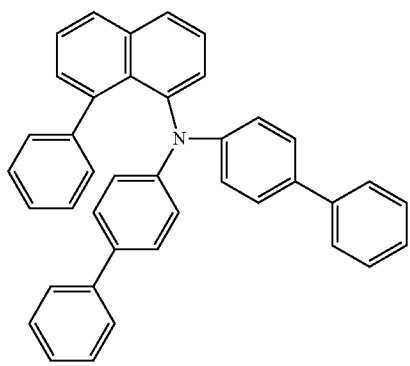
13
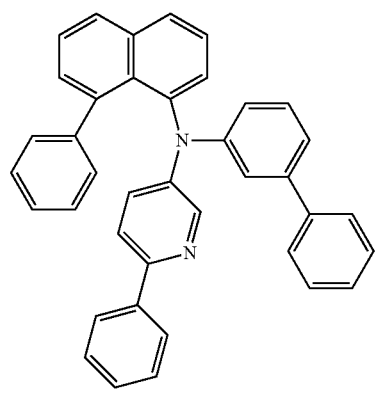
14
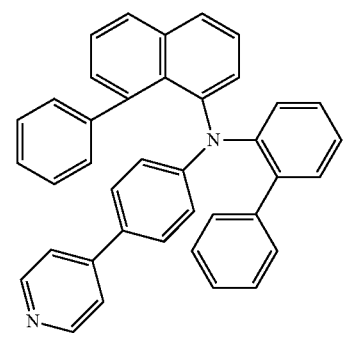
15
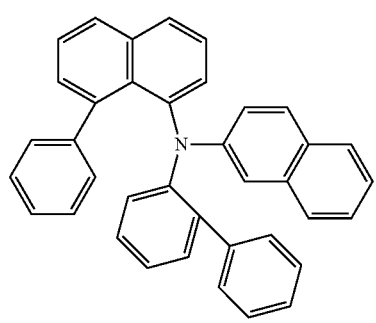
16
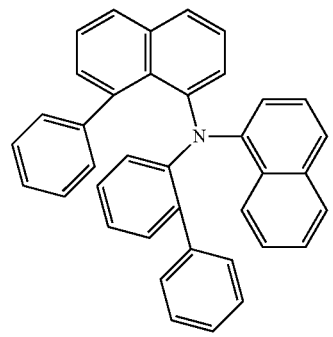
17
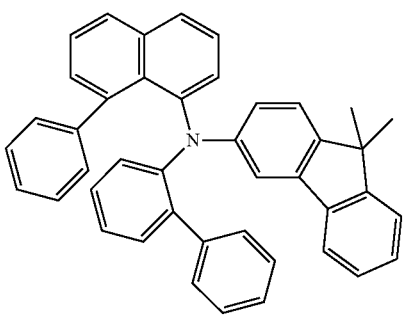
18
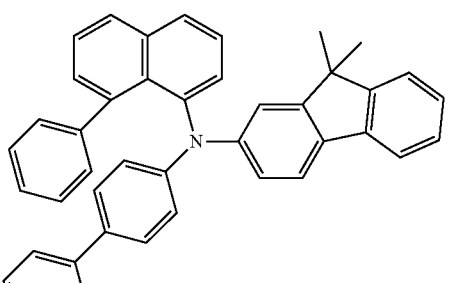
19
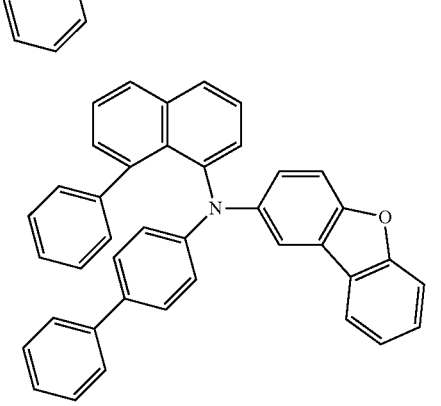
20
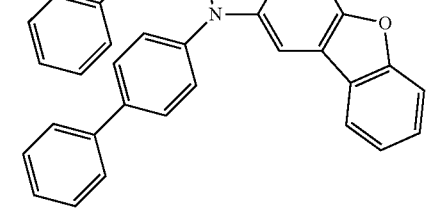
21
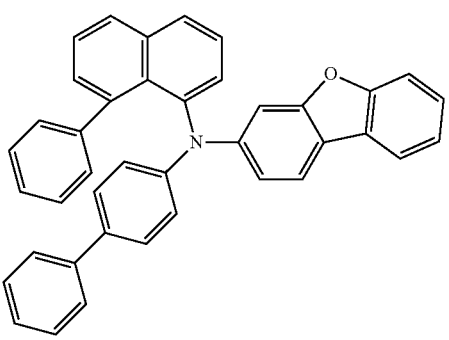

-continued
22
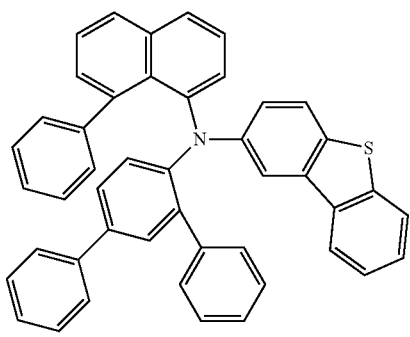
23
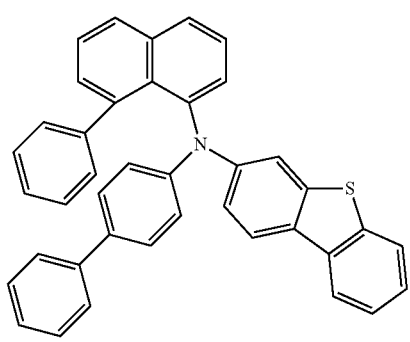
24
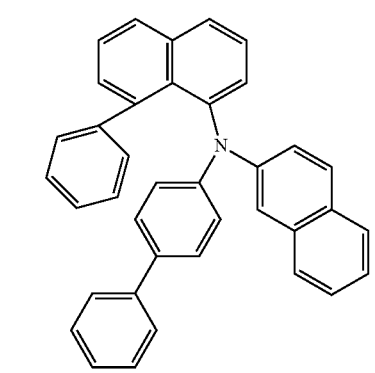
25
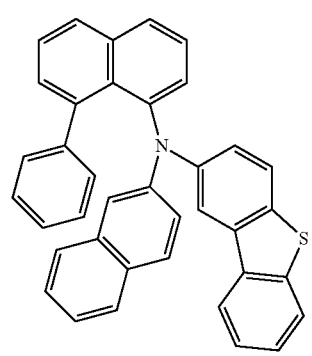
-continued
26
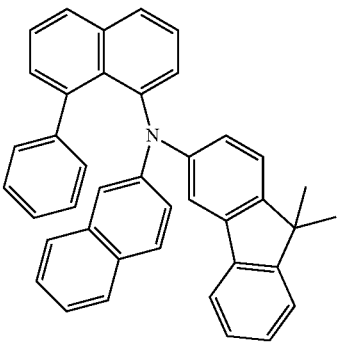
27
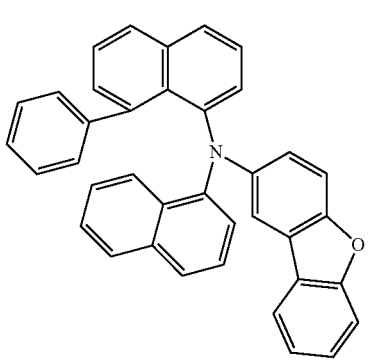
28
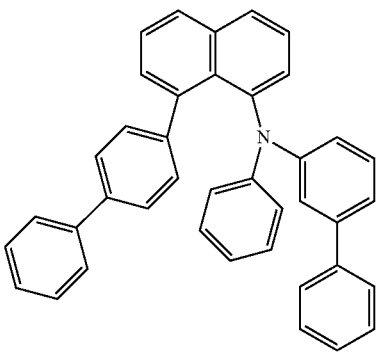
29
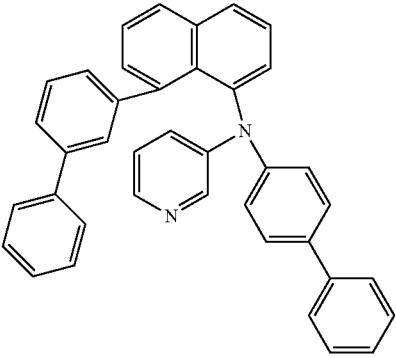

-continued
30
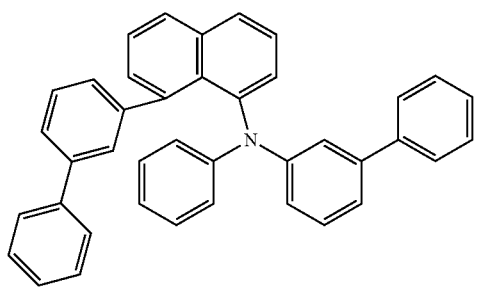
31
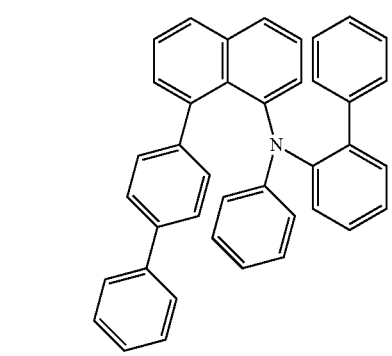
32
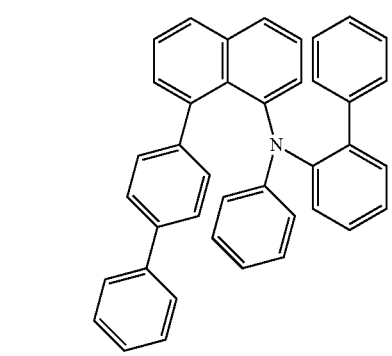
33
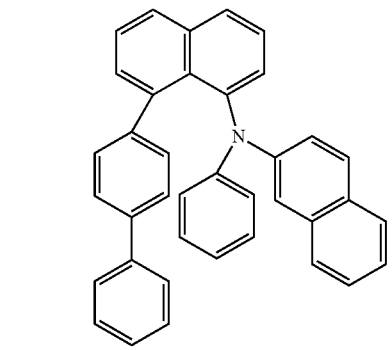
-continued
34
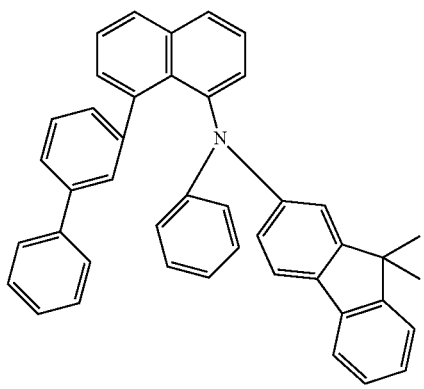
35
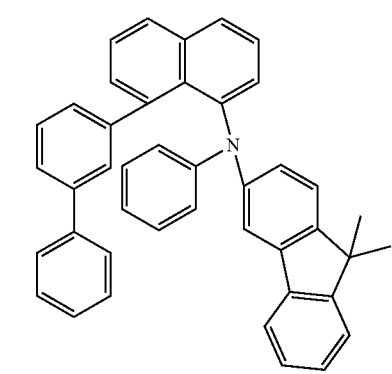
36
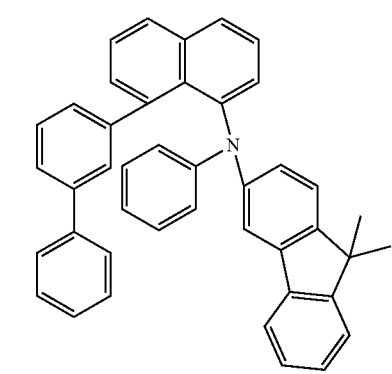
37
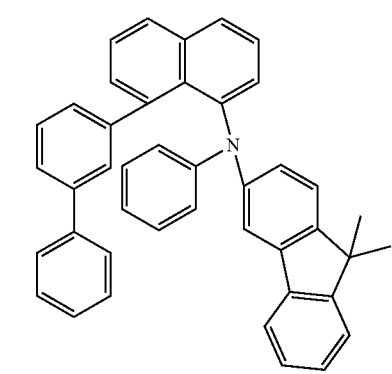

38
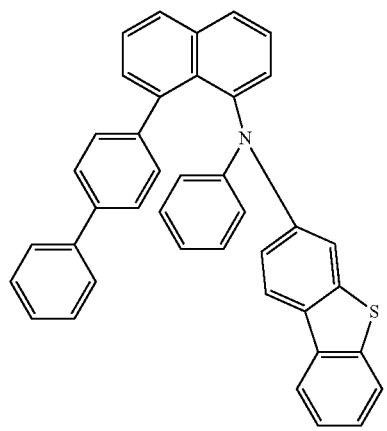
39
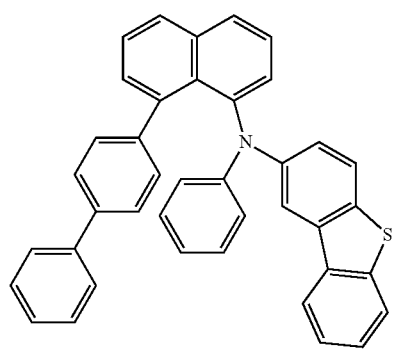
40
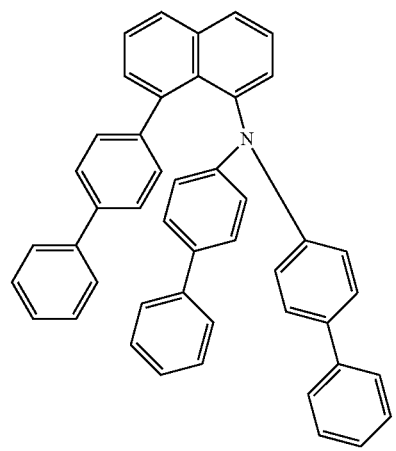
41
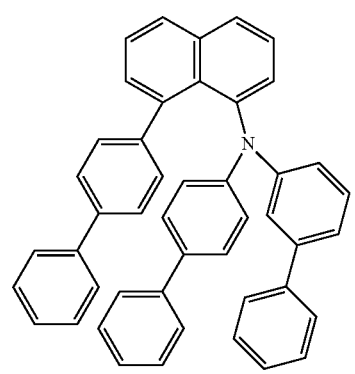
42
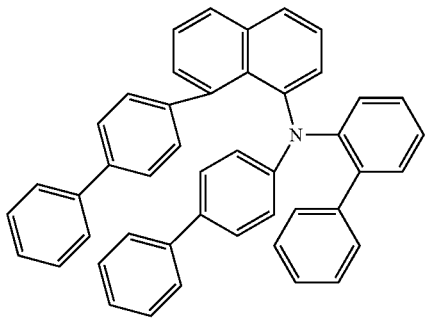
43
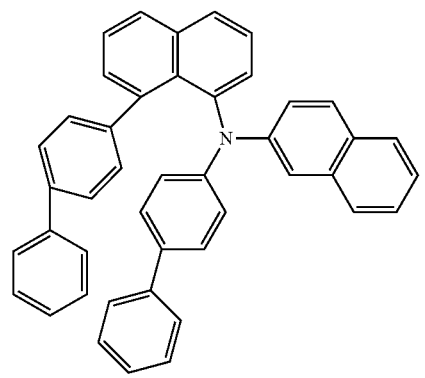
44
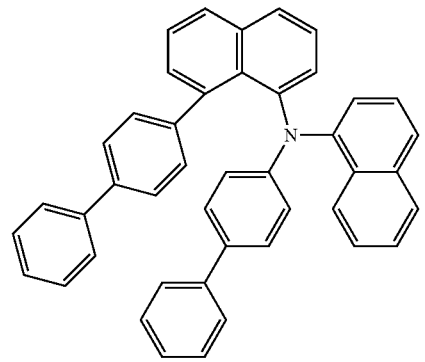
45
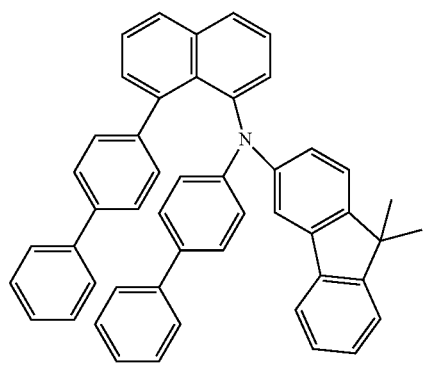

46
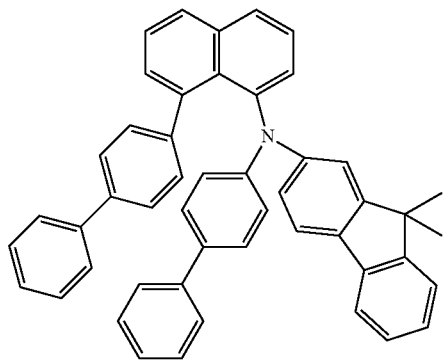
47
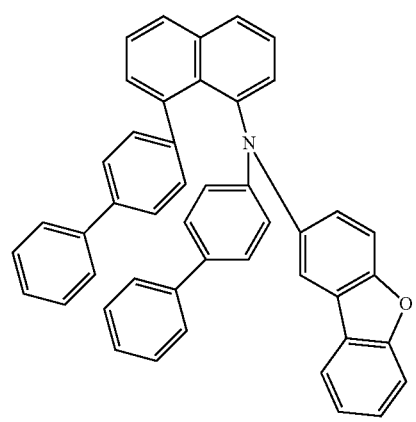
48
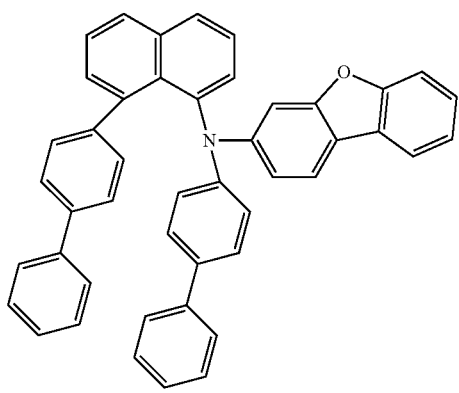
49
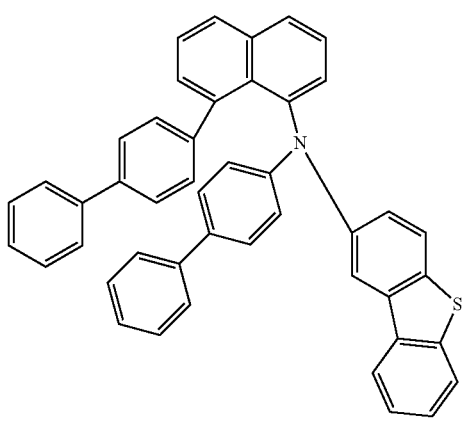
50
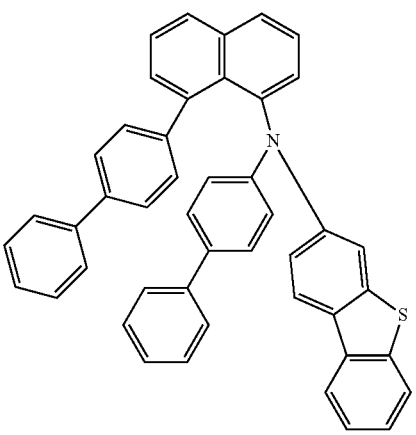
51
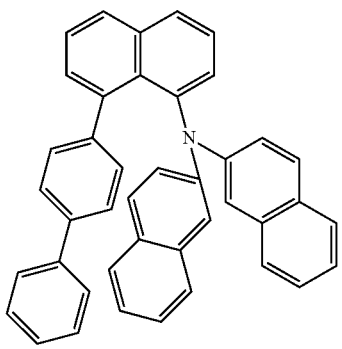
52
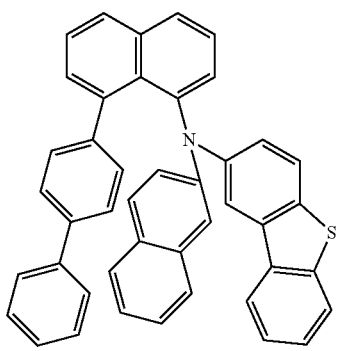
53
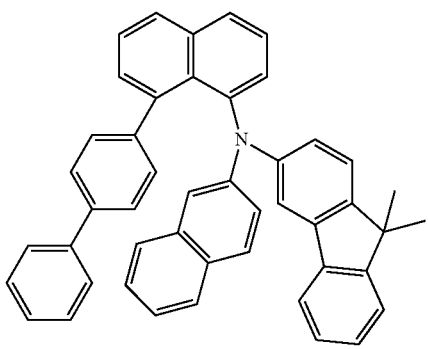

54
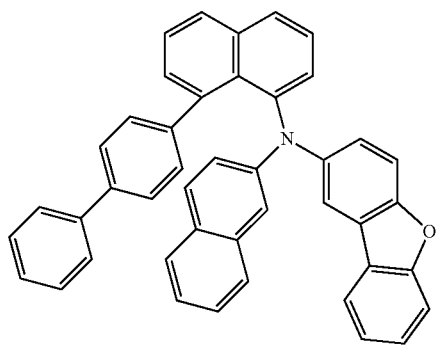
55
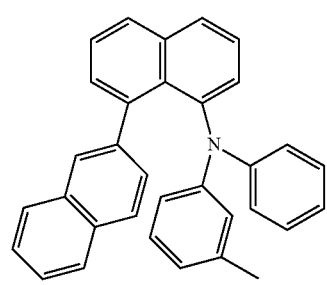
56
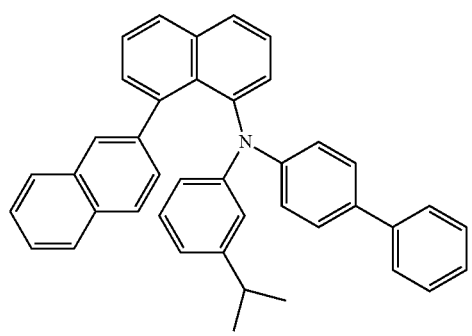
57
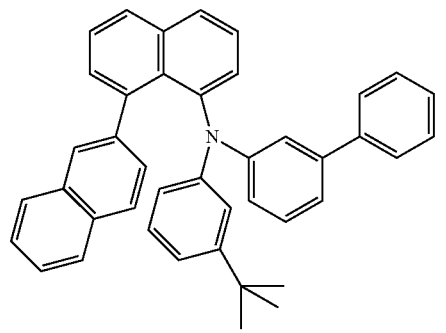
58
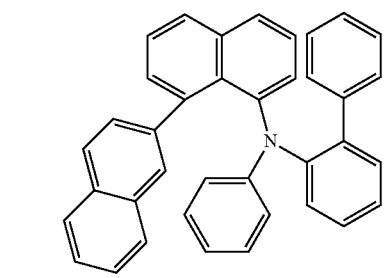
59
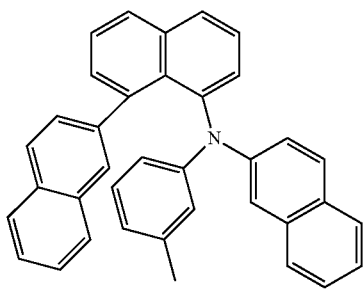
60
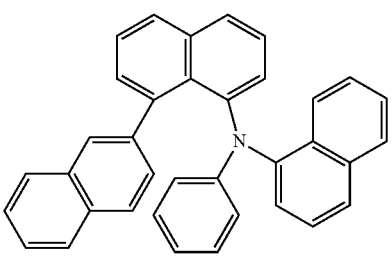
61
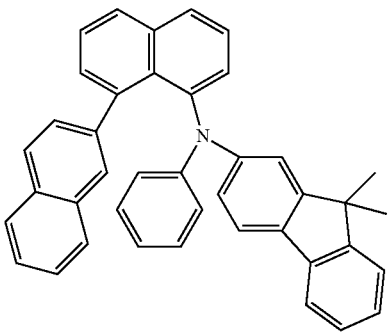
62
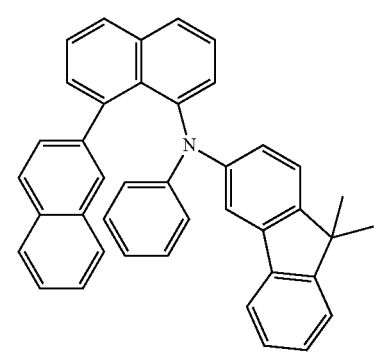
63
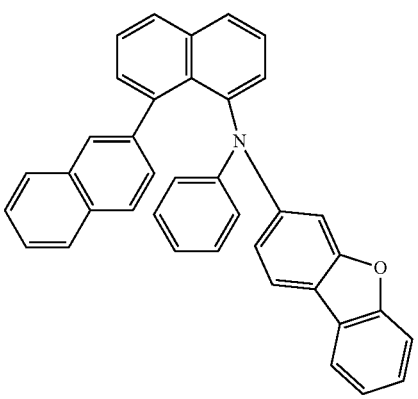

64
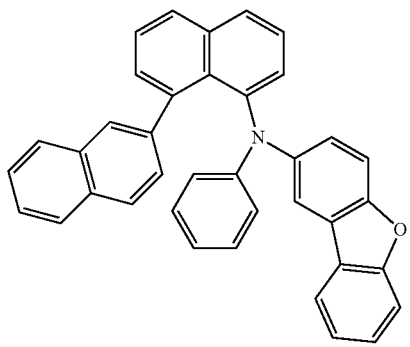
65
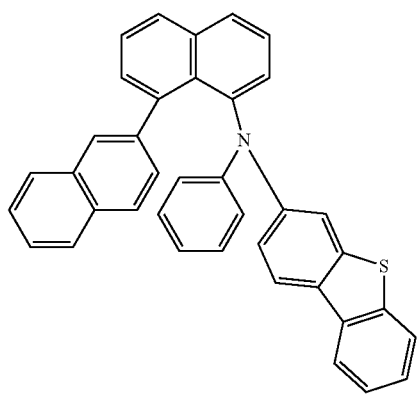
66
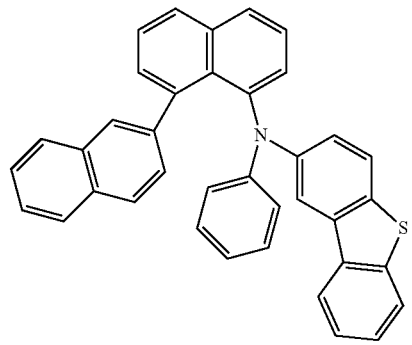
67
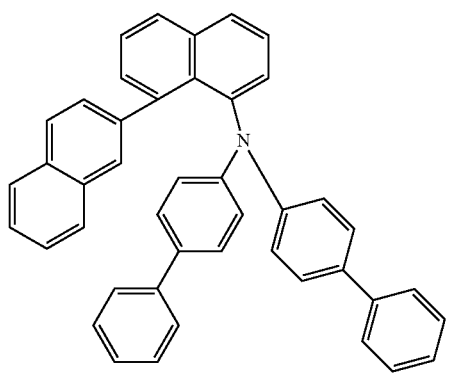
68
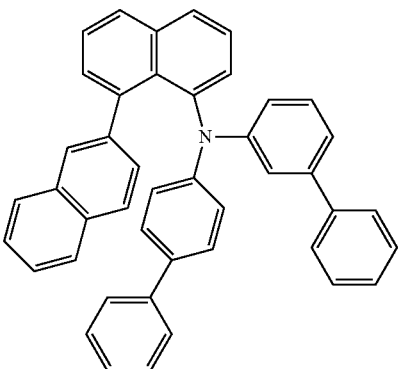
69
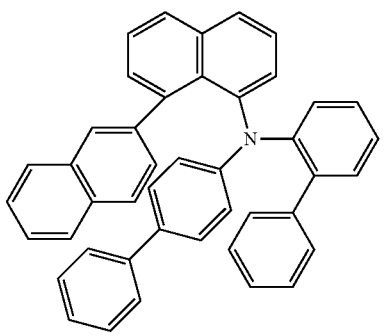
70
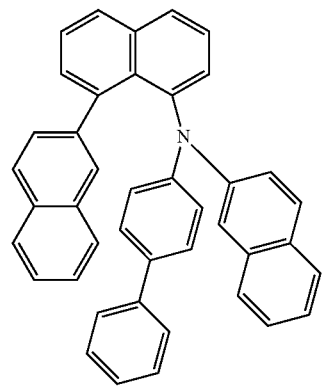
71
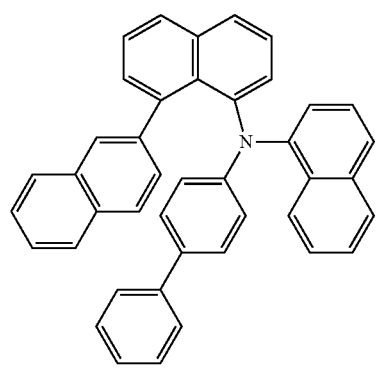

107
-continued
72
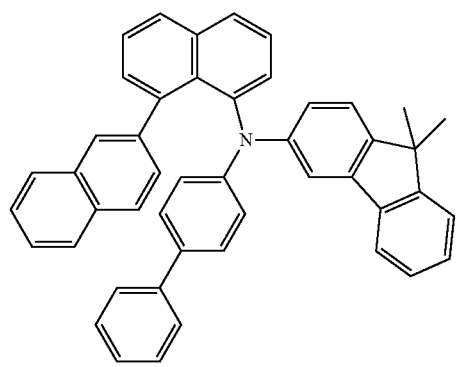
73
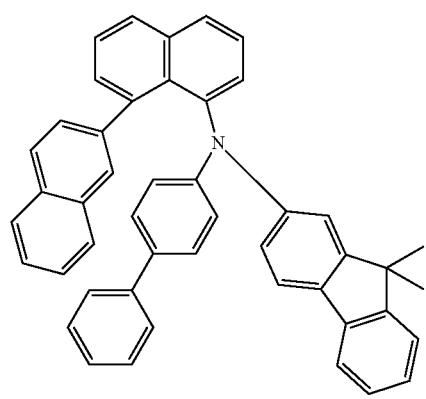
74
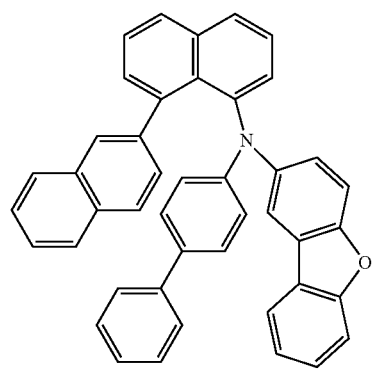
75
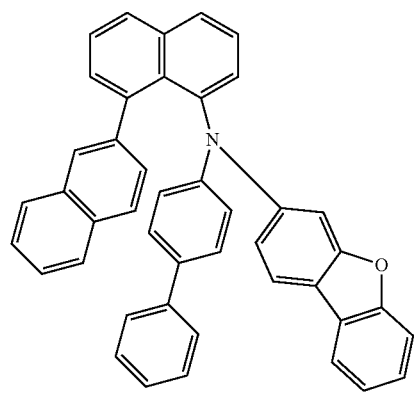
108
-continued
76
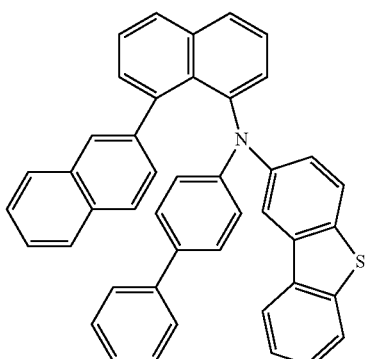
77
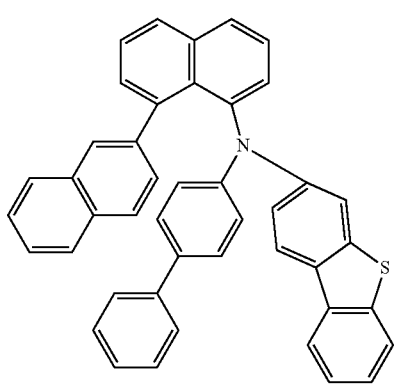
78
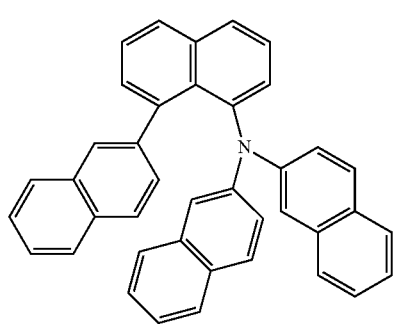
79
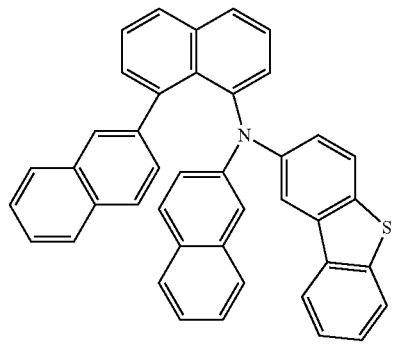

80
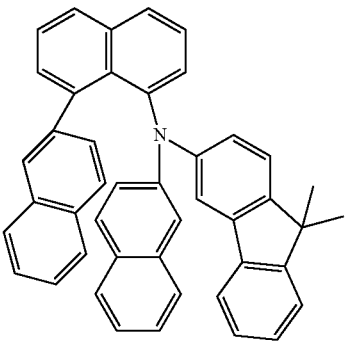
81
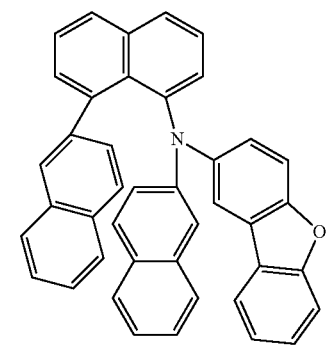
82
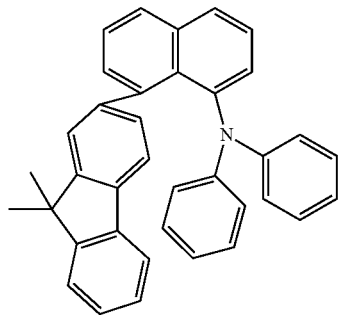
83
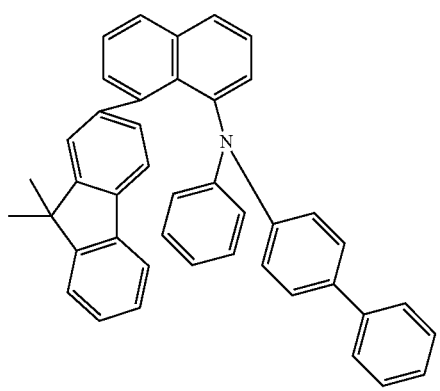
84
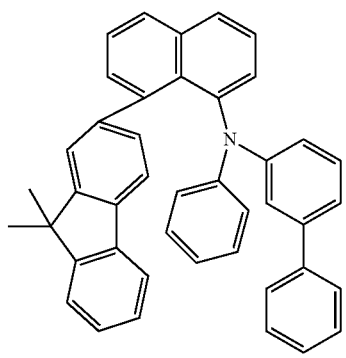
85
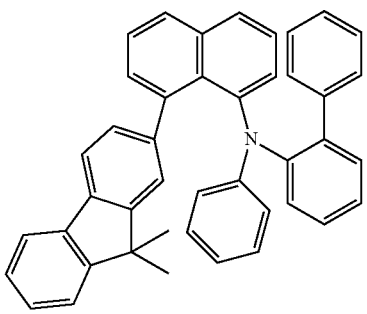
86
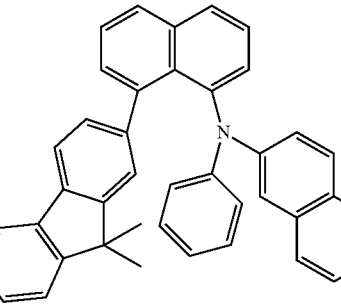
87
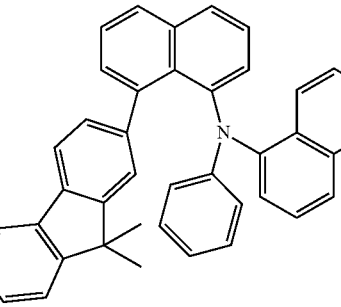
88
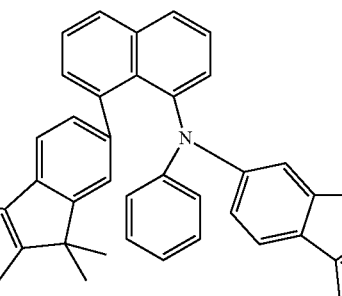

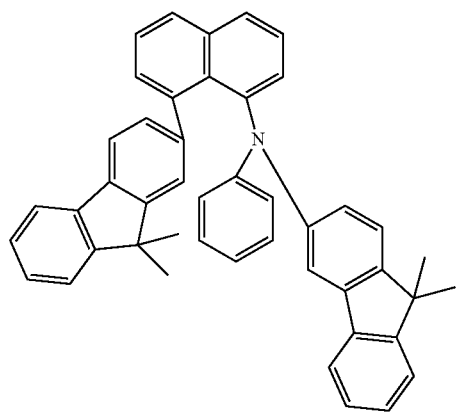
89
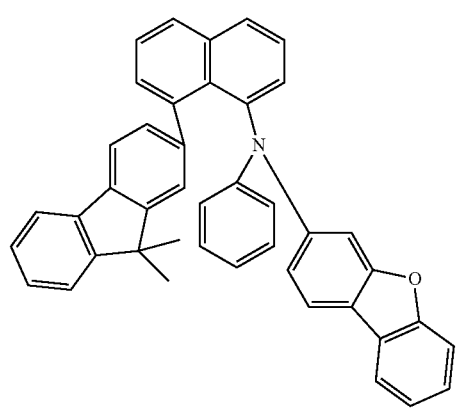
90
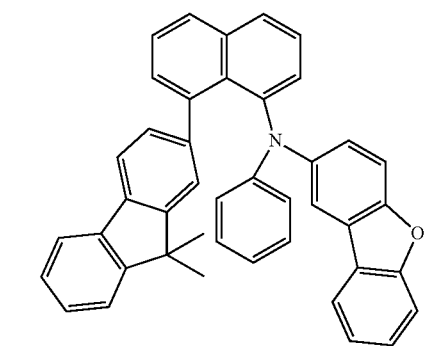
91
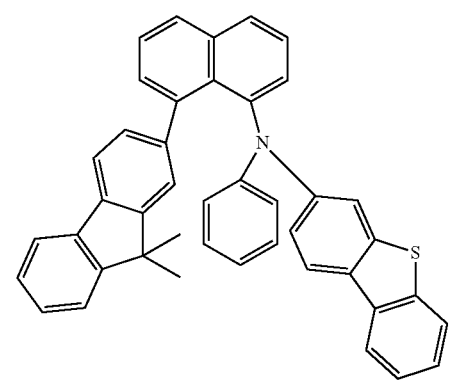
92
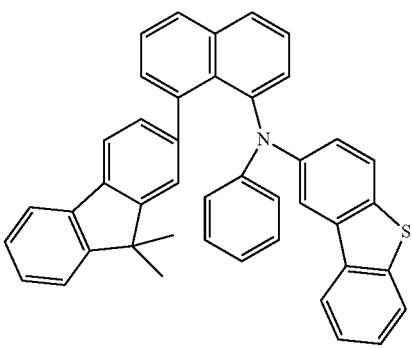
93
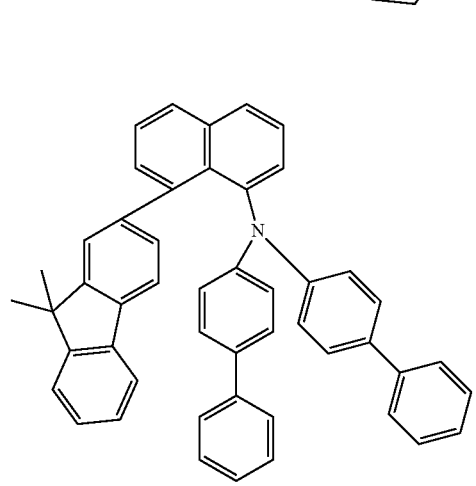
94
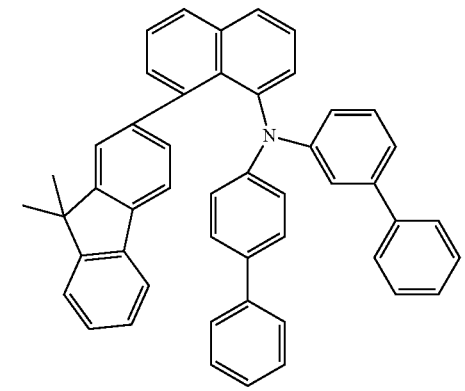
95
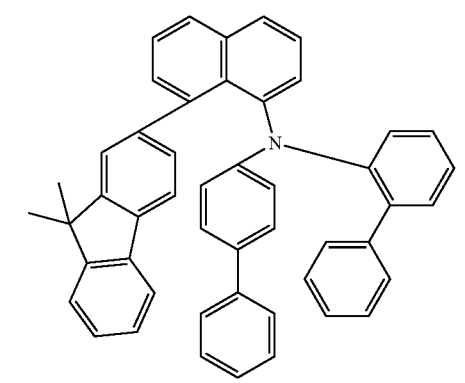
96

97
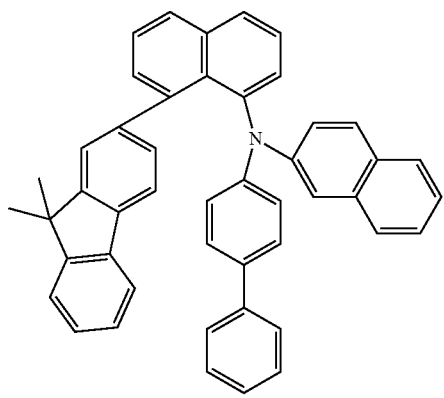
98
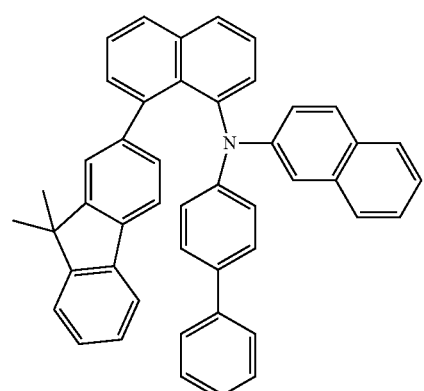
99
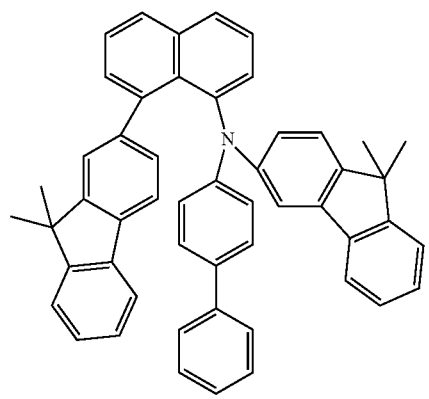
100
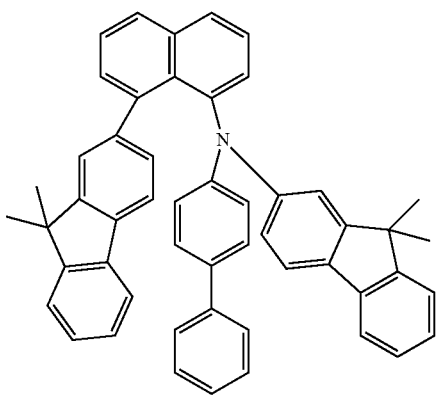
101
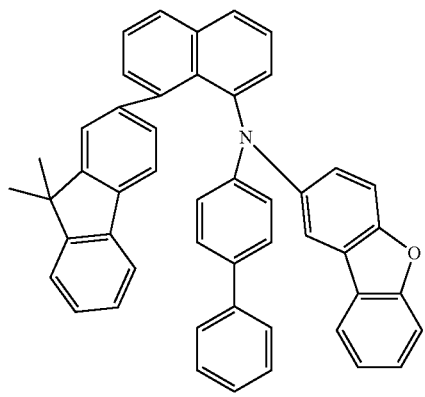
102
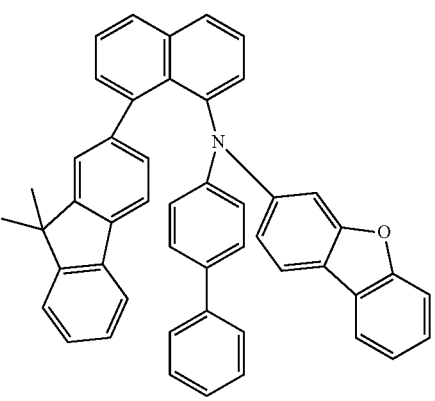
103
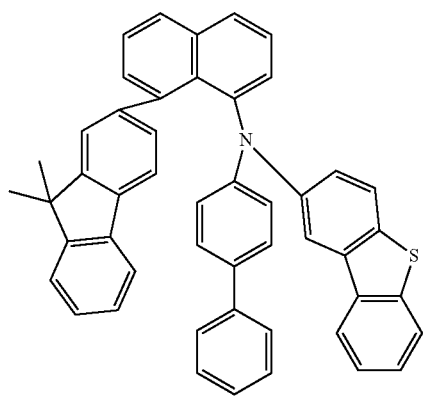
104
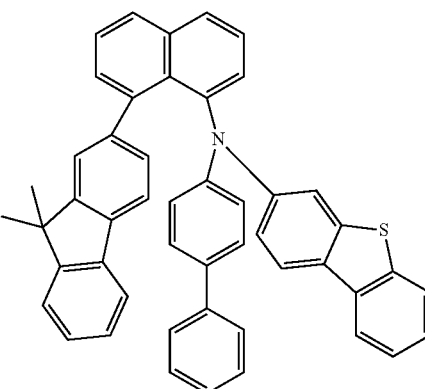

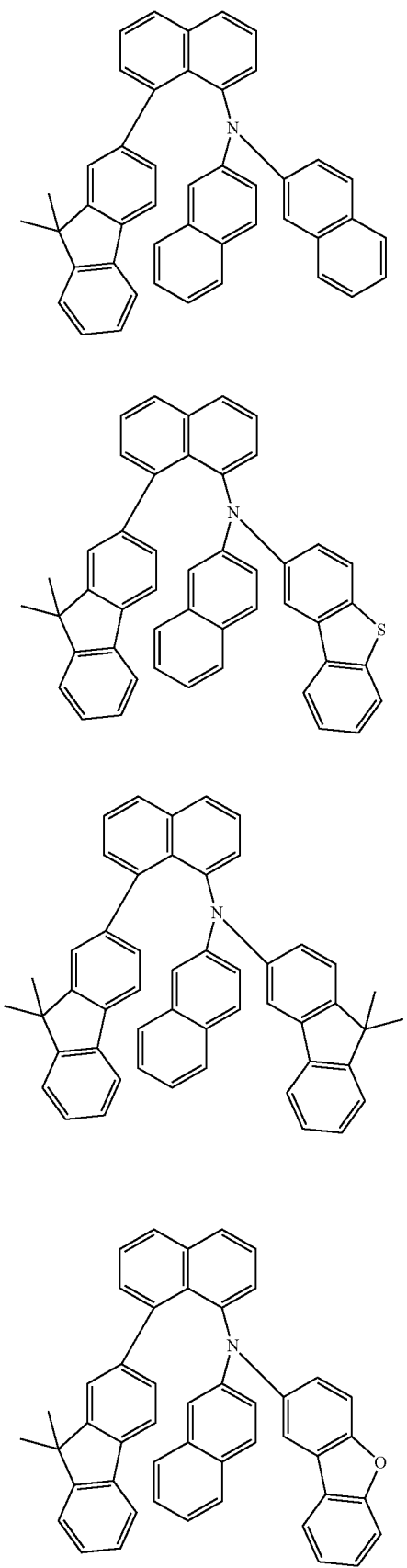
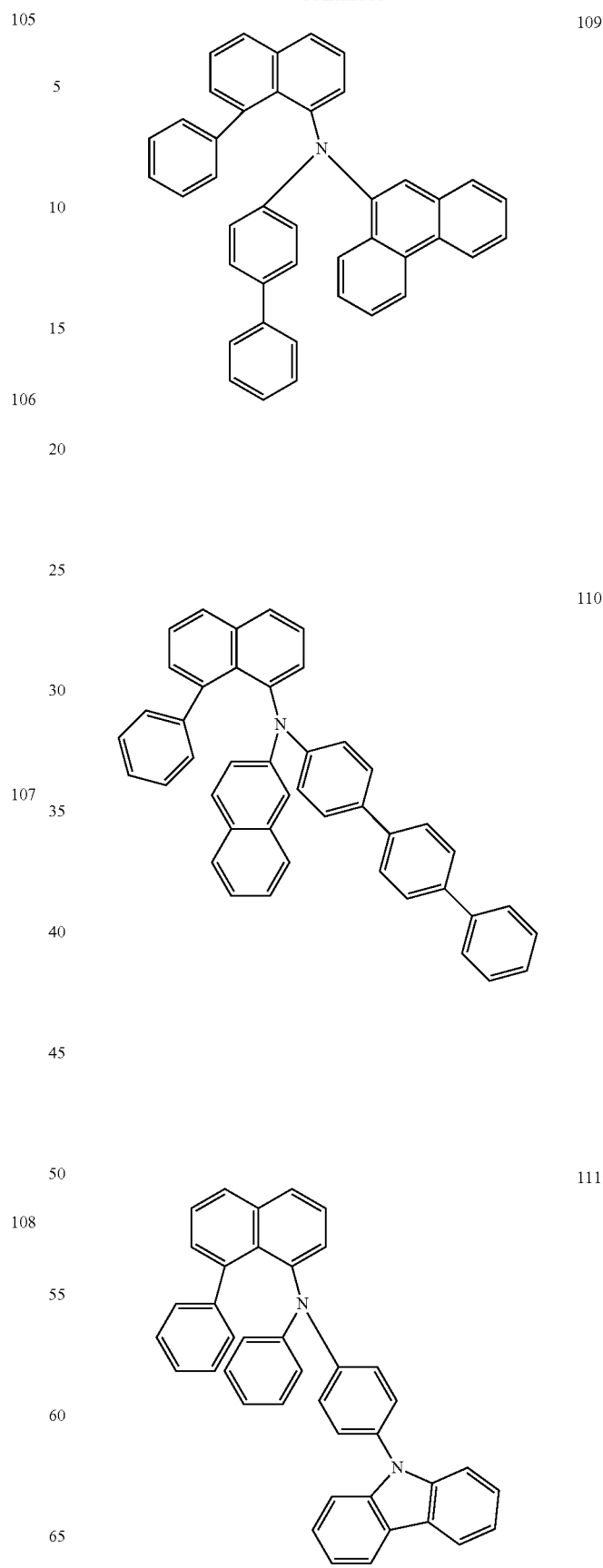

117
-continued
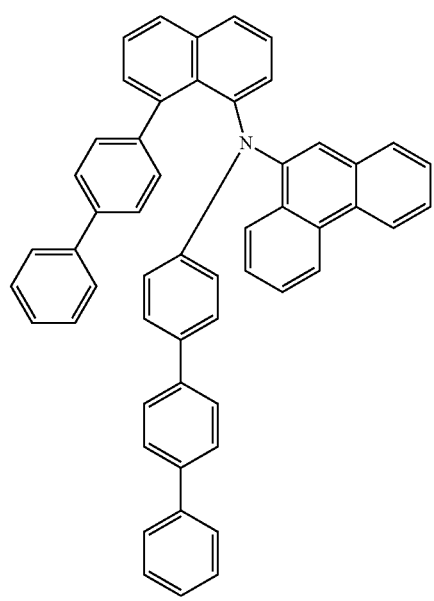
112
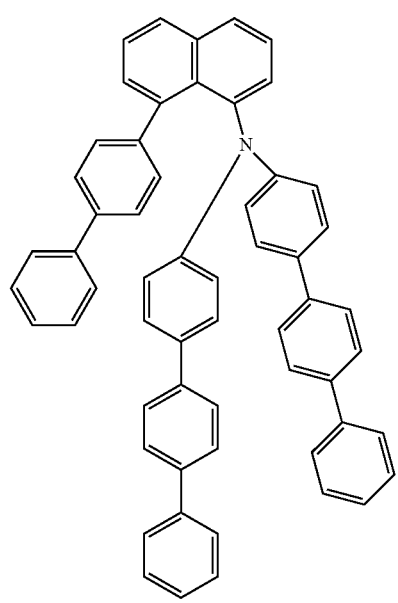
113
118
-continued
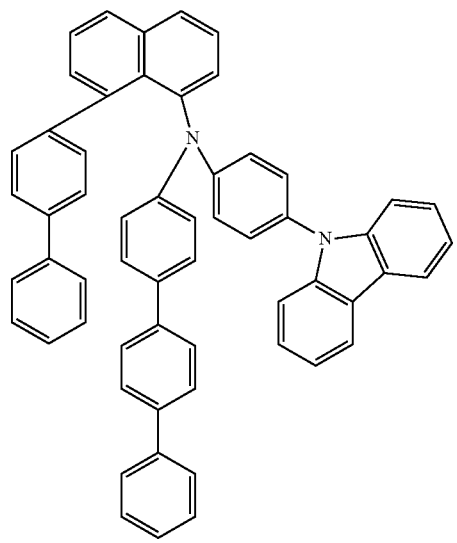
114
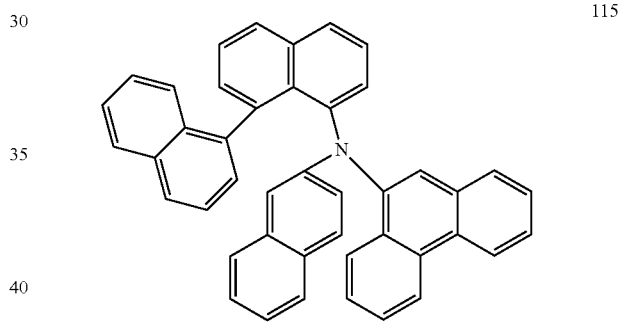
115
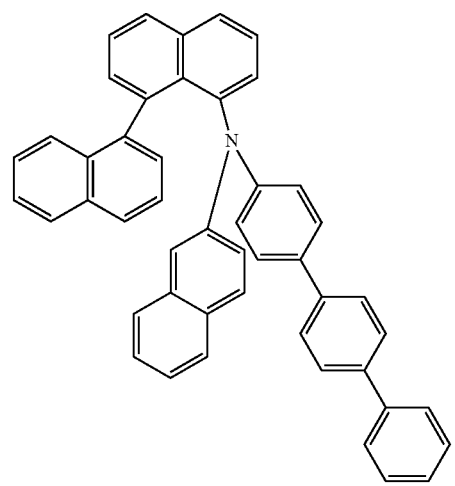
116

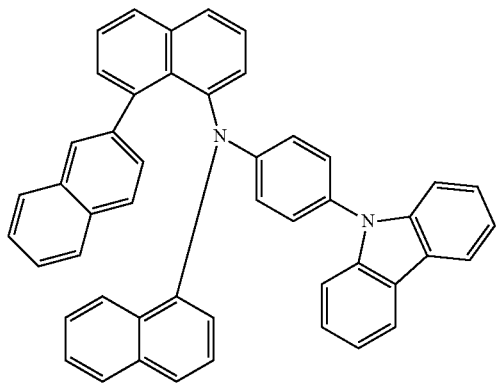
117
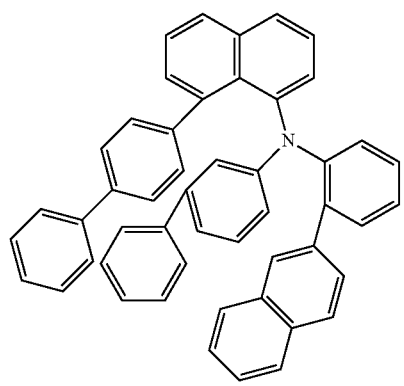
118
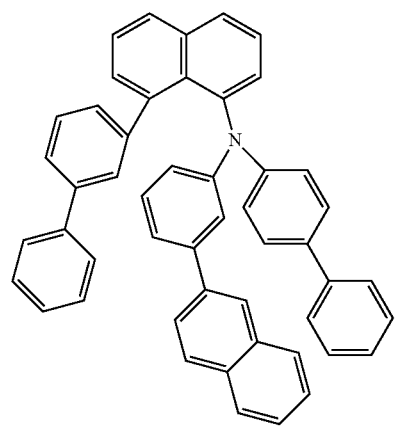
119
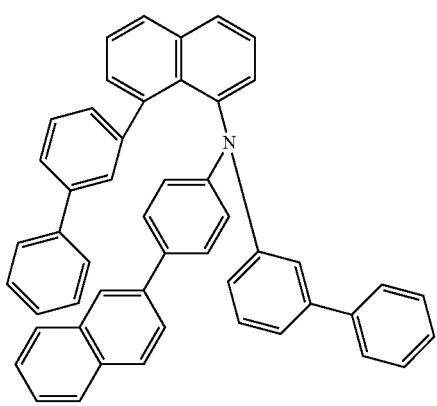
120
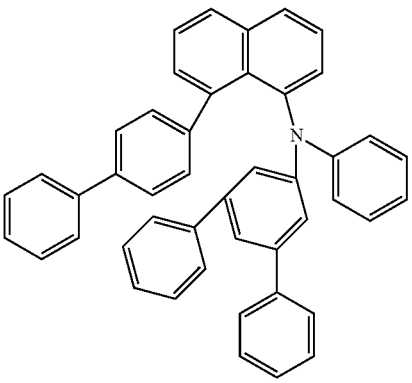
121
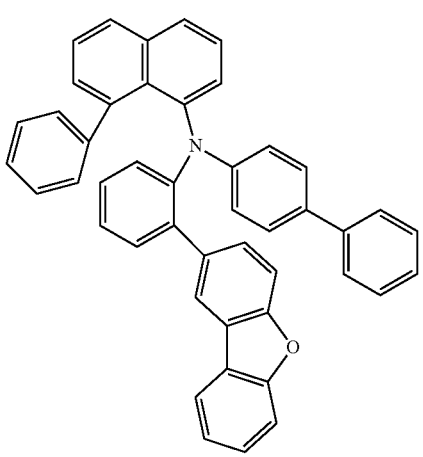
122
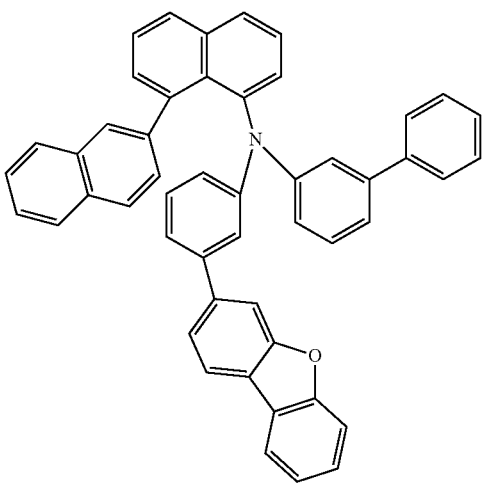
123

121
-continued
124
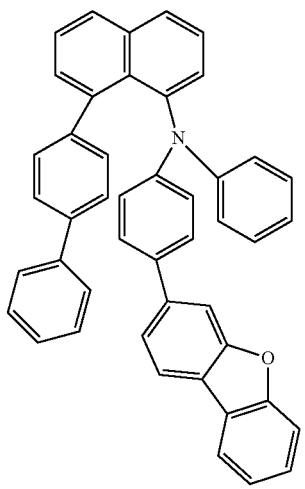
125
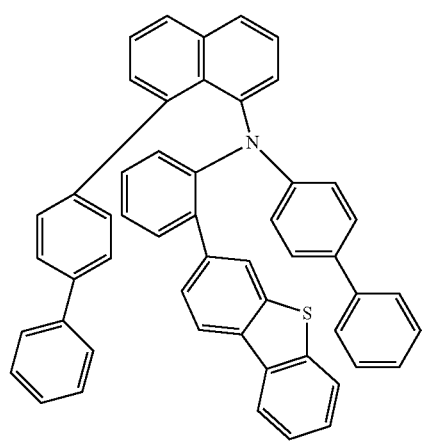
126
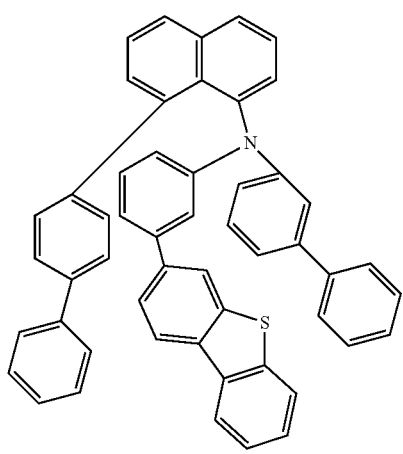
122
-continued
127
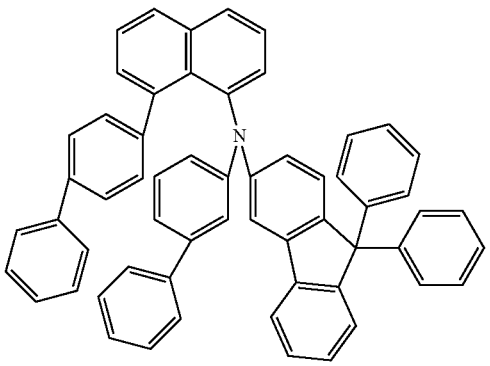
128
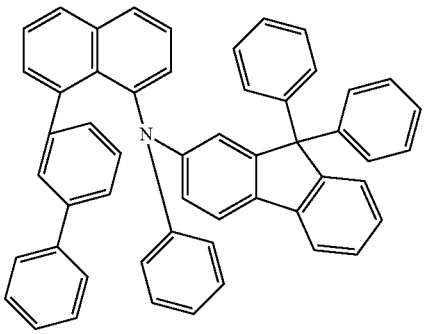
129
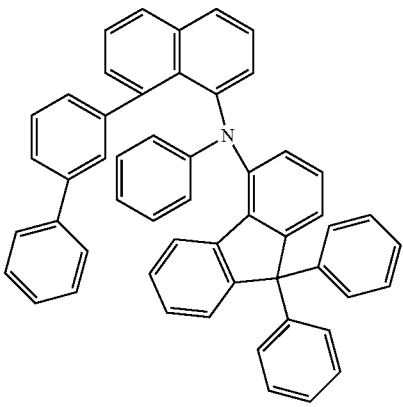

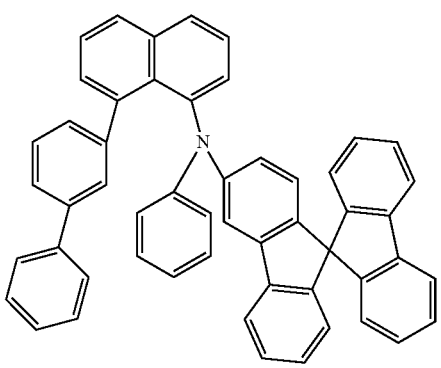

130

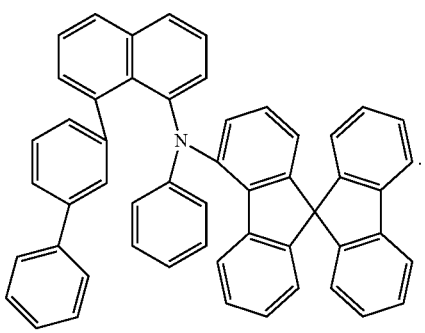

132

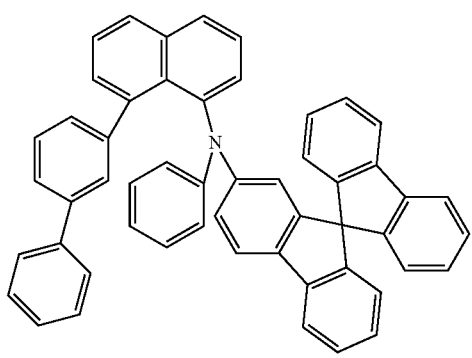

131

5. An electronic element, comprising:
an anode;
a cathode, the anode and the cathode disposed opposite to each other; and
a functional layer disposed between the anode and the cathode, wherein the functional layer comprises the nitrogen-containing compound according to claim 1.

6. The electronic element according to claim 5, wherein the functional layer comprises a hole transport layer, and the hole transport layer comprises the nitrogen-containing compound.

7. The electronic element according to claim 5, wherein the electronic element is an organic electroluminescent device or a photoelectric conversion device.

8. An electronic device comprising the electronic element according to claim 5.

* * * * *